(12) United States Patent
Schmidt et al.

(10) Patent No.: US 6,756,489 B1
(45) Date of Patent: Jun. 29, 2004

(54) SUBSTITUTED TETRAHYDROPYRANE DERIVATIVES, METHOD FOR PRODUCING SAME, THEIR USE AS MEDICINE OR DIAGNOSTIC AGENT, AS WELL AS MEDICINE CONTAINING SAME

(75) Inventors: Wolfgang Schmidt, Frankfurt (DE); Stephan Henke, Hofheim (DE); Horst Kunz, Mainz (DE); Christopher Kallus, Mainz (DE); Till Opatz, Mainz (DE); Tobias Wunberg, Mainz (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/485,233

(22) PCT Filed: Aug. 7, 1998

(86) PCT No.: PCT/EP98/05025

§ 371 (c)(1), (2), (4) Date: Apr. 25, 2000

(87) PCT Pub. No.: WO99/07718

PCT Pub. Date: Feb. 18, 1999

(30) Foreign Application Priority Data

Aug. 8, 1997 (DE) .......................................... 197 34 392
May 9, 1998 (DE) .......................................... 198 20 815

(51) Int. Cl.⁷ ............................................. C07H 15/04
(52) U.S. Cl. ...................... 536/4.1; 536/16.8; 536/17.7
(58) Field of Search ............................... 536/4.1, 16.8, 536/17.7

(56) References Cited

U.S. PATENT DOCUMENTS

| | | | | | |
|---|---|---|---|---|---|
| 5,185,436 A | * | 2/1993 | Villa et al. | ..................... | 536/4.1 |
| 5,220,008 A | | 6/1993 | Sabesan | ....................... | 536/4.1 |
| 5,635,612 A | * | 6/1997 | Kahne | ....................... | 536/18.5 |
| 5,686,426 A | * | 11/1997 | Martel et al. | ................. | 514/25 |
| 5,696,246 A | * | 12/1997 | Schmidt et al. | ............ | 536/18.5 |
| 5,716,812 A | * | 2/1998 | Withers et al. | .............. | 435/74 |
| 5,780,603 A | * | 7/1998 | Hindsgaul | .................... | 536/4.1 |
| 5,998,595 A | * | 12/1999 | Kusumoto et al. | ......... | 536/18.5 |
| 6,013,779 A | * | 1/2000 | Wong et al. | ................ | 536/18.6 |
| 6,040,433 A | * | 3/2000 | Kahne | ....................... | 536/4.1 |
| 6,242,583 B1 | * | 6/2001 | Schmidt et al. | ............ | 536/1.11 |
| 6,297,363 B1 | * | 10/2001 | Kubo et al. | ................ | 536/17.4 |

FOREIGN PATENT DOCUMENTS

| EP | 0 319 253 A2 | 6/1989 |
|---|---|---|
| WO | WO 94 19360 A1 | 9/1994 |
| WO | WO 95 18814 A2 | 7/1995 |

OTHER PUBLICATIONS

Bazin, H. et al "Hydrolysis of cyanoethylated carbohydrates" J. Carbohyd. Chem., vol 14, No. 8, pp. 1187–1207.*
Wallberg, A. et al "A 2–silylethanol–based anomeric linker for carbohydrates . . . " Tet. Lett. vol 38, No. 24, pp. 4285–4286, 1997.*
Nicolaou, N. et al "A general and highly efficient solid phase synthesis of oligosaccharides" J. Am. Chem. Soc. vol 119, pp. 449–450.*
Aldrich catalog, 1992–1993 edition.*
Adinolfi, Matteo; Barone, Gaspare; De Napoli, Lorenzo; Iadonisi, Alfonso; and Piccialli, Gennaro, "Solid Phase Synthesis of Oligosaccharides," *Tetrahedron Letters*, vol. 37, No. 28, 1996, pp. 5007–5010.
Douglas, Stephen P.; Whitefield, Dennis M.; and Krepinsky, Jiri J., "Polymer–Supported Solution Synthesis of Oligosaccharides," *J. Am. Chem. Soc.*, vol. 113, 1991, pp. 5095–5097.
Nicolaou, K.C.; Trujillo, John L.; and Chibale, Kelly, "Design, Synthesis and Biological Evaluation of Carbohydrate–Based Mimetics of cRGDFV," *Tetrahedron*, vol. 53, No. 26, 1997, pp. 8751–8778.
Roberge, Jacques Y.; Beebe, Xenia; and Danishefsky, Samuel J., "A Strategy for a Convergent Syunthesis of N–Linked Glycopeptides on a Solid Support," *Science*, vol. 269, Jul. 14, 1995, pp. 202–204.
Schmidt, Richard R., "Recent developments in the synthesis of glycoconjugates," *Pure & Appl. Chem.*, vol. 61, No. 7, 1989, pp. 1257–1270.
Yan, Lin; Taylor, Carol M.; Goodnow, Jr., Robert; and Kahne, Daniel, "Glycosylation on the Merrifield Resin Using Anomeric Sulfoxides," *J. Am. Chem. Soc.*, vol. 116, 1994, pp. 6953–6954.

* cited by examiner

Primary Examiner—James O. Wilson
Assistant Examiner—Leigh C. Maier
(74) Attorney, Agent, or Firm—Finnegan, Henderson, Farabow, Garrett & Dunner, L.L.P.

(57) ABSTRACT

Substituted tetrahydropyran derivatives, processes for their preparation, their use as a pharmaceutical or diagnostic, and pharmaceutical comprising them. The invention relates to compounds of the formula I

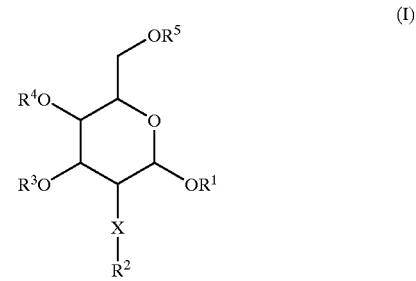

(I)

in which the radicals $R^1$, $R_2$, $R^3$, $R^4$, $R^5$ and X have the meaning mentioned in the description, a process for the preparation of the compounds of the formula I on a solid phase, and their use as pharmaceuticals.

2 Claims, No Drawings

SUBSTITUTED TETRAHYDROPYRANE DERIVATIVES, METHOD FOR PRODUCING SAME, THEIR USE AS MEDICINE OR DIAGNOSTIC AGENT, AS WELL AS MEDICINE CONTAINING SAME

This application is the National Stage filed under 35 USC 371 of PCT/EP98/05025, filed Aug. 7, 1998.

The invention relates to substituted tetrahydropyran derivatives, processes for their preparation, their use as a pharmaceutical or diagnostic and pharmaceutical comprising them.

Peptides and peptide mimetics are a valuable aid for the discovery of new lead structures and the identification of potential active compounds. By fixing side chains in a rigid structure (scaffold), it is hoped, in comparison with the conformationally more flexible peptide chain, for an increase in the affinity of this conformationally fixed ligand for the receptor.

Very different structural units are already finding use as peptide mimetics.

Owing to their polyvalency and their defined spatial arrangement, carbohydrate units should be particularly highly suitable as structural units for peptide mimetics.

Thus, it has recently been shown that a specific monosaccharide mimics, as a conformationally fixed structure, the spatial arrangement of a certain cyclopeptide, somatostatin (K. C. Nicolaou, J. I. Trujillo, K. Chibale, Tetrahedron 1997, 53, 8751–8778).

In this connection, starting from a glucose derivative having standard protective groups, a restricted variation of the simply accessible anomeric hydroxyl function and the C-6 hydroxyl function was carried out. The synthesis strategy described there starts from already known sugar units and is restricted by the protective group:strategy to a narrow application range of somatostatin. At the same time, the method is not transferable to the targeted variation of the structural unit by solid-phase synthesis.

The previous syntheses of carbohydrate derivatives in solution or in the form of substance libraries on a solid phase concentrated, in particular, on the synthesis of oligosaccharides or glycopeptides (L. DeNapoli et al., Tetrahedron Letters 1996, 37, 5007–5010; S. J. Danishefsky et al., Science 1995, 269, 202–204, J. J. Krepinski et al., J. Am. Chem. Soc., 1991, 113, 5095–5097).

Compounds synthesized from oligosaccharide or glycopeptide units are, however, of only very restricted use for the discovery of lead structures or as potential active compounds on account of their complexity.

Restriction to a monosaccharide as a structural unit, however, combines the positive property of the defined spatial arrangement of the ligands with a low complexity, low molecular weight, low toxicity and further properties which are of importance for potential active compounds.

On account of the polyvalency of the monosaccharides, targeted synthesis of selectively functionalized monosaccharides—both in solution and on the solid phase—causes great difficulties.

Variously protected carbohydrate units are likewise known as a result of the various studies on carbohydrate chemistry (see R. R. Schmidt, Pure & Appl. Chem. 1989, 61, 1257). In the intermediates described there, the hydroxyl groups are temporarily blocked more or less selectively by protective groups which are then deprotected for linkage with other protective groups, as a result of which the synthesis of di- or oligosaccharides takes place.

These intermediates or the polysugars synthesized therefrom are, however, of only restricted use for specific lead structure discovery and as potential active compounds. In some cases, these structures are relatively labile and thus not resistant to degradation or cleavage.

The linkers and activation strategies developed for the preparation of the abovementioned polysaccharides or glycopeptides (D. Kahne et al., J. Am. Chem. Soc. 1994, 116, 6953–6954) are also not generally transferable to the preparation of selectively polysubstituted monosaccharide compounds.

The specific synthesis of selectively functionalized monosaccharide derivatives therefore requires the development of a novel, completely orthogonal protective group strategy, which makes it possible to selectively remove the protective groups of all functional groups, the conditions used for this being stable to the conditions of the synthesis sequence. At the same time, these protective groups must guarantee compatibility with all reaction conditions which are necessary for synthesis in solid-phase synthesis. For synthesis on a solid phase, it is furthermore necessary to have available a linker system for linking the monosaccharide unit, preferably via the anomeric center, which is compatible with all reaction conditions and can be selectively activated. Such a strategy makes possible the specific different variation of all functionalities of the monosaccharide unit to give stable final products.

The invention thus relates to compounds of the formula I

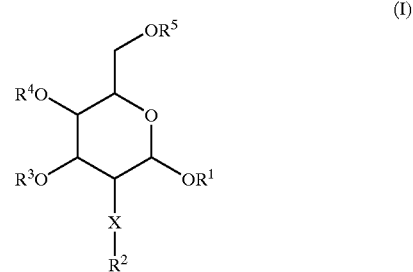

(I)

in which:
$R^1$, $R^2$, $R^3$, $R^4$, $R^5$ independently of one another are
1. hydrogen;
2. $(C_1-C_{12})$-alkyl;
3. $(C_2-C_8)$-alkenyl;
4. $(C_2-C_8)$-alkynyl;
5. $(C_1-C_6)$-alkylene-$(C_3-C_{10})$-cycloalkyl;
6. $(C_0-C_6)$-alkylene-$(C_6-C_{12})$-aryl; preferably phenyl or benzyl;
7. $(C_1-C_6)$-alkoxy;
8. $(C_0-C_6)$-alkylene-CO—$R^8$;
9. $(C_1-C_6)$-alkylene-$(C_1-C_9)$-heteroaryl;
10. carbamoyl;
11. —C(O)NR$^6$R$^7$;
12. —C(O)OR$^6$;
13. a radical defined as in 2.-12., which is mono-, di- or polysubstituted in the alkyl moiety and/or aryl or heteroaryl moiety by a radical from the group consisting of $(C_1-C_6)$-alkyl, $NO_2$, CN, halogen, $CF_3$ or $(C_1-C_6)$-alkoxy;
14. a radical defined as in 6. and 9., which is substituted in the aryl or heteroaryl moiety by one, two or more halogen atoms;

$R^6$ and $R^7$ independently of one another are:
1. hydrogen;
2. $(C_1-C_{12})$-alkyl;
3. $(C_2-C_8)$-alkenyl;

4. $(C_2-C_8)$-alkynyl;
5. $(C_1-C_6)$-alkylene-$(C_3-C_{10})$-cycloalkyl;
6. $(C_1-C_6)$-alkylene-$(C_6-C_{12})$-aryl; preferably benzyl;
7. $(C_2-C_6)$-alkyloxy;
8. $(C_0-C_6)$-alkylene-CO—$R^8$;
9. $(C_1-C_6)$-alkylene-$(C_1-C_9)$-heteroaryl;
10. $(C_0-C_6)$-alkylene-$(C_1-C_6)$-alkoxy;
11. $(C_3-C_{10})$-cycloalkyl;
12. $(C_6-C_{12})$-aryl, preferably phenyl;

$R^8$ is hydrogen, $(C_1-C_6)$-alkyl, $(C_6-C_{12})$-aryl or $OR^{12}$;

$R^{12}$ is hydrogen, $(C_1-C_6)$-alkyl or $(C_6-C_{12})$-aryl; or $R^2$ and $R^3$ together or $R^3$ and $R^4$ together or $R^4$ and $R^5$ together are $(C_1-C_3)$-alkylene which can be substituted by 1 or 2 $(C_1-C_3)$-alkyl radicals or optionally substituted $(C_6-C_{12})$-aryl radicals;

X is N or O;

with the proviso that $R^2$ is not —C(O)OR$^6$ when X is O;

and their physiologically tolerable salts.

Preferred compounds of the formula I are those in which the radicals $R^1$, $R^2$, $R^3$, $R^4$ and $R^5$ do not each have the same meaning, and their physiologically tolerable salts.

Preferred compounds of the formula I are furthermore those in which only three of the radicals $R^1$, $R^2$, $R^3$, $R^4$, $R^5$ have the same meaning, and their physiologically tolerable salts.

Particularly preferred compounds of the formula I are those in which only two of the radicals $R^1$, $R^2$, $R^3$, $R^4$, $R^5$ have the same meaning, and their physiologically tolerable salts.

Very particularly preferred compounds of the formula I are those in which all radicals $R^1$, $R^2$, $R^3$, $R^4$, $R^5$ have a different meaning, and their physiologically tolerable salts.

Preferred compounds of the formula I are those in which at least one of the radicals $R^1$, $R^2$, $R^3$, $R^4$, $R^5$ is hydrogen, —C(O)NR$^6$R$^7$, $(C_1-C_8)$-alkyl, $(C_0-C_6)$-alkyl-$(C_6-C_{12})$-aryl, preferably phenyl or benzyl; the aryl moiety of the $(C_1-C_6)$-alkyl-$(C_6-C_{12})$-aryl radical being unsubstituted or mono-, di- or trisubstituted by $(C_1-C_6)$-alkyl, cyano, nitro, $CF_3$, Cl, Br or $(C_1-C_4)$alkoxy, preferably methoxy, and $R^6$ and $R^7$ independently of one another are hydrogen, $(C_1-C_4)$-alkyl, benzyl, $(C_1-C_3)$-alkylene-$(C_3-C_7)$-cycloalkyl, $(C_1-C_3)$-alkylene-CO—OR$^{12}$, $(C_1-C_3)$-alkylene-$(C_1-C_3)$-alkoxy, phenyl, optionally substituted by one or two radicals from the group consisting of $CF_3$, Cl, Br, F, nitro, cyano; and $R^{12}$ is as defined above;

or $R^3$ and $R^4$ together or $R^4$ and $R^5$ together are —CH$_2$— which is substituted by 1 or 2 methyl radicals or optionally substituted phenyl radicals, and the other radicals are as defined above, and their physiologically tolerable salts.

Preferred compounds of the formula I are also those in which X is equal to —O— and the other radicals are as defined above, and their physiologically tolerable salts.

The invention furthermore relates to compounds of the formula II

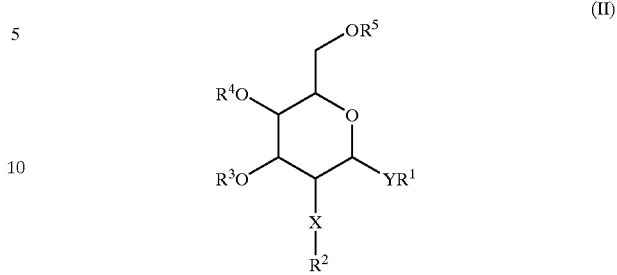

in which:

$R^1$ is a linker group which can be linked via a covalent bond to a carrier functionalized by a heteroatom, for example N, O or Cl:

$R^2$, $R^3$, $R^4$, $R^5$ independently of one another are a protective group customary in sugar chemistry;

Y is O or S, preferably S;

X is O or N, preferably O.

Protective groups customary in sugar chemistry are, for example, those such as are described, for example, in T. W. Greene, P. G. Wuts "Protective Groups in Organic Synthesis", 2nd Edition, Wiley/New York, 1991.

Suitable protective groups for compounds of the formula II are, for example, silyl protective groups, e.g. TBDPS; alkoxyalkyl groups, e.g. ethoxyethyl; allyl groups; acyl groups such as acetyl or benzoyl; acetals and ketals such as isopropylidene or optionally substituted benzylidene.

Preferred compounds of the formula II are those in which the radicals $R^2$, $R^3$, $R^4$ and $R^5$ are not all the same protective group.

Preferred compounds of the formula II are furthermore those in which only two of the radicals $R^2$, $R^3$, $R^4$, $R^5$ are an identical protective group.

Very particularly preferred compounds of the formula II are those in which the radicals $R^2$, $R^3$, $R^4$, $R^5$ are each a different protective group.

Preferred compounds of the formula II are also those which have an orthogonal protective group pattern with protective groups from the following different classes:

base-labile protective groups, such as the acetate or benzoyl group;

acid-labile protective groups, such as acetal- or ketal-like protective groups such as the ethoxyethyl group;

fluoride-labile protective groups, such as the tert-butyidimethylsilyl or tert-butyidiphenylsilyl group;

a protective group removable by transition metal catalysis, such as the allyl group;

sulfur-containing protective groups, such as in the linker system.

The invention also relates to compounds of the formula II, in which:

$R^5$ is a linker group which can be linked via a covalent bond to a carrier functionalized by a heteroatom, for example N, O or Cl;

$R^1$, $R^2$, $R^3$, $R^4$ independently of one another are a protective group customary in sugar chemistry;

Y is S or O, preferably S;

X is O or N, preferably O.

The invention also relates to compounds of the formulae IIa, IIb and IIc

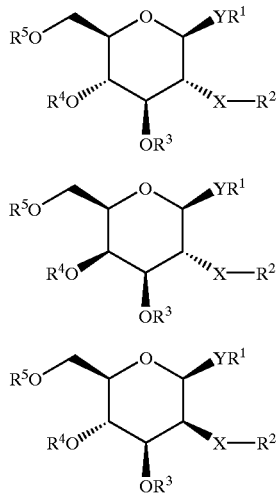

in which:
Y is S or O, preferably S;
X is O or N, preferably O;
$R^1$ is a linker group which can be linked via a covalent bond to a carrier functionalized by a heteroatom, for example N, O or Cl;
$R^2$ in the case in which X is equal to 0, is a base-labile protective group such as, for example, acetyl or benzoyl;
in the case in which X is equal to N, is a base-labile protective group such as, for example, a phthaloyl protective group, or DDE (1-(4,4-dimethyl-2,6-dioxocyclohexylidene-ethyl) or NDE (2-acetyl4-nitroindan-1,3-dione);
$R^3$ is an allyl protective group;
$R^4$ is an acid-labile protective group, such as acetal- or ketal-like protective groups, for example ethoxyethyl or SEM (2-(trimethylsilyl)ethoxymethyl);
$R^5$ is a suitable silyl protective group, such as, for example, tert-butyldimethylsilyl or tert-butyldiphenylsilyl.

In general, suitable silyl protective groups for $R^5$ are fluoride-labile protective groups, which are more stable, i.e. more difficult to remove, than a trimethylsilyl radical.

The invention also relates to compounds of the formula IIa, in which $R^4$ and $R^5$ together are an acetal- or ketal-like protective group such as, for example, isopropylidene or benzylidene and the other radicals X, Y, $R^1$, $R^2$ and $R^3$ are as defined above.

The invention additionally relates to compounds of the formula IIb, in which $R^3$ and $R^4$ together are an acetal- or ketal-like protective group such as, for example, isopropylidene or benzylidene and the other radicals X, Y, $R^1$, $R^2$ and $R^5$ are as defined above.

A suitable linker group $R^1$ or $R^5$ is, for example, a group of the formula III

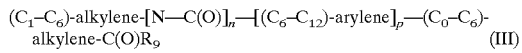

in which n and p are 0 or 1, where p and n cannot simultaneously be 1;

$R^9$ is $OR^{10}$ or $NR^{11}R^{11}$, where
$R^{10}$ is H, $(C_1-C_6)$-alkyl, $(C_1-C_6)$-alkyl-$(C_6-C_{12})$-aryl, and
$R^{11}$ independently of one another is H, $(C_1-C_6)$-alkyl, $(C_1-C_6)$-alkyl-$(C_6-C_{12})$-aryl or a polymeric solid support.

Preferred compounds of the formula I or II are also those in which $R^2$ and $R^3$ together, or $R^3$ and $R^4$ together or $R^4$ and $R^5$ together form a benzylidene radical or isopropylidene radical and the other radicals are as defined above.

Preferred compounds of the formula I and formula II are furthermore those in which the monosaccharide structure is a glucose unit, a galactose unit or a mannose unit.

The compounds of the formula II and of the formula IIa, IIb or IIc are valuable intermediates for the preparation of compounds of the formula I.

$(C_1-C_6)$-Aryl is understood, for example, as meaning phenyl, naphthyl or biphenyl.

Alkyl, alkenyl, alkynyl, alkylene and radicals derived therefrom such as, for example, alkoxy can be straight-chain or branched, those branched radicals being preferred in which the branching site is not directly situated on the linkage site to the monosaccharide structure.

Halogen is preferably fluorine, chlorine or bromine.

A heteroaryl radical within the meaning of the present invention is the radical of a monocyclic or bicyclic $(C_3-C_9)$-heteroaromatic which contains one or two N atoms and/or an S or an O atom in the ring system. For the term "heteroaromatic", see Garrat, Vollhardt, Aromatizität [Aromaticity], Stuttgart 1973, pages 131–153. Examples of suitable heteroaryl radicals are the radicals of thiophene, furan, benzo[b]thiophene, benzofuran, pyrrole, imidazole, pyrazole, pyridine, pyrazine, pyrimidine, pyridazine, indole, quinoline, isoquinoline, oxazole, isoxazole, thiazole, isothiazole, isobenzofuran, indolizine, isoindole, indazole, phthalazine, naphthyridine, quinoxaline, quinazoline, cinnoline and furazan.

As indicated above, aryl, alkyl, heteroaryl and radicals derived therefrom can be monosubstituted or, if chemically possible, alternatively polysubstituted.

Suitable polymeric solid supports are, for example, crosslinked polystyrenes (e.g. aminomethylpolystyrene (AMPS) or Tentagel.

If not stated otherwise, chiral centers can be present in the R or in the S configuration. The invention relates both to the optically pure compounds and to mixtures of stereoisomers such as mixtures of enantiomers and mixtures of diastereomers.

Suitable salts are, in particular, alkali metal and alkaline earth metal salts, salts with physiologically tolerable amines and salts with inorganic or organic acids such as, for example, HCl, HBr, $H_2SO_4$, maleic acid, fumaric acid.

The abovementioned compounds of the formulae I and II and IIa, IIb or IIc respectively are derivatives of tetrahydropyran which can be synthesized rapidly and in automated form in good yields and high purities on a solid phase with the aid of the combinatorial method described here.

Compounds of the formula I can be prepared, for example, with the aid of intermediates of the formula II which have an orthogonal protective group pattern with one or preferably a number of protective groups from the following different classes:
  base-labile protective groups, such as the acetate or benzoyl group;
  acid-labile protective groups, such as acetal- or ketal-like protective groups such as the ethoxyethyl group;
  fluoride-labile protective groups, such as the tert-butyldimethylsilyl or tert-butyldiphenylsilyl group;

a protective group which can be removed by transition metal catalysis, such as the allyl group;

sulfur-containing protective groups, such as in the linker system.

The invention thus relates to a process for the preparation of compounds of the formula I

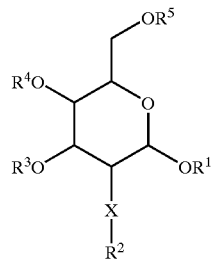

(I)

and their physiologically tolerable salts, in which:

$R^1$, $R^2$, $R^3$, $R^4$, $R^5$ independently of one another are
1. hydrogen;
2. $(C_1-C_{12})$-alkyl;
3. $(C_2-C_8)$-alkenyl;
4. $(C_2-C_8)$-alkynyl;
5. $(C_1-C_6)$-alkylene-$(C_3-C_{10})$-cycloalkyl;
6. $(C_0-C_6)$-alkylene-$(C_6-C_{12})$-aryl; preferably phenyl or benzyl;
7. $(C_1-C_6)$-alkoxy;
8. $(C_0-C_6)$-alkylene-CO—$R^8$;
9. $(C_1-C_6)$-alkylene-$(C_1-C_9)$-heteroaryl;
10. carbamoyl;
11. —C(O)NR$^6$R$^7$;
12. —C(O)OR$^6$;
13. a radical defined as in 2.-12., which is mono-, di- or polysubstituted in the alkyl moiety and/or aryl or heteroaryl moiety by a radical from the group consisting of $(C_1-C_6)$-alkyl, $NO_2$, CN, halogen, $CF_3$ or $(C_1-C_6)$-alkoxy;
14. a radical defined as in 6. and 9., which is substituted in the aryl or heteroaryl moiety by one, two or more halogen atoms; or $R^2$ and $R^3$ together or $R^3$ and $R^4$ together or $R^4$ and $R^5$ together are $(C_1-C_3)$-alkylene which can be substituted by 1 or 2 $(C_1-C_3)$-alkyl radicals or optionally substituted $(C_6-C_{12})$-aryl radicals;

$R^6$ and $R^7$ independently of one another are:
1. hydrogen;
2. $(C_1-C_{12})$-alkyl;
3. $(C_2-C_8)$-alkenyl;
4. $(C_2-C_8)$-alkynyl;
5. $(C_1-C_6)$-alkylene-$(C_3-C_{10})$-cycloalkyl;
6. $(C_1-C_6)$-alkylene-$(C_6-C_{12})$-aryl; preferably benzyl;
7. $(C_2-C_6)$-alkyloxy;
8. $(C_0-C_6)$-alkylene-CO—$R^8$;
9. $(C_1-C_6)$-alkylene-$(C_1-C_9)$-heteroaryl;
10. $(C_0-C_6)$-alkylene-$(C_1-C_6)$-alkoxy;
11. $(C_3-C_{10})$-cycloalkyl;
12. $(C_6-C_{12})$-aryl, preferably phenyl;

$R^8$ is hydrogen, $(C_1-C_6)$-alkyl, $(C_6-C_{12})$-aryl or OR$^{12}$;
$R^{12}$ is hydrogen, $(C_1-C_6)$-alkyl or $(C_6-C_{12})$-aryl; and
X is N or O; by
a) introduction of a suitable, preferably sulfur-containing linker on the anomeric center of an unprotected, partially orthogonally protected or completely orthogonally protected monosaccharide derivative of the formula

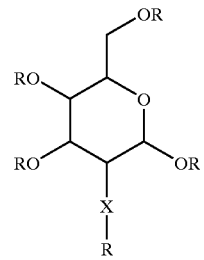

in which R in each case independently of one another is hydrogen or a protective group customary in sugar chemistry; and X is O or N, preferably O;

b) reaction of a compound linker-bonded in this way, to give compounds of the formula II

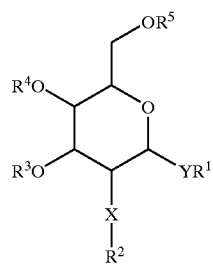

(II)

in which $R^1$ is a linker group which can be linked via a covalent bond to a support functionalized by a heteroatom, for example N, O or Cl, and $R^2$, $R^3$, $R^4$, $R^5$ independently of one another are a protective group customary in sugar chemistry, Y is O or S, preferably S and X is O or N, preferably O, by successive or simultaneous introduction of protective groups onto the functional groups —OR or —X—R, the protective groups belonging to identical or different, preferably different, orthogonal protective group classes;

c) linkage of the monosaccharide derivative of the formula II protected in this way to a polymeric solid support via the linker;

d) selective deprotection of the functional group to be derivatized on the polymeric solid support;

e) derivatization of the deprotected functional groups on the polymeric solid support, where the deprotection and subsequent derivatization of the different functional groups can be carried out selectively and also a number of equally protected functional groups can be deprotected and derivatized simultaneously;

f) removal of the derivatives bonded to the polymeric solid support, for example by activation of the sulfur on the anomeric center by bromine, and subsequent conversion of the compound activated in this way into a compound of the formula I derivatized on the anomeric center.

For the synthesis of the selectively protected monosaccharide derivatives according to formula II or IIa, IIb or IIc respectively on a solid phase, linkage to the anomeric center via a thioglycoside or an O-glycoside, in particular via a thioglycoside, is suitable. In this case, the different monosaccharides such as, for example, glucose, galactose or mannose, differ only slightly in the design of the protective groups and the sequence of their introduction. The differences in the reactivity of the functional groups and the differences associated therewith in the sequence of introduction of the different protective groups is a known problem in carbohydrate chemistry.

The synthesis strategy for the preparation of compounds of the formulae I and II is illustrated in scheme 1 by the example of the glucose derivative and is also transferable to other monosaccharides such as, for example, galactose (see scheme 3) or mannose (see scheme 4) with the abovementioned slight variations.

Compounds of the formula I can also be prepared by carrying out the linkage of selectively protected compounds of the formula II to a polymeric solid support by means of another OH position, for example the 6 OH position, such as shown in scheme 6 by the example of galactose. The linkage of the linker via the 6-OH position is possible, for example, according to the synthesis route shown in scheme 5.

Bonding of a Glycosaccharide to the Support Material (Scheme 1)

Reaction of the known 3–0-allyl-protected glucose P-acetate 3 (K. Takeo et al., Carbohydrate Research 133, 1984, 275) with the succinimide linker 2 prepared from 1 leads to compound 4. The β-configured thioglycoside 7 can be prepared analogously from the N-acylated cysteamine 6 by reaction with 3 under $BF_3$ catalysis. The deacetylation of 4 and 7 affords 8 homogeneously. Silylation on the C-6 hydroxyl group 9 and introduction of the ethoxyethyl protective group affords 10. Hydrolysis of the imide structure in 10 and coupling of the resulting acid 11 to a suitable support such as, for example, aminomethylpolystyrene affords the resin 12 loaded with the protected monosaccharide.

Reaction on the Solid Phase (see Scheme 2)

The removal and reaction of the protected monosaccharide 12 on the solid phase to give compounds of the formula I (13) is shown by way of example in scheme 2. The C-2 hydroxyl function is deacetylated by reaction with hydrazine, the hydroxyl function can then be activated by reaction with potassium tert-butoxide or phosphazene as a base (R. Schwesinger, H. Schlemper, Angew. Chem. 99, 1987, 1212–1214). The activated derivative is trapped by means of electrophiles. An analogous reaction can be carried out in the case of a C-2 amino function. The protective group used here is, for example, the Fmoc group, which can be removed by piperidine.

The removal of the allyl ether on the C-3 hydroxyl group is carried out under zirconocene catalysis (E. Negishi, Tetrahedron Lett. 1986, 27, 2829–2832; E. Negishi, Synthesis, 1988, 1–19). The functionalization is carried out analogously to the manner described above. By this means, the use of strong acids, such as would be necessary in other removal methods familiar to the person skilled in the art, can be avoided and the orthogonality to the other protective groups is guaranteed.

Alternatively to the base-catalyzed functionalization, the allyl ether protective group can be converted into a propyl group by reduction with diimine (see Hüning, H. R. Müller, W. Thier, Angew. Chem. 1965, 77, 368–377). The $C_4$ hydroxyl function can be removed by transacetalization in an analogous manner to that used in the case of THP acetals (cf. E. J. Corey, H. Niwa, J. Knolle, J. Am. Chem. Soc. 1978, 100, 1942–1943). The functionalization is carried out as described above. The C-6 hydroxyl function is desilylated by reaction with fluoride ions; the reaction with electrophiles is carried out analogously to C-2.

The individual steps can be carried out in a different sequence on account of the compatibilities.

After completion of the functionalization of the various groups, the anomeric position is activated by reaction of the polymerically bonded selectively protected monosaccharide with bromine/di-tert-butylpyridine. The 1-bromo derivative is converted into a derivative functionalized on the anomeric center by reaction with alcohol.

Synthesis Sequence for the Preparation of Galactose Derivatives (see Scheme 3)

Starting from galactose pentaacetate 14, the thioglycoside 16 is prepared by boron fluoride-catalyzed reaction with 15. Reaction with sodium methoxide affords 17 with deacetylation. The selective silylation of 17 takes place on the C-6 hydroxyl function. The silyl ether 18 is converted into the isopropylidene-protected derivative 19 using dimethoxypropane. Acetylation by reaction with acetic anhydride affords 20. After removal of the isopropylidene protective group, the dihydroxy compound is converted into the allyl ether derivative protected on C-4 using dibutyltin oxide and allyl bromide. Introduction of the ethoxyethyl protective group affords 21. The ester is hydrolyzed with lithium hydroxide analogously to glucose.

Synthesis Sequence for the Preparation of Mannose Derivatives (see Scheme 4)

Mannose pentaacetate 22 is reacted with thiol 6 with boron trifluoride catalysis to give the thiomannoside 23. Removal of the acetate protective groups by sodium methoxide affords 24. Reaction with dimethoxybenzaldehyde affords the acetal 25. Reaction with dibutyltin oxide and allyl bromide leads to the 3-O-allyl ester. By acetylation with acetic anhydride, 26 is prepared. The removal of the ketal and subsequent selective silylation on C-6 affords a silyl ether. Introduction of the ethoxyethyl protective group affords 27. The ester in 27 is hydrolyzed with lithium hydroxide analogously to glucose.

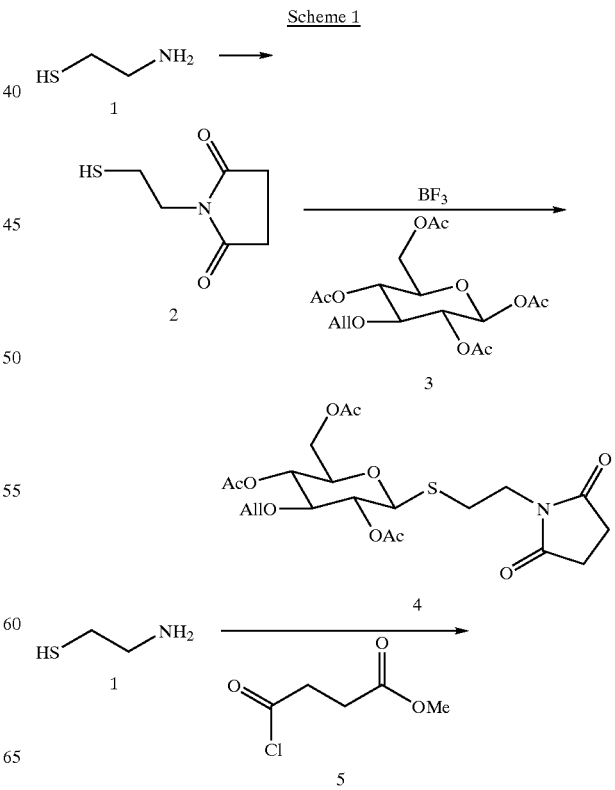

Scheme 1

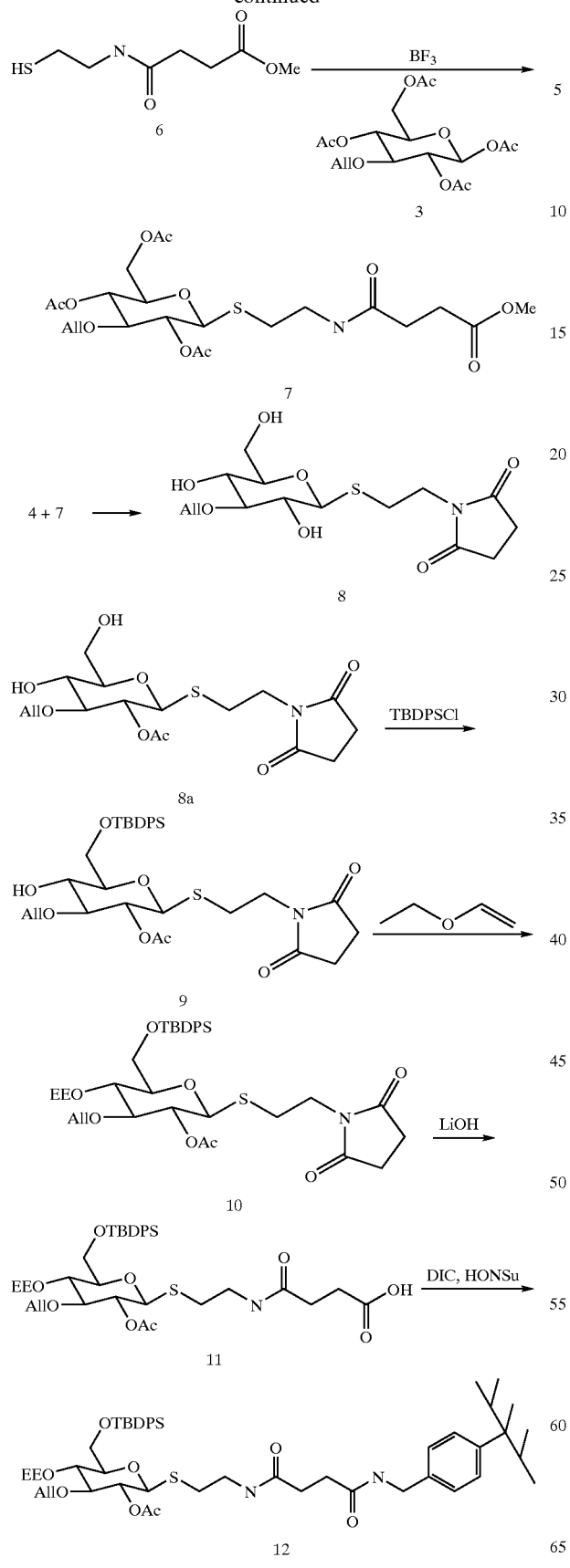
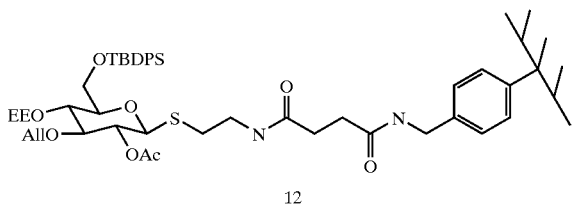
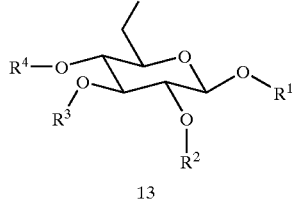
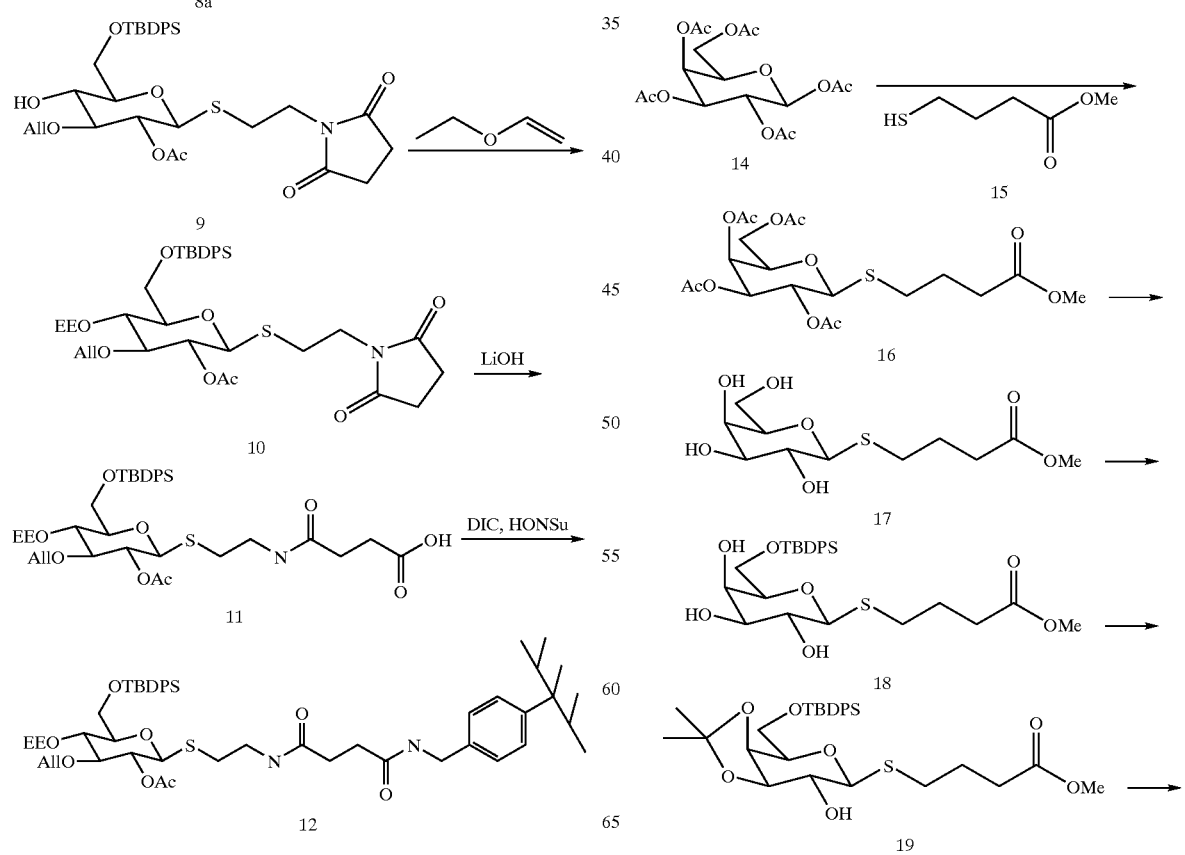

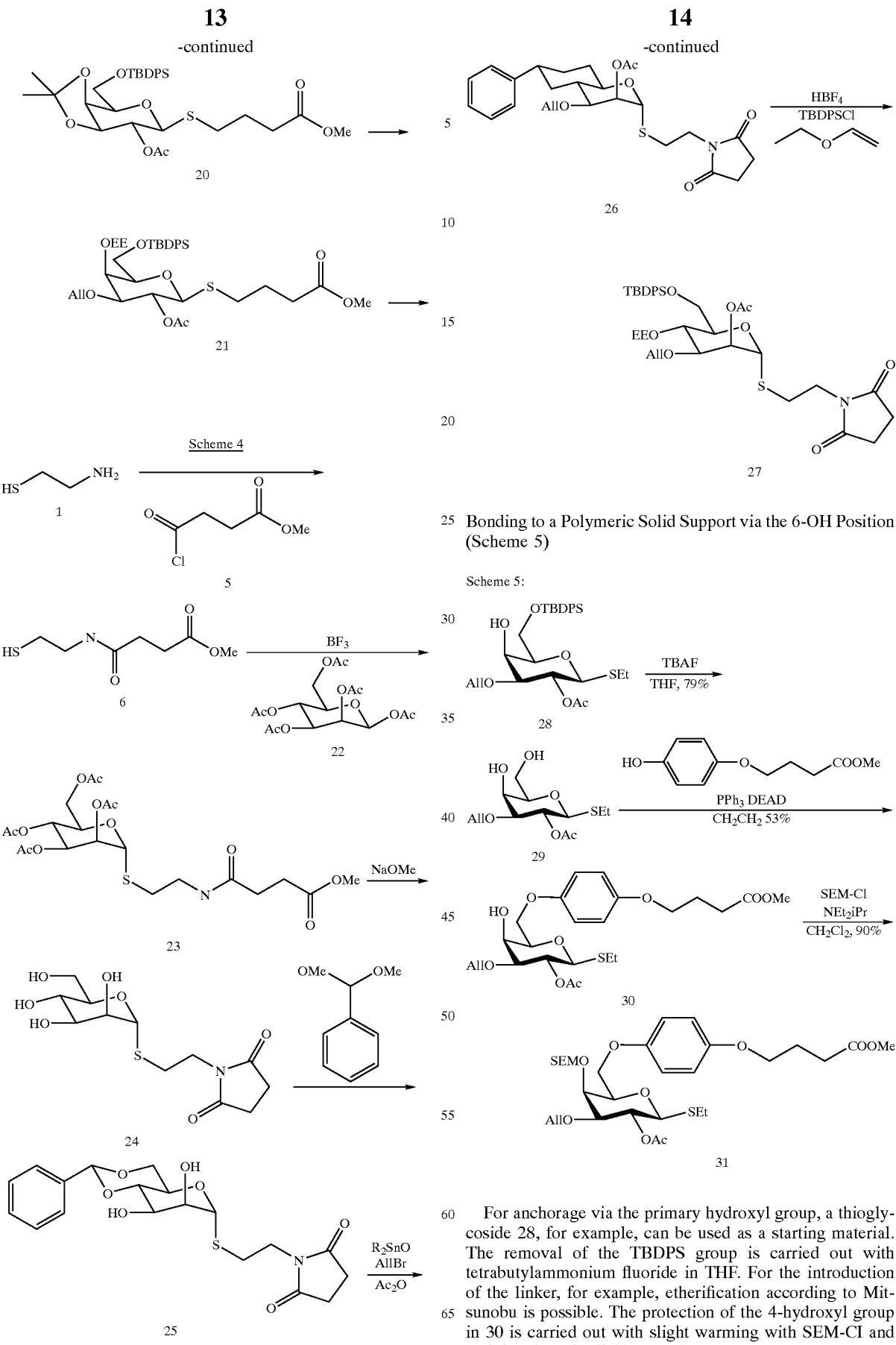

Bonding to a Polymeric Solid Support via the 6-OH Position (Scheme 5)

Scheme 5:

For anchorage via the primary hydroxyl group, a thioglycoside 28, for example, can be used as a starting material. The removal of the TBDPS group is carried out with tetrabutylammonium fluoride in THF. For the introduction of the linker, for example, etherification according to Mitsunobu is possible. The protection of the 4-hydroxyl group in 30 is carried out with slight warming with SEM-Cl and Hujnig's base in dichloromethane.

Synthesis Sequence for the Preparation of Galactose Derivatives Which are Bonded to a Polymeric Solid Support via the 1-OH Group (Scheme 6)

After binding of the glycoside to the solid polymeric support, the 1-OH group and the 2-OH group are first to be functionalized in the desired sequence, then the SEM group and the allyl ether are removed successively and the 3- and 4-positions are derivatized. The detachment of the solid polymer, for example using cerium ammonium nitrate (CAN), and the functionalization of the 6-OH function are then carried out.

Scheme 6:

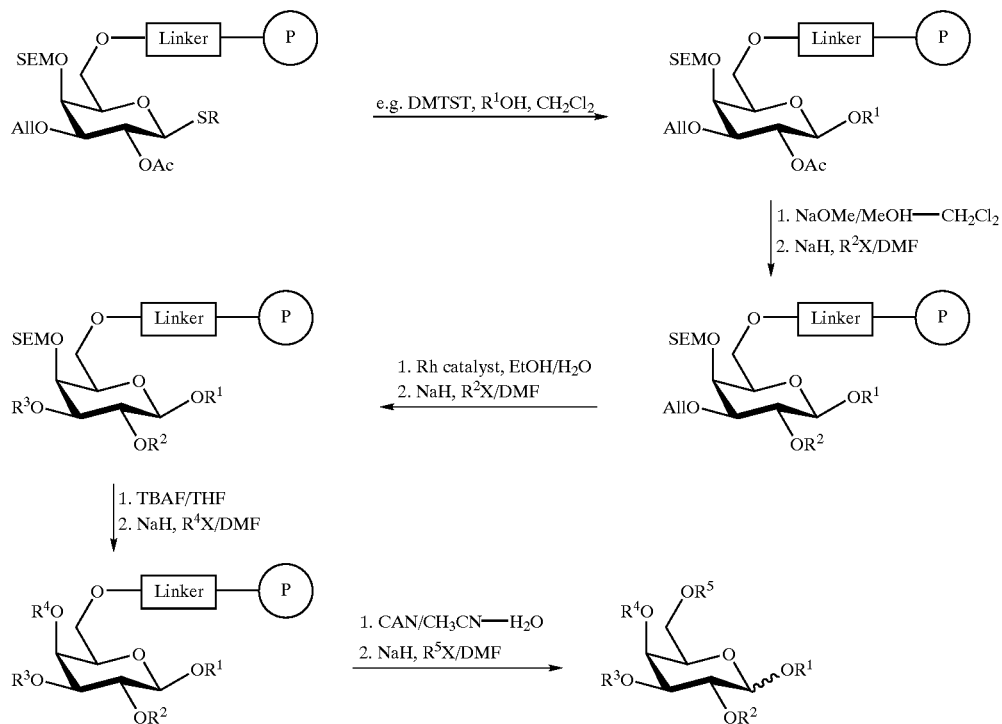

R = H  19
  = Me 32

On account of their polyvalency and their defined spatial arrangement, the compounds of the formulae II, IIa, IIb and IIc are suitable as structural units for biological mimetics, for example peptide mimetics, and are a useful aid for the preparation and/or discovery of new lead structures and the identification of potential active compounds.

Coupling of a methyl galactosylmercaptobutyrate to an amino-funtionalized polymeric support via the 1-position (scheme 7)

Scheme 7

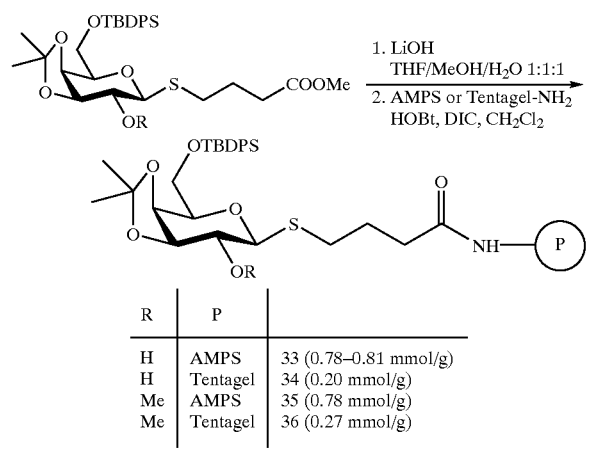

| R  | P        |                   |
|----|----------|-------------------|
| H  | AMPS     | 33 (0.78–0.81 mmol/g) |
| H  | Tentagel | 34 (0.20 mmol/g)  |
| Me | AMPS     | 35 (0.78 mmol/g)  |
| Me | Tentagel | 36 (0.27 mmol/g)  |

The compounds of the formula I prepared with the aid of the compounds of the formula II, IIa, IIb or IIc have potential diagnostic and/or pharmacological action in various forms of disorder. Autoimmune diseases and carcinomatous disorders, for example, may be mentioned.

On account of their potentially valuable pharmacological properties, the compounds according to the present invention and their physiologically tolerable salts are very highly suitable for use as therapeutics in mammals, in particular man.

The present invention therefore furthermore relates to a pharmaceutical comprising one or more compounds of the formula I and/or its pharmacologically tolerable salts, and their use for the production of a pharmaceutical for the therapy or prophylaxis of autoimmune diseases, for example rheumatism or carcinomatous disorders.

The pharmaceuticals are particularly suitable for the treatment of acute and chronic inflammation, which can be characterized pathophysiologically by a disorder of the cell circulation, for example of lymphocytes, monocytes and neutrophilic granulocytes. These include autoimmune disorders such as acute polyarthritis, rheumatoid arthritis and insulin-dependent diabetes (diabetes mellitus IDDM), acute and chronic transplant rejection, shock lung (ARDS, adult respiratory distress syndrome), inflammatory and allergic skin disorders such as, for example, psoriasis and contact eczema, cardiovascular disorders such as myocardial infarct, reperfusion injuries after thrombolysis, angioplasty or by-pass operations, septic shock and systemic shock. A further potential indication is the treatment of metastasizing tumors. Moreover, these pharmaceuticals, which are stable in the acid medium of the stomach, can be employed for the antiadhesive therapy of Helicobacter pylori and related microorganisms, if appropriate also in combination with antibiotics. Therapy of the cerebral form of malaria is furthermore conceivable with the aid of these pharmaceuticals.

Further potential application possibilities of the pharmaceuticals are in the treatment of metabolic disorders, such as diabetes and arteriosclerosis, of disorders of the cardiovascular and the central nervous system and of disorders of bone metabolism, and in their use as an antiinfective or as a pharmaceutical having immunomodulating properties.

Pharmaceuticals which contain a compound of the formula I can be administered here orally, parenterally, intravenously, rectally or by inhalation, the preferred administration being dependent on the particular course of the disorder. The compounds I can be administered here on their own or together with pharmaceutical excipients, to be specific both in veterinary and in human medicine.

The person skilled in the art is familiar on the basis of his expert knowledge with the auxiliaries which are suitable for the desired pharmaceutical formulation. In addition to solvents, gel-forming agents, suppository bases, tablet auxiliaries, and other active compound carriers, it is possible to use, for example, antioxidants, dispersants, emulsifiers, antifoams, flavor corrigents, preservatives, solubilizers or colorants.

For an oral administration form, the active compounds are mixed with the additives suitable therefor, such as vehicles, stabilizers or inert diluents, and brought into the suitable administration forms, such as tablets, coated tablets, hard gelatin capsules, aqueous, alcoholic or oily solutions, by the customary methods. Inert carriers which can be used are, for example, gum arabic, magnesia, magnesium carbonate, potassium phosphate, lactose, glucose or starch, in particular corn starch. In this case, preparation can take place both as dry and as moist granules. Suitable oily vehicles or solvents are, for example, vegetable or animal oils, such as sunflower oil or cod liver oil.

For subcutaneous or intravenous administration, the active compounds, if desired with the substances customary therefor, such as solubilizers, emulsifiers or further excipients, are brought into solution, suspension or emulsion. Suitable solvents are, for example: water, physiological saline solution or alcohols, e.g. ethanol, propanol, glycerol, in addition also sugar solutions such as glucose or mannitol solutions, or alternatively a mixture of the various solvents mentioned.

Suitable pharmaceutical formulations for administration in the form of aerosols or sprays are, for example, solutions, suspensions or emulsions of the active compound of the formula I in a pharmaceutically acceptable solvent, such as, in particular, ethanol or water, or a mixture of such solvents.

If required, the formulation can also additionally contain other pharmaceutical excipients such as surfactants, emulsifiers and stabilizers and also a propellant. Such a preparation customarily contains the active compound in a concentration of approximately 0.1 to 10, in particular from approximately 0.3 to 3, % by weight.

The dose of the active compound of the formula I to be administered and the frequency of administration depend on the potency and duration of action of the compounds used; in addition also on the nature and severity of the disease to be treated and on the sex, age, weight and individual responsiveness of the mammal to be treated.

The daily dose can be administered either by single administration in the form of an individual dose unit or else of a number of small dose units and also by multiple administration of subdivided doses at specific intervals. The daily dose to be administered can moreover be dependent on the number of receptors expressed during the course of the disease. It is conceivable that in the initial stage of the disease only a few receptors are expressed on the cell surface and accordingly the daily dose to be administered is lower than in severely ill patients.

On average, the daily dose of a compound of the formula I in a patient approximately 75 kg in weight is at least 0.001 mg/kg, preferably at least 0.01 mg/kg, to at most 10 mg/kg, preferably at most 1 mg/kg, of body weight.

Leukocyte Adhesion—Testing of the Activity of the Compounds According to the Invention in vivo In inflammatory processes and other conditions activating cytokines, tissue destruction by immigrating or microcirculation-blocking leukocytes plays a crucial role. The phase which is first and crucial for the further disease process is the activation of leukocytes within the blood stream, in particular in the pre- and postcapillary area. In this case, after the leukocytes have left the axial flow of the blood, a first attachment of the leukocytes to the vascular inner wall, i.e. to the vascular endothelium, occurs. All subsequent leukocyte effects, i.e. the active diffusion through the vascular wall and the subsequent orientated migration into the tissue, are secondary reactions (Harlan, J. M., Leukocyte-endothelial interaction, Blood 65, 513–525, 1985). This receptor-mediated interaction of leukocytes and endothelial cells is regarded as an initial sign of the inflammatory process. In addition to the adhesion molecules already physiologically expressed, under the action of inflammatory mediators (leukotrienes, PAF) and cytokines (TNF-alpha, interieukines) the temporally graduated, massive expression of adhesion molecules on the cells occurs. They are at present divided into three groups: 1. immunoglobulin gene superfamily, 2. integrins and 3. selectins. While the adhesion between molecules of the Ig superfamily and the protein-protein bonds proceeds, lectin-carbohydrate bonds are prominent in the cooperation between selectins (Springer, T. A., Adhesion receptors of the immune system. Nature 346, 425–434, 1990; Huges, G., Cell adhesion molecules—the key to an universal panacea, Scrips Magazine 6, 30–33, 1993; Springer, T. A., Traffic signals for lymphocyte recirculation and leukocyte emigration; The multistep paradigm, Cell 76, 301–314, 1994).

The Activity of the Compounds According to the Invention in vivo can be Tested According to the Following Method:

The induced adhesion of leukocytes is quantified in the mesenterium of the rat using an intravital microscopic investigation technique (Atherton A. and Born G. V. R., Quantitative investigations of the adhesiveness of circulating polymorphonuclear leukocytes to blood vessel walls. J. Physiol. 222, 447–474, 1972; Seiffge, D. Methoden zur Untersuchung der Rezeptor-vermittelten Interaktion zwischen Leukozyten und Endothelzellen im Entzündungsgeschehen [Methods for the investigation of receptor-mediated interaction between leukocytes and endothelial cells in the inflammation process], in: Ersatz- und Ergätnzungsmethoden . zu Tierversuchen in der biomedizinischen Forschung [Replacement and supplementary methods for animal experiments in biomedical research], Schöffl, H. et al., (Ed.) Springer, 1995 (in press)). Under inhalation ether anesthesia, prolonged anesthesia is initiated by intramuscular injection of urethane (1.25 mg/kg of BW). After exposure of vessels (femoral vein for the injection of substances and carotid artery for blood pressure measurements), catheters are tied into these. The appropriate transparent tissue (mesenterium) is then exposed by standard methods known in the literature and laid out on the microscope stage and covered with a layer of paraffin oil at 37° C. (Menger, M. D. and Lehr, H., A. Scope and perspectives of intravital microscopy-bridge over from in vitro to in vivo, Immunology Today 14, 519–522, 1993). The test substance is administered i.v. to the animal (10 mg/kg). The experimental increase in blood cell adhesion is induced by means of cytokine activation by systemic administration of lipopolysaccharide (LPS, 15 mg/kg) 15 minutes after administration of test substance (Foster S. J., McCormick L. M., Ntolosi B. A. and Campbell D., Production of TNF-alpha by LPS-stimulated murine, rat and human blood and its pharmacological modulation, Agents and Actions 38, C77–C79, 1993, 18.01.1995). The increased adhesion of leukocytes to the endothelium caused thereby is quantified directly by vital microscopy or with the aid of fluorescent dyes. All measuring processes are carried out by video camera and stored on a video recorder. Over a period of 60 minutes, the number of rolling leukocytes, (i.e. all visible rolling leukocytes, which are slower than the flowing erythrocytes) and the number of adhering leukocytes on the endothelium (residence time longer than 5 seconds) are determined every 10 minutes. After completion of the experiment, the anesthetized animals are put to sleep without excitation in a pain-free manner by systemic injection of T61. For evaluation, the results of 8 treated animals in each case are compared (in percent) with those of 8 untreated animals (control group).

EXAMPLES

Example 1

N-(2-Thioethyl)succinimide 2

A solution of 24.2 g (0.21 mmol) of cysteamine hydrochloride 1 in 50 ml of $H_2O$ is treated with 19.7 g (0.23 mol) of $NaHCO_3$ and stirred for 45 min. It is then concentrated in vacuo and the residue is taken up in 100 ml of acetic acid. After addition of 21.3 g (0.21 mol) of succinic anhydride, the suspension is heated under reflux for 3 h. The precipitate resulting on cooling of the solution is filtered off, washed with cold acetic acid and the filtrate is freed from the solvent in vacuo. The product is purified by chromatography on silica gel using petroleum ether/ethyl acetate (1:1).

Yield: 13.0 g (38%) of colorless, amorphous solid. $R_f$=0.71 (EtOAc:HOAc=30:1 v/v), m.p.: 44–45° C. $C_6H_9NO_2S$ (159.2) Calc.: C 45.26 H 5.70 N 8.80 S 20.14; Found: C 45.16 H 5.76 N 8.71 S 20.20.

Example 2

N-[2-S-(2',4',6'-Tri-O-acetyl-3'-O-allyl-D-glucopyranosyl)thioethyl]-succinimide 4

4 ml (32 mmol) of boron trifluoride etherate in 10 ml of absol. $CH_2Cl_2$ are added dropwise to a solution of 2.0 g (5.15 mmol) of the acetate 3 and 980 mg (6.18 mmol) of N-(2-thioethyl)succinimide 2 in 55 ml of absol. $CH_2Cl_2$ cooled to 0° C. under argon. The ice cooling is then removed and the reaction is stirred further at room temp. After 16 h, the mixture is treated with 100 ml of $CH_2Cl_2$ and extracted twice with satd $NaHCO_3$ solution. The organic phase is dried over $MgSO_4$ and the solvent is removed in vacuo. The product is purified by chromatography on silica gel using petroleum ether/ethyl acetate (2:1) and the product is then reprecipitated from ethyl acetate/n-pentane. Yield: 1.71 g (75%) of colorless, amorphous solid.

$R_f$=0.27 (PE:EtOAc=1:2 v/v), $[\alpha]_D^2$=−41.8° (c 1.0, $CHCl_3$), m.p.: 108° C.

| $C_{21}H_{29}NO_{10}S$ | (487.5) | Calc.: | C 51.74 | H 6.00 | N 2.87 | S 6.58 |
|---|---|---|---|---|---|---|
| | | Found: | C 51.64 | H 6.13 | N 2.88 | S 6.50 |

200 MHz $^1$H-NMR ($CDCl_3$): [ppm]=5.80–5.61 (m 1H, $CH_2$=CH); 5.18–4.97 ($CH_2$=CH, H-2' & H4'); 4.38 (d, 1H, $J_{2,1}$=10.01 Hz, H-1'); 4.19–3.94 (m, 4H, =CH=$CH_2$, H-6a/b'); 3.79–3.50 (m, 4H, H-3', H-5' & $NCH_2$ Cya); 2.93–2.79 (m, 1H, $SCH_2$ Cya); 2.76–2.61 (m, 1H, $SCH_2$ Cya); 2.65 (s, 4H, $COCH_2$ Suc); 2.03, 2.02 (2×s, 9H, $CH_3$ Ac). 100.6 MHz-$^{13}$C-NMR ($CDCl_3$): [ppm]=176.6 ($COCH_2$); 169.1 ($COCH_3$); 134.2 ($CH_2$=CH); 116.8 ($CH_2$=CH); 83.3, 81.0, 76.3, 73.0, 71.1, 69.4 (C-1', C-2', C-3', $C_4$', C-5', =CH—$CH_2$); 62.3 (C-6'); 38.2 ($CH_2CO$ Suc); 28.0 ($NCH_2$ Cya); 27.2 ($SCH_2$ Cya); 20.8, 20.7, 20.6 ($CH_3$ Ac). The resulting α-anomer can be separated by chromatography. Yield: 0.19 g (8%), colorless oil. $R_f$=0.33 (PE:EtOAc=1.2 v/v).

Example 3

Monomethyl N-(2-Thioethyl)succinamidate 6

11.0 g (96.8 mmol) of cysteamine hydrochloride 1 are suspended in 75 ml of absol. acetonitrile under argon. 60 ml (345.0 mmol) of Hünig's base are slowly added dropwise to this with ice-cooling in an argon countercurrent.

After 5 min, 16.4 ml (130.0 mmol) of trimethylchlorosilane are added in one portion. The mixture is stirred at 0° C. for 10 min before a solution of 11.93 ml (96.8 mmol) of monomethyl succinyl chloride 5 in 20 ml of absol. acetonitrile is added dropwise. After 30 min at 0° C. and 2 h at room temp., the solution is poured into 200 ml of ice water and the product is extracted twice with 200 ml of ethyl acetate each time. The combined organic phases are washed with 30 ml of 1N HCl, 50 ml of satd $NaHCO_3$ solution and 50 ml of satd NaCl solution, dried over $MgSO_4$ and the solvent is removed in vacuo. Yield: 13.1 g (71%), weakly yellowish oil.

$R_f$=0.54 (EtOAc), $R_f$=0.58 (EtOAc:HOAc=30:1 v/v) $C_7H_{13}NO_3S$ (191.3)

| Calc.: | C 43.96 | H 6.85 | N 7.32 | S 16.76 |
|---|---|---|---|---|
| Found: | C 43.97 | H 6.78 | N 7.65 | S 16.16 |

90 MHz-$^1$H-NMR (CDCl3): [ppm] =3.62 (s, 3H, $OCH_3$); 3.37 (q, Jgem =6.26 Hz, $CH_2N$ Cya); 2.80–2.17 (m, 6H, $SCH_2$, 2×$CH_2CO$).

Example 4

Monomethyl N-[2-S-(2',4',6'-Tri-O-acetyl-3'-O-allyl-β-D-glucopyranosyl)-thioethyl]succinamidate 7

6.0 g (15.5 mmol) of 3 are dissolved in 120 ml of absol. $CH_2Cl_2$. After addition of 3.32 g (18.5 mmol) of the thiol, the solution is cooled to 0° C. under argon. A solution of 17.5 ml (139 mmol) of boron trifluoride etherate in 20 ml of absol. $CH_2Cl_2$ is slowly added dropwise to this mixture. The ice-cooling is then removed and the mixture is stirred at room temp. for 6 h. The reaction mixture is extracted twice with satd $NaHCO_3$ solution, the organic phase is separated off and dried over $MgSO_4$, and the solvent is removed in vacuo. After chromatography on silica gel using petroleum ether/ethyl acetate/HOAc (60:30:1), 6.8 g (85%) of a colorless, amorphous solid are obtained.

$R_f$=0.44 (EtOAc), $R_f$=0.51 (toluene:EtOH=4:1 v/v), m.p.: 75–77° C., $[\alpha]_D^2$=−5.3° (c 1, $CHCl_3$). $C_{22}H_{33}NO_{11}S$ (519.57)

| | | | | |
|---|---|---|---|---|
| Calc.: | C 50.82 | H 6.40 | N 2.70 | S 6.17 |
| Found: | C 50.74 | H 6.44 | N 2.76 | S 6.23 |

200 MHz-$^1$H-NMR ($CDCl_3$): [ppm]=6.33 ($t_b$, 1H, $J_{gem}$=5.13 Hz, NH); 5.80–5.61 (m, 1H, $CH_2$=CH); 5.184.87 (m, 4H, $CH_2$=CH, H-2' & H-4'); 4.38 (d, 1H, $J_{2,1}$=9.76 Hz, H-1'); 4.114.00 (m, 2H, H-6'a/b); 3.62 (s, 3H, $CO_2CH_3$); 3.59–3.41 (m, 3H, H-3', H4', H-5'); 3.38–3.24 (m, 2H, $CH_2N$ Cya); 2.89–2.51 (m, 4H, $SCH_2$ Cya & $CH_2CO_2$ Suc); 2.43 (t, 2H, $J_{gem}$=6.41 Hz, $CH_2CON$ Suc); 2.05, 2.02, 2.01 (3×s, 9H, $CH_3$ Ac).

Example 5

N-[2-S-(3'-O-Allyl-D-glucopyranosyl)thioethyl] succinimide 8

2.6 ml (2.6 mmol) of a 1M NaOMe solution in methanol are added under argon to 7.76 g (14.93 mmol) of thioglycoside 7 (crude product) dissolved in 60 ml of methanol p.a. The reaction solution is stirred at 50° C. for 12 h, neutralized (5 min) with acidic ion exchanger Amberlyst® 15, and the ionic exchanger is removed by filtration and washed with methanol. The filtrate is freed from the solvent in vacuo. After chromatography on silica gel using toluene/EtOH (4:1), 4.86 g (86%) of a colorless oil are obtained, which solidifies after some time to give a colorless, amorphous solid.

$R_f$=0.27 (toluene:EtOH=4:1 vtv), m.p.: 98–99° C., $[\alpha]_D^2$=−37.2° (c 1.0, $CHCl_3$). $CH_{15}H_{23}NO_7S$ (361.4)

| | | | | |
|---|---|---|---|---|
| Calc.: | C 49.85 | H 6.41 | N 3.88 | S 8.87 |
| Found: | C 49.89 | H 6.62 | N 3.86 | S 8.83 |

400 MHz $^1$H-NMR ($CDCl_3$): [ppm]=5.98–5.88 (m, 1H, $CH_2$=CH); 5.27 (d, 1H, $J_{vic,trans}$=17.32 Hz, $CH_2$=CH); 5.16 (d, 1H, $J_{vic,cis}$=10.27 Hz, $CH_2$=CH); 4.43 (dd, 1H, $J_{gem}$=12.62 Hz, $J_{vic}$=5.58 Hz, =CH—$CH_2$); 4.32 (d, 1H, $J_{2,1}$=9.69 Hz, H-1'); 4.26 (dd, 1H, $J_{gem}$=12.91 Hz, $J_{vic}$=5.87 Hz, =CH—$CH_2$); 3.89–3.86 (m, 1H, H-6'a); 3.79–3.68 (m, 3H, H-2', H4' & H-6'b); 3.54 (t, 1H, $J_{2,3}$=$J_{4,3}$=9.25 Hz, H-3'); 3.44–3.34 (m, 2H, $CH_2N$ Cya); 3.29 (t, $J_{3,4}$=$J_{5,4}$=8.51 Hz, H-5'); 3.09, 3.03 (2×$s_b$, 2H, OH); 2.97–2.90 (m, 1H, $SCH_2$ Cya); 2.83–2.75 (m, 1H, $SCH_2$ Cya); 2.71 (s, 4H, $CH_2CO$ Suc).

Example 6

N-[2-S-(2'-O-Acetyl-3'-O-allyl-D-glucopyranosyl) thioethyl]succinimide 8a

Variant 1: By Deacetylation of the Succinimide 4

1.15 g (2.36 mmol) of thioglycoside are cooled to 0° C. under argon in 25 ml of methanol p.a. 13 mg (0.24 mmol) of NaOMe are added to the resulting suspension. After about 2 h, the precipitate dissolves and after a further 45 min the reaction is ended by addition of acidic ion exchanger Amberlyst® 15. The mixture is filtered, the ion exchanger is washed with methanol and the combined filtrates are freed from the solvent in vacuo. After chromatography on silica gel using toluene/EtOH (4:1), 895 mg (94%) of a colorless, amorphous solid are obtained.

Variant 2: By Deacetylation of the Acyclic Derivative 7

A solution of 2.6 g (5.0 mmol) of the glycoside in 50 ml of methanol p.a. is treated with 27.0 mg (0.5 mmol) of NaOMe at −15° C. After 1 h, no conversion can be detected by thin-layer chromatography, so a further 27 mg (0.5 mmol) of NaOMe are added and the temperature is increased to 0° C. As the formation of a further, more polar product (deacetylation in the 2-position) can be detected in the thin-layer chromatogram, the reaction is terminated after 6 h by addition of acidic ion exchanger Amberlyst® 15. The solution is filtered, the ion exchanger is washed with methanol and the solvent is removed from the combined filtrates in vacuo. The product is purified by chromatography on silica gel using toluene/EtOH (4:1). Yield: 1.2 g (90%), colorless, amorphous solid.

| | | | | | |
|---|---|---|---|---|---|
| $C_{17}H_{25}NO_8S$ (403.5) | Calc.: | C 50.61 | H 6.25 | N 3.47 | S 7.95 |
| | Found: | C 49.85 | H 6.59 | N 3.87 | S 7.95 |

200 MHz-$^1$H-NMR ($CDCl_3$): [ppm]=5.92–5.73 (m, 1H, $CH_2$=CH); 5.24–5.08 (m, 2H, $CH_2$=CH); 4.86 (t, 1H, $J_{1,2}$=$J_{3,2}$=9.52 Hz, H-2'); 4.37 (d, 1H, $J_{2,1}$=7.76 Hz, H-1'); 4.25–4.08 (m, 2H, =CH—$CH_2$); 3.91–3.55 (m, 4H, H-3', H-4', H-6'a/b); 3.49–3.34 (m, 4H, H-5', $CH_2N$ Cya & OH); 2.99–2.71 (m, 2H, $SCH_2$ Cya); 2.68 (s, 4H, $CH_2CO$ Suc); 2.04 (s, 3H, $CH_3$ Ac).

Example 7

N-[2-S-(2'-O-Acetyl-3'-O-allyl-6'-O-tert-butyldiphenylsilyl-D-glucopyranosyl)-thioethyl] succinimide 9

1.0 g (2.48 mmol) of the succinimide 8a is dissolved in 20 ml of absol. $CH_2Cl_2$, treated with 583 mg (10.7 mmol) of imidazole, 0.74 ml (3.57 mmol) of tert-butydiphenylchlorosilane and a spatula-tipful of DMAP and stirred at room temp. After 2 h, the mixture is diluted with 100 ml of $CH_2Cl_2$ and extracted with 50 ml of 1N HCl and satd NaCl solution. The organic phase is dried over $MgSO_4$ and the solvent is removed in vacuo. After chromatography on silica gel using petroleum ether/ethyl acetate (1:1), 1.43 g (90%) of a colorless solid are obtained.

$R_f$=0.47 (PE:EtOAc=1:1 v/v), m.p.: 39–40° C.

| | | | | | |
|---|---|---|---|---|---|
| $C_{33}H_{43}NO_8SSi$ (641.9) | Calc.: | C 61.75 | H 6.75 | N 2.18 | S 5.00 |
| | Found: | C 61.58 | H 7.12 | N 2.17 | S 4.81 |

400MHz-$^1$H-NMR ($CDCl_3$): [ppm]=7.67–7.65 (m, 4H, PhSi); 7.42–7.33 (m, 6H, PhSi); 5.89–5.82 (m, 1H, CH$_2$=CH); 5.24 (dd, 1H, J$_{vic,trans}$=17.22 Hz, J$_{gem}$=1.58 Hz, CH$_2$=CH); 5.14 (d, 1H, J$_{vic,cis}$=10.41 Hz, CH$_2$=CH); 4.91 (t, 1H, J1.2=J$_{3,2}$=9.56 Hz, H-2'); 4.42 (d, 1H, J$_{2,1}$=9.97 Hz, H-1'); 4.25–4.14 (m, 2H, =CH—CH$_2$); 3.90 (d, 2H, J=4.51 Hz, H-6'a/b); 3.76 (t, 1H, J$_{3,4}$=J$_{5,4}$=9.21 Hz, H-4'); 3.70–3.63 (m, 2H, H-3' & H-5'); 3.47–3.41 (m, 2H, CH$_2$N Cya); 2.89 (s, 1H, OH); 2.87–2.81 (m, 1H, SCH$_2$ Cya); 2.75–2.62 (m, 1H, SCH$_2$ Cya); 2.61 (s, 4H, CH$_2$CO Suc);2.07 (s, 3H, CH$_3$ Ac); 1.01 (s, 9H, CH$_3$ tBuSi).

Example 8

N-[2-S-(2'-O-Acetyl-3'-O-allyl-6'-O-tert-butyldiphenylsilyl-4'-O-(1"-(R/S )-ethoxyethyl)-D-glucopyranosyl)thioethyl]succinimide 10

A solution of 1.26 g (1.96 mmol) of the succinimide 9 in 20 ml of absol. CH$_2$Cl$_2$ is treated with 0.94 ml (9.80 mmol) of ethyl vinyl ether and 246 mg (0.98 mmol) of pyridinium toluene-4-sulfonate and stirred at room temp. After 3 h, the reaction solution is diluted with 50 ml of CH$_2$Cl$_2$ and extracted twice with 30 ml of satd NaHCO$_3$ solution each time. The organic phase is dried over MgSO$_4$ and the solvent is removed in vacuo.

Yield: 1.37 g (98%), colorless oil. R$_f$=0.59 (PE:EtOAc= 1:1 v/v),

| C$_{37}$H$_{51}$NO$_9$SSi | (714.0) | Calc.: | C 62.25 | H 7.20 | N 1.96 | S 4.49 |
|---|---|---|---|---|---|---|
| | | Found: | C 61.61 | H 6.86 | N 2.00 | S 5.06 (crude product) |

400MHz-$^1$H-NMR (CDCl$_3$): [ppm]=7.70–7.65 (m, 4H, PhSi); 7.40–7.33 (m, 6H, PhSi); 5.85–5.81 (m, 1H, CH$_2$=CH); 5.25–5.08 (m, 2H, CH$_2$=CH); 4.93–4.87 (m, 1H, H-2'); 4.80 (q, 0.5H, J$_{gem}$=5.29 Hz, CHCH$_3$ EE); 4.65 (q, 0.5H, J$_{gem}$=5.28 Hz, CHCH$_3$ EE); 4.42 (d, 1H, J$_{2,1}$=9.68 Hz); 4.23 (dd, 1H, J$_{gem}$=12.62 Hz, J$_{vic}$=5.57 Hz, =CH—CH$_2$); 4.16 (dd, 1H, J$_{gem}$=12.62 Hz, J$_{vic}$=5.58 Hz, =CH—CH$_2$); 3.90–3.86 (m, 2H, H-6'a/b); 3.75 (t, 1H, J$_{3,4}$=J$_{5,4}$= 9.25 Hz, H4'); 3.68–3.58 (m, 3H, H-3' & CH$_2$N Cya); 3.52–3.41 (m, 3H, H-5' & CH$_3$CH$_2$O EE); 2.86–2.81 (m, 1 Hz, SCH$_2$ Cya); 2.74 (m, 1H, SCH$_2$ Cya); 2.60 (s, 4H, CH$_2$CO Suc); 2.06 (s, 3H, CH$_3$ Ac); 1.28–1.11 (m, 4.5H, CHCH$_3$ & CH$_3$CH$_2$O EE); 1.00 (s, 9H, CH$_3$ tBuSi); 0.89 (t, 1.5H, J=6.90 Hz, CH$_3$CH$_2$O EE).

Example 9

N-[2-S-(2'-O-Acetyl-3'-O-ally-6'-O-tert-butyldiphenylsilyl-D-glucopyranosyl)thioethyl]-N$^4$-benzylsuccinamide 2.8 g (4.36 mmol) of the succinimide 9 are dissolved in 30 ml of THF and cooled to 0° C. After addition of 15 mg of LiOH (4.8 mmol) in 10 ml of H$_2$O, the mixture is stirred at 0° C. for 1.5 h, then acidified to pH=2.5 with 1N HCl and extracted twice with 50 ml of CH$_2$Cl$_2$ each time. The combined organic phases are dried over MgSO$_4$ and freed from the solvent in vacuo.

The crude product thus obtained is treated in 30 ml of absol. CH$_2$Cl$_2$ with 0.96 ml (8.72 mmol) of benzylamine, 767 mg (6.54 mmol) of: N-hydroxysuccinimide and 900 mg (4.36 mmol) of N,N'-dicyclohexylcarbodiimide. After 16 h, the precipitated urea is filtered off and washed with CH$_2$Cl$_2$. The combined filtrates are extracted with 50 ml of 1N HCl and 50 ml of satd NaHCO$_3$ solution. The organic phase is dried over MgSO$_4$ and the solvent is removed in vacuo. The product is purified by chromatography on silica gel using petroleum ether/ethyl acetate mixtures.

Yield: 2.13 g (67%), colorless, amorphous solid. R$_f$=0.53 (EtOAc), R$_f$=0.33 (EtOAc:PE:HOAc=30:30:1 v/v), m.p. 46–47° C.,

| C$_{40}$H$_{52}$N$_2$O$_8$SSi | (735.0) | Calc.: | C 65.37 | H 7.13 | N 3.81 | S 4.36 |
|---|---|---|---|---|---|---|
| | | Found: | C 63.68 | H 6.83 | N 3.71 | S 4.45 |

200 MHz-$^1$H-NMR (CDCl$_3$): [ppm]=7.77–7.64 (m, 4H, PhSi); 7.50–7.28 (m, 6H, PhSi); 7.25–7.13 (m, 5H, Ph amide); 6.52 (t, 1H, J$_{gem}$=5.37 Hz, NH); 6.34 (t, 1H, J$_{gem}$=5.37 Hz, NH); 5.95–5.76 (m, 1H, CH$_2$=CH); 5.28–5.12 (m, 2H, CH$_2$=CH); 4.90 (t, 1H, J$_{1,2}$=J$_{3,2}$=9.53 Hz, H-2'); 4.46–4.36 (m, 3H, H-1', CH$_2$—Ph amide); 4.28–4.04 (m, 2H, =CH—CH$_2$); 3.91–3.89 (m, 2H, H-6'a/b); 3.69 (t, 1H, J$_{3,4}$=J$_{5,4}$=9.28 Hz, H4'); 3.52–3.26 (m, 5H, H-3', H-5', CH$_2$N Cya); 2.94 (s, 1H, OH); 2.85–2.58 (m, 2H, SCH$_2$ Cya); 2.47–2.34 (m, 4H, CH$_2$CO Suc); 2.08 (s, 3H, CH$_3$ Ac); 1.03 (s, 9H, CH$_3$ tBuSi).

Preparation of the Galactose Unit

Example 10

Methyl 4-S-(2',3',4',6'-tetra-O'-acetyl-β-D-galactopyranosyl)mercaptobutyrate 16

A solution of 12 g (30 mmol) of 1,2,3,4,6-penta-O-acetylgalactose 14 and 5.5 g of methyl mercaptobutyrate 15 in 150 ml of abs. dichloromethane is prestirred for 1 h with 10 g of thoroughly heated molecular sieve 4Å. The mixture is then cooled to 0° C. and 30 ml of boron trifluoride ethyl etherate in 30 ml of abs. dichloromethane are added dropwise to the reaction mixture. It is then allowed to come to room temp. After 24 h, the precipitate is filtered off with suction through Celite and the organic phase is stirred three times with 300 ml of satd NaHCO$_3$ solution each time. It is then washed with 600 ml of water, dried over MgSO$_4$ and freed from the solvent. The product is purified by chromatography on silica gel (eluent petroleum ether/ethyl acetate 2:1, column 20×8 cm). Yield 12.5 g (90%), yellow syrup, R$_f$=0.46 (petroleum ether/ethyl acetate 1:1).

Example 11

Methyl 4-S-(6-O'-tert-butyldiphenylsilyl-β-D-galactopyranosyl)mercaptobutyrate 18

4.21 g (9.1 mmol) of 16 are dissolved in 40 ml of abs. methanol and 0.098 g (1.82 mmol) of sodium methoxide is added. After 4 h, the mixture is neutralized with acidic ion exchanger Amberlite® IR 120. The resin is filtered off and washed with methanol. After the removal of the solvent by distillation in vacuo and drying in a high vacuum, methyl S-β-D-galactopyranosylmercaptobutyrate 17 is obtained quant. as a colorless solid, $R_f$=0.56 (chloroform/methanol 2:1). The crude product is dissolved in 20 ml of DMF and treated with 1.24 g (18.1 mmol) of imidazole and 3.25 ml (12.7 mmol) of tert-butyldiphenylsilyl chloride. The mixture is stirred at room temp. for 5 h and the reaction is then terminated by addition of 10 ml of water. After 10 min, the mixture is diluted with 60 ml of dichloromethane and washed three times with 40 ml of water each time. The org. phase is dried over $MgSO_4$ and evaporated after filtration in vacuo. The residue is purified by chromatography on silica gel. Yield 4.44 g (92%).

$R_f$=0.23 (petroleum ether/ethyl acetate 1:1), 0.63 (ethyl acetate/acetic acid 30:1); 400 MHz-$^1$H-NMR ($CDCl_3$): δ [ppm]=7.98–7.64, 7.40–7.36 (m, 10H, $SiPh_2$), 4.25 (d, 1H, $J_{1,2}$=9.6 Hz, 1-H), 4.10 (s, 1H, 4-H), 3.88 (dd, 1H, $J_{gem}$=10.4 Hz, $J_{6a,5}$=6.3 Hz, 6-Ha), 3.84 (dd, 1H, $J_{gem}$=10.9 Hz, $J_{6b,5}$=5.3 Hz, 6-$H_b$), 3.69 (dd, 1H, $J_{2,1}$=9.4 Hz, $J_{2,3}$=9.2 Hz, 2-H), 3.59 (s, 3H, $COOCH_3$), 3.56 (d, 1H, $J_{3,4}$=3.1 Hz, 3-H), 3.52 (dd, 1H, $J_{5,6a}$=5.7 Hz, $J_{5,6b}$=5.0 Hz, 5-H), 3.06 ($s_{br}$, 3H, OH), 2.72 (dt, 1H, $J_{gem}$=13.9 Hz, $J_{vic}$=7.0 Hz, $SCH_a$), 2.66 (dt, 1 H, $J_{gem}$=13.9 Hz, $J_{vic}$=7.0 Hz, $SCH_b$), 2.40–2.36 ($m_c$, 2H, $CH_2COOMe$), 1.95–1.89 ($m_c$, 2H, $SCH_2CH_2$), 1.02 (s, 9H, $SiC(CH_3)_3$). 100.6 MHz-$^{13}$C-NMR ($CDCl_3$): δ [ppm]= 173.5 (COOMe), 135.6; 135.5; 133.1; 133.0; 129.9; 127.8 ($SiPh_2$), 86.0; 78.4; 75.0; 70.5; 69.1; 63.2 (C-1–C-6), 51.5 ($COOCH_3$), 32.7 ($SCH_2$), 29.2 ($CH_2COOMe$), 26.8 (SiC$(CH_3)_3$), 25.3 ($SCH_2CH_2$), 19.1 ($SiC(CH_3)_3$).

Example 12

Methyl 4-S-(6-O'-tert-butyldiphenylsilyl-3,4-O'-isopropylidene-β-D-galactopyranosyl)mercaptopropionate 19

4.15 g (7.78 mmol) of 18 are dissolved in 35 ml of acetone dimethyl acetal and the mixture is stirred at room temp. for 4 h after addition of 28 mg of p-TsOH. It is then neutralized with triethylamine. The solution is concentrated in vacuo and the oily residue is freed from impurities by chromatography on silica gel (eluent petroleum ether/ethyl acetate 2:1, column 20×5 cm).

Yield 4.03 g (90%), colorless oil, $R_f$=0.54 1:1 (petroleum ether/ethyl acetate 1:1).

400MHz-$^1$H-NMR ($CDCl_3$): δ [ppm]=7.70–7.66, 7.44–7.33 (m, 10H, Ph-H), 4.31 (dd, 1H, $J_{4,3}$=5.3 Hz, $J_{4,5}$=1.3 Hz, 4-H), 4.21 (d, 1H, $J_{1,2}$=10.3 Hz, 1-H), 4.04 (dd, 1H, $J_{3,2}$=7.0 Hz, $J_{3,4}$=5.6 Hz, 3-H), 3.90 (dd, 1H, $J_{gem}$=10.8 Hz, $J_{6a,5}$=1.2 Hz, 6-$H_a$), 3.88 (dd, 1H, $J_{gem}$=10.8 Hz, $J_{6b,5}$=4.8 Hz, 6-$H_b$), 3.87–3.85 (m, 1H, 5-H), 3.60 (s, 3H, $COOCH_3$), 3.52 (dd, $J_{2,1}$=8.8 Hz, $J_{2,3}$=8.5 Hz, 2-H), 2.75 (dt, 1H, $J_{gem}$=13.2 Hz, $J_{vic}$=7.0 Hz, $SCH_a$), 2.35 (dt, 1H, $J_{gem}$=13.2 Hz, $J_{vic}$=7.0 Hz, $SCH_b$), 2.42–2.39 ($m_c$, 2H, $CH_2COOMe$), 1.96–1.89 ($m_c$, 2H, $SCH_2CH_2$), 1.50 (s, 3H, $C(CH_3)_2$), 1.34 (s, 3H, $C(CH_3)_2$), 1.03 (s, 9H, $C(CH_3)_3$. 100.6 MHz-$^{13}$C-NMR ($CDCl_3$): δ [ppm]=173.3 (COOMe), 135.6; 135.5; 129.7; 127.7; 127.6 (C-Ph), 110.0 ($C(CH_3)_2$), 85.6; 79.1; 77.3; 73.3; 72.4; 62.7 (C-1–C-6), 51.5 ($COOCH_3$), 32.5 ($SCH_2$), 29.4 ($CH_2COOMe$), 28.2 ($C(CH_3)_2$), 26.8 ($C(CH_3)_3$), 26.2 ($C(CH_3)_2$), 25.2 ($SCH_2CH_2$).

Example 13

Methyl 4-S-(2-O'-Acetyl-6-O'-tert-butyldiphenylsilyl-3,4-O'-isopropylidene-β-D-galactopyranosyl)mercaptobutyrate 20

A solution of 27.6 g (48 mmol) of 19 in 100 ml of acetic anhydride/pyridine (1:1) is stirred for 5 h at room temp. It is then concentrated in a high vacuum and the residue is taken up in 100 ml of dichloromethane. The solution is washed with 50 ml each of 0.5 N HCl, satd $NaHCO_3$ solution and water. After drying over $MgSO_4$, the mixture is freed from the solvent in vacuo. Chromatography on silica gel (eluent petroleum ether/ethyl acetate 4:1, column 30×10 cm) yields the title compound. Yield 24.3 g (82%), colorless oil, $R_f$=0.66 (petroleum ether/ethyl acetate 1:1). 400 MHz-$^1$H-NMR ($CDCl_3$): δ [ppm]=7.70–7.66, 7.43–7.33 (m, 10H, Ph-H), 4.98 (dd, $J_{2,1}$=10.0 Hz, $J_{2,3}$=7.3 Hz, 2-H), 4.34 (d, 1H, $J_{4,3}$=5.3 Hz, 4-H), 4.31 (d, 1H, $J_{1,2}$=10.3 Hz, 1-H), 4.15 (dd, 1H, $J_{3,2}$=7.3 Hz, $J_{3,4}$=5.2 Hz, 3-H), 4.10–3.86 (m, 3H, 6-$H_{a,b}$, 5-H), 3.58 (s, 3H, $COOCH_3$), 2.72 (dt, 1H, $J_{gem}$=12.9 Hz, $J_{vic}$=7.0 Hz, $SCH_a$), 2.60 (dt, 1H, $J_{gem}$=12.6 Hz, $J_{vic}$=7.0 Hz, $SCH_b$), 2.41–2.32 ($m_c$, 2H, $CH_2COOMe$), 2.08 (s, 3H, $COCH_3$), 1.93–1.83 ($m_c$, 2H, $SCH_2CH_2$), 1.53 (s, 3H, $C(CH_3)_2$), 1.33 (s, 3H, $C(CH_3)_2$), 1.03 (s, 9H, $C(CH_3)_3$). 100.6 MHz-$^{13}$C-NMR ($CDCl_3$): δ [ppm]=173.2 (COOMe), 169.5 (COMe), 135.5; 135.5; 133.4; 133.3; 129.7; 127.6; 127.6 (C-Ph), 110.2 ($C(CH_3)_2$), 82.7; 77.4; 76.7; 73.4; 71.7; 62.6 (C-1- C-6), 51.4 ($COOCH_3$), 32.6 ($SCH_2$), 29.1 ($CH_2COOMe$), 27.8 ($C(CH_3)_2$), 26.8 ($C(CH_3)_3$), 26.3 ($C(CH_3)_2$), 24.9 ($C(CH_3)_3$), 20.9 ($COCH_3$), 19.2 ($SCH_2CH_2$).

Example 14

Methyl 4-S-(3-O'-Allyl-2-O'-acetyl-4-O'-[1-(R/S)-ethoxyethyl]-6-O'-tert-butyidiphenyisilyl-β-D-galactopyranosyl)mercaptobutyrate 21 a) Methyl 4-S-(2-O'-Acetyl-6-O'-tert-butyidiphenyisilyl-β-D-galacto-pyranosyl)mercaptobutyrate A solution of 23.97 g (38.86 mmol) of 20 in 370 ml of $CHCl_3$ is heated to reflux with 0.35 g (1.84 mmol) of p-toluenesulfonic acid and 22.70 ml (270 mmol) of ethanedithiol. After 5 h, the mixture is cooled to room temp. and washed with 50 ml each of satd sodium hydrogencarbonate solution, 0.5 N HCl and water. The organic phase is dried over magnesium sulfate. The product is obtained pure by chromatography on silica gel (eluent petroleum ether/ethyl acetate 1:1). Yield 16.66 g (74%), colorless oil, $R_f$=0.16 (petroleum ether/ethyl acetate 2:1). 400 MHz-$^1$H-NMR ($CDCl_3$): δ [ppm]=7.68–7.63, 7.42–7.34 (m, 10H, Ph-H), 5.06 (dd, $J_{2,1}$=9.6 Hz, $J_{2,3}$=9.6 Hz, 2-H), 4.31 (d, 1H, $J_{1,2}$=9.9 Hz, 1-H), 4.11 (d, 1H, $J_{4,3}$=5.3 Hz, 4-H), 3.92–3.84 (m, 2H, 6-$H_{a,b}$), 3.61 (d, 1H, $J_{3,4}$=3.4 Hz, 3-H), 3.58 (s, 3H, $COOCH_3$), 3.50 (t, 1H, $J_{5,6}$=5.5 Hz, 5-H), 2.73 (dt, 1H, $J_{gem}$=13.0 Hz, $J_{vic}$=7.2 Hz, $SCH_a$), 2.59 (dt, 1H, $J_{gem}$=13.0 Hz, $J_{vic}$=7.2 Hz, $SCH_b$), 2.40–2.16 ($m_c$, 2H, $CH_2COOMe$), 2.09 (s, 3H, $COCH_3$), 2.01–1.81 ($m_c$, 2H, $SCH_2CH_2$), 1.03 (s, 9H, $C(CH_3)_3$). 100.6 MHz-$^{13}$C-NMR ($CDCl_3$): δ [ppm]= 173.4 (COOMe), 170.8 (COMe), 135.5; 135.4; 132.9; 132.7; 129.9; 127.8 (C-Ph), 83.2; 78.1; 73.7; 71.2; 69.6; 63.3 (C-1-C-6), 51.5 ($COOCH_3$), 32.6 ($SCH_2$), 28.8 ($CH_2COOMe$), 26.8 ($C(CH_3)_3$), 25.1 ($C(CH_3)_3$), 20.9 ($COCH_3$), 19.1 ($SCH_2CH_2$).

b) Methyl 4-S-(3-O'-allyl-2-O'-acetyl-6-O'-tert-butyldiphenylsilyl-β-D-galactopyranosyl)mercaptobutyrate A mixture of 5.7 g (9.8 mmol) of the compound from Ex. 14a) and 3.3 g (9.43 mmol) of dibutyltin oxide in 70 ml of benzene is heated to reflux for 8 h in a water separator. 35 ml of benzene are then removed by distillation and the mixture is treated with 1.76 g (9.43 mmol) of tetrabutylammonium bromide and 1.35 ml (15.6 mmol) of allyl bromide. The solution is stirred at 50° C. for 16 h. After addition of 5 ml of methanol, it is largely concentrated in vacuo. The residue is taken up in 50 ml of dichloromethane and washed three times with 10 ml of water each time. After drying over $MgSO_4$, the solvent is removed in vacuo. The crude product is purified. by chromatography (eluent petroleum ether/ethyl acetate 4:1, column 15×5 cm) on silica gel. Yield 3.79 g (63%) of yellowish oil, $R_f$=0.34 (petroleum ether/ethyl acetate 4:1). 400MHz-$^1$H-NMR ($CDCl_3$): δ [ppm]= 7.68–7.65, 7.42–7.34 (m, 10H, Ph-H), 5.90–5.80 ($m_c$, 1H, =CH), 5.26 (d, 1H, $J_{vic}$=17.6 Hz, $CH_{trans}$=), 5.20 (dd, 1H, $J_{2,1}$=10.0 Hz, $J_{2,3}$=9.8 Hz, 2-H, R+S), 5.18 (d, 1H, $J_{vic}$=11.8 Hz, $CH_{cis}$=), 4.30 (d, 1H, $J_{1,2}$=10.0 Hz, 1-H), 4.16 (d, 1H, $J_{4,5}$=2.7 Hz, 4-H), 4.11 (dd, 1H, $J_{gem}$=12.9 Hz, $J_{vic}$=5.6 Hz, =CH—$CH_a$), 4.03 (dd, 1H, $J_{gem}$=12.9 Hz, $J_{vic}$=5.6 Hz, =CH—$CH_b$), 3.94 (dd, 1H, $J_{gem}$=10.3 Hz, $J_{6a,5}$=6.5 Hz, 6-$H_a$), 3.86 (dd, 1H, $J_{gem}$=10.3 Hz, $J_{6b,5}$=5.6 Hz, 6-$H_b$), 3.59 (s, 3H, $COOCH_3$), 3.50 (dd, 1H, $J_{5,6a}$=$J_{5,6b}$=5.9 Hz, 5-H), 3.44 (dd, 1H, $J_{3,2}$=9.4 Hz, $J_{3,4}$=2.7 Hz, 3-H), 2.75 (dt, 1H, $J_{gem}$=13.2 Hz, $J_{vic}$=7.0 Hz, $SCH_a$), 2.61 (dt, 1H, $J_{gem}$=13.2 Hz, $J_{vic}$=7.0 Hz, $SCH_b$), 2.37 ($m_c$, 2H, $SCH_2CH_2$), 2.07 (s, 3H, $COCH_3$), 1.88 ($m_c$, 2H, $CH_2COOMe$), 1.03 (s, 9H, $SiC(CH_3)_3$).

c) Methyl 4-S-(3-O'-Allyl-2-O'-acetyl-4-O'-[1-(R/S)-ethoxyethyl]-6-O'-tert-butyldiphenylsilyl-β-D-galactopyranosyl)mercaptobutyrate 1.95 g (3.15 mmol) of the compound according to Example 14b) are dissolved in 45 ml of dichloromethane and the mixture is stirred at room temp. for 4 h after addition of 45 ml of ethyl vinyl ether and 0.39 g (1.56 mmol) of pyridium p-toluenesulfonate. The mixture is poured into satd $NaHCO_3$ solution and the aq. phase is extracted with ethyl acetate.

The combined org. phases are then dried over $MgSO_4$, and freed from the solvent in vacuo. Purification is carried out by chromatography on silica gel (eluent petroleum ether/ethyl acetate 4:1, column 15×2 cm). Yield 1.49 g (69%), colorless oil, $R_f$=0.39 (petroleum ether/ethyl acetate 4:1). 400 MHz-$^1$H-NMR ($CDCl_3$): δ [ppm]=8.03–8.01; 7.69–7.36 (m, 10H, Ph-H), 5.80–5.65 ($^2m_c$, 1H, =CH, R+S), 5.56, 5.50 (2dd, 1H, $J_{2,1}$=$J_{2,3}$=9.8 Hz, 2-H, R+S), 5.26–5.01 (m, 2H, $CH_{trans}$=, $CH_{cis}$=, R+S), 4.94 (q, 1H, $CHCH_3$), 4.52, 4.46 (2d, 1H, $J_{1,2}$=10.3 Hz, 1-H, R+S), 4.16–3.45 (m, 7H, 4-H, $^6$-$H_{a,b}$, 5-H, 3-H, =CH—$CH_{a,b}$, R+S), 3.54, 3.53 (2s, 3H, $COOCH_3$, R+S), 3.69–3.63, 3.32–3.25 (2$m_c$, 2H, $CH_2CH_3$, R+S), 3.04–2.94, 2.89–2.78 (2$m_c$, 2H, $SCH_2$ R+S), 2.66, 2.60 (2t, $J_{vic}$=7.3 Hz, $SCH_2CH_2$, R+S), 1.33, 1.26 (2d, 3H, $J_{vic=}$5.3 Hz, $CHCH_3$, R+S), 1.17, 0.95 (2t, 3H, $J_{vic}$=7.0 Hz, $CH_2CH_3$, R+S), 1.07, 1.05 (2s, 9H, $C(CH_3)_3$, R+S).

The hydrolysis of the ester is carried out as described in the case of glucose.

Preparation of the Mannose Derivatives

Example 15

Monomethyl N-[2-S-(2',3',4',6'-tetra-O-Acetyl-α-D-mannopyranosyl)thio-ethyl]succinamidate 23

A solution of 11.1 g (34.3 mmol) of monomethyl N-(2-thioethyl)succinamidate 6 and 43 ml (0.34 mol) of boron trifluoride etherate in 70 ml of $CH_2Cl_2$ is added dropwise with ice-cooling to 10.0 g (25.6 mmol) of the anomer mixture 22 in 300 ml of $CH_2Cl_2$. The solution is warmed to room temp. and stirred for 12 h. The mixture is washed twice with 500 ml of satd $NaHCO_3$ solution in each case and the organic phase is dried over $MgSO_4$. After chromatography on silica gel using petroleum ether/ethyl acetate (1:2), 5.5 g (44%) of pure α-product are obtained as a colorless oil and also 2.3 g (19%) of an α,β-mixed fraction as a yellowish oil.

$R_f$=0.24 (PE/EtOAc=1:2 v/v), $R_f$=0.52 (EtOAc/HOAc= 30:1 v/v), 200 MHz-$^1$H-NMR ($CDCl_3$): δ [ppm]=6.28 ($s_b$, 1H, NH); 5.30–5.14 (m, 4H, H-1', H-2', H-3' & H-4'); 4.37–4.06 (m, 3H, H-5' & H-6'a/b); 3.65 (s, 3H, $CO_2CH_3$); 3.57–3.39 (m, 2H, $CH_2N$ Cya); 2.85–2.71 (m, 2H, $SCH_2$ Cya); 2.63 (t, 2H, $J_{vic}$=7.08 Hz, $CH_2CO$ Suc); 2.45 (t, 2H, $J_{vic}$=7.09 Hz, $CH_2CON$ Suc); [lacuna].08, 20.7, 20.5 (3×s, 12H, $CH_3$ Ac).

Example 16

N-[2-S-(α-D-Mannopyranosyl)thioethyl]succinimide 24

1.5 ml of a 1 M solution of sodium methoxide in methanol are added under argon and with ice-cooling to 7.9 g (15.2 mmol) of the glycoside 23 in 100 ml of methanol p.a., and the mixture is stirred at room temp. for 2 h and neutralized with Amberlyst® 15. The ion exchanger is filtered off, washed with methanol and the solvent is removed in vacuo. Residues of methanol are removed by codistillation with toluene. 4.8 g (97%) are obtained as a yellowish oil, which still contains slight impurities. The crude product is employed in the next stage without further purification.

$R_f$=(toluene:EtOH=4.1 v/v).

Example 17

N-[2-S-(4',6'-O-Benzylidene-α-D-mannopyranosyl) thioethyl]succinimide 25

5.5 g (10.55 mol) of the thiogiycoside 23 are treated at room temp. with 100 mg (1.8 mmol) of NaOMe in 75 ml of methanol. After 2 h, thin-layer chromatographic checking indicates incomplete conversion, for which reason a further 100 mg of NaOMe are added. After a further 1.5 h, the mixture is neutralized with acidic ion exchanger Amberlyst® 15. The ion exchanger is filtered off and the solvent is removed in vacuo. The crude product is treated in 50 ml of absol. DMF with 3.1 ml (20 mmol) of benzaldehyde dimethyl acetal and 112 mg (1 mmol) of p-toluenesulfonic acid and stirred at 50° C. and 50–70 mbar for 2 h. The mixture is neutralized with 10 ml of triethylamine and the solvent is removed in a high vacuum. The residue is taken up in 200 ml of $CH_2Cl_2$ and extracted twice with 75 ml of $NaHCO_3$. The organic phase is separated off and dried over $MgSO_4$, and the solvent is removed in vacuo. By chromatography on silica gel using petroleum ether/ethyl acetate mixtures, 3.33 g (77%) of a colorless oil are obtained.

$R_f$=0.44 (EtOAc/HOAc=30:1 v/v), 200 MHz-$^1$H-NMR ($CDCl_3$): δ [ppm]=7.43–7.41 (m, 2H, Ph); 7.33–7.29 (m, 3H, Ph); 5.48 (s, 1H, PhCH); 5.32 (s, 1H, H-1'); 4.19–3.43 (m, 8H, H-2', H-3', H4', H-5', H-6a/b', $NCH_2$ Cya); 2.80–2.64 (m, 2H, $SCH_2$ Cya); 2.58 (s, 4H, $COCH_2$ Suc).

Example 18

N-[2-S-(2'-O-Acetyl-3'-O-allyl-4',6'-O-benzylidene-α-D-mannopyranosyly-thioethyl]succinimide 26

330 mg (0.81 mmol) of 25 are treated with 227 mg (0.91 mmol) of dibutyltin oxide in 20 ml of methanol. The suspension is heated under reflux for 2.5 h, freed from the solvent in vacuo and the residue is dried in a high vacuum. The tin acetal is treated with 0.12ml (1.4 mmol) of allyl bromide and 517 mg (1.4 mmol) of TBAI in 20 ml of absol. toluene and the mixture is stirred at 40° C. for 6 h. Thin-layer chromatographic checking indicates a low conversion. The reaction is therefore continued at 80° C. After 7 h, the solvent is removed in vacuo and the product is isolated by chromatography on silica gel two times using petroleum ether/ethyl acetate mixtures. 300 mg of a rust-colored oil are obtained, which according to the NMR spectrum still contains tin residues.

$R_f$=0.56 (toluene/EtOH=4:1 v/v), 200 MHz-$^1$H-NMR (CDCl$_3$): δ [ppm]=7.48–7.43 (m, 2H, Ph); 7.36–7.31 (m, 3H, Ph); 5.96–5.77 (m, 1H, CH$_2$=CH); 5.55 (s, 1H, PhCH); 5.40 (s, 1H, H-1); 5.26 (dd, 1H, Jgem,trans=17.09 Hz, $J_{vic}$=1.46 Hz, CH$_2$=CH); 5.16 (dd, 1H, $J_{gem,cis}$=10.26 Hz, $J_{vic}$=0.98 Hz, CH$_2$=CH); 4.31–4.01 (m, 5H, H-2, H6a/b, =CH—CH$_2$); 3.88–3.60 (m, 3H, H-4, NCH$_2$ Cya); 3.29–3.20 (m, 2H, H-3, H-5); 2.85–2.76 (m, 2H, SCH$_2$ Cya); 2.69 (s, 4H, COCH$_2$ Suc).

300 mg (0.67 mmol) of 25 are stirred at room temp. for 1.5 h with 2 ml of acetic anhydride and a spatula-tipful [lacuna] in 10 ml of pyridine. The solvent is removed in vacuo and the product is purified by chromatography on silica gel using petroleum ether/ethyl acetate (1:1). 191 mg (48% over two stages) of a yellow oil are obtained. $R_f$=0.63 (toluene/EtOH=4:1 v/v), 1200 MHz-$^1$H-NMR (CDCl$_3$): δ [ppm]=7.47–7.42 (m, 2H, Ph); 7.37–7.32 (m, 3H, Ph); 5.96–5.70 (m, 1H, CH$_2$=CH); 5.66 (s, 1H, PhCH); 5.33–5.08 (m, 3H, CH$_2$=CH, H-2); 5.25 (s, 1H, H-1); 4.44–4.0 (m, 5H, H4, H-6a/b, =CH—CH$_2$); 3.85–3.45 (m, 4H, H-3, H-5, NCH$_2$ Cya); 2.87–2.72 (m, 2H, SCH$_2$ Cya); 2.65 (s, 4H, COCH$_2$ Suc); 2.12 (s, 3H, CH$_3$ Ac).

Example 19

N-[2-S-(2'-O-Acetyl-3'-O-allyl-6'-O-tert-butyldiphenylsilyl-4'-O-(1"-(R/S)-ethoxyethyl)-α-D-mannopyranosyl)thioethyl]succinimide 27

0.12 ml of a 48% strength solution of HBF$_4$ in water is added to 180 mg (0.37 mmol) of 26 in 10 ml of absol. acetonitrile and the reaction solution is stirred for 2 h at room temp. Thin-layer chromatographic checking shows complete conversion and the mixture is treated with 10 ml of satd NaHCO$_3$ solution and extracted twice with 50 ml of CH$_2$Cl$_2$. The combined organic phases are dried over MgSO$_4$ and the solvent is removed in vacuo. The residue is taken up in 10 ml of absol. CH$_2$Cl$_2$ and treated with 0.19 ml (0.72 mmol) of tert-butyldiphenylchlorosilane and 100 mg (1.5 mmol) of imidazole. After 16 h, the solution is diluted with 50 ml of CH$_2$Cl$_2$ and extracted with 0.5 N HCl solution. The organic phase is dried over MgSO$_4$ and the solvent is removed in vacuo. By chromatography on silica gel using petroleum ether/ethyl acetate mixtures, 69 mg (30%) of the product are obtained as a colorless oil. $R_f$=0.21 (toluene/EtOH=4:1 v/v), 400 MHz-$^1$H-NMR (CDCl$_3$): δ [ppm]=7.69–7.65 (m, 4H, PhSi); 7.41–7.33 (m, 6H, PhSi); 5.89–5.80 (m, 1H, CH$_2$=CH); 5.32 (d, 1H, $J_{1,2}$=1.17 Hz, H-2); 5.29 (s, 1H, H-1); 5.26 (dd, 1H, $J_{vic,trans}$=16.88 Hz, $J_{gem}$=1.62 Hz, CH$_2$CH); 5.18 (dd, 1H, $J_{vic,cis}$=11.74 Hz, $J_{gem}$=1.47 Hz, CH$_2$CH); 4.11 (dd, 1H, $J_{gem}$=12.32 Hz, $J_{vic}$=5.58 Hz, =CH—CH$_2$); 4.00–3.88 (m, 5H, H-3, H4 & H-6a/b); 3.78–3.71 (m, 1H, H-5); 3.64–3.58 (m, 2H, CH$_2$N Cya); 2.82–2.68 (m, 2H, SCH$_2$ Cya); 2.66 (s, 4H, CH$_2$CO Suc); 2.08 (s, 3H, CH$_3$ Ac); 1.03 (s, (h, 9H, CH$_3$ tBuSi).

69 mg (0.11 mmol) of the succinimide are reacted with 0.1 ml (1.1 mmol) of ethyl vinyl ether and 27 mg (0.11 mmol) of pyridinium toluene-4-sulfonate in 10 ml of absol. CH$_2$Cl$_2$. After 4 h, the conversion according to the thin-layer chromatogram is only about 70%, so a further 0.1 ml of ethyl vinyl ether and 27 mg of pyridinium toluene4-sulfonate are added and the reaction time is lengthened to 16 h. The mixture is diluted with 30 ml of CH$_2$Cl$_2$ and extracted with satd NaHCO$_3$ solution. The organic phase is dried over MgSO$_4$ and the solvent is removed in vacuo. By chromatography on silica gel using petroleum ether/ethyl acetate (1:1) 42 mg (56%) of a colorless oil are obtained. In addition, some fractions are obtained which contain unreacted starting material. $R_f$=0.44 (toluene/EtOH=4:1 v/v), [α]=+96.1° (c 1, CHCl$_3$). 400 MHz-$^1$H-NMR (CDCl$_3$): δ [ppm]=7.70–7.63 (m, 4H, PhSi); 7.38–7.31 (m, 6H, PhSi); 5.88–5.76 (m, 1H, CH$_2$=CH); 5.32–5.26 (m, 2H, H-1 & H-2); 5.24, 5.18 (dm, 1H, $J_{vic,trans}$=16.88 Hz, CH$_2$=CH); 5.15, 5.12 (d$_m$, 1H, $J_{vic,cis}$=10.57 Hz, CH$_2$=CH); 4.90, 4.87 (m, 1H, CHCH$_3$ EE); 4.10–3.42 (m, 10.5H, H-3, H4, H-5, H-6a/b, =CH—CH$_2$, CH$_3$CH$_2$O EE & CH$_2$N Cya); 3.22–3.16 (m, 0.5H, H-5); 2.74–2.70 (m, 2H, SCH$_2$ Cya); 2.67, 2.65 (2×s, 4H, CH$_2$CO Suc); 2.10, 2.09 (2×s, 3H, CH$_3$ Ac); 1.24–1.20 (m, 3H, CHCH$_3$ EE); 1.15 (t, 1.5H, $J_{gem}$=7.05 Hz, CH$_3$CH$_2$O EE ); 1.04, 1.02 (2×s 9H, CH$_3$ tBuSi); 0.89 (t, 1.5H, $J_{gem}$=7.05 Hz, CH$_3$CH$_2$O EE).

The hydrolysis of the ester is carried out as described in the case of glucose.

General Procedures for Synthesis on Polymeric Supports

General Procedure for the Coupling of the Thioglycosides to the Amino-functionalized Polymeric Supports A solution of 14.6 mmol of a thioglycoside is shaken overnight in a solid-phase reactor with 15.4 g (19.8 mmol, 1.28 mmol/g) of aminomethylpolystyrene, 3.7 ml (14.6 mmol) of diisopropylcarbodiimide and 3.86 g (14.6 mmol) of N-hydroxylbenzotriazole. The resin is then filtered off with suction and washed ten times with 50 ml each of DMF and dichloromethane. The loaded polymer is dried in vacuo and the loading with carbohydrate matrix is determined by means of elemental analysis. As a rule, the loading is 50–80% of the maximally possible loading.

General Procedure for the Removal of the Glycoside Derivatives from the Polymeric Support a) analytical: A suspension of 80 mg, (0.056 mmol) of polymer-bonded derivative in 1.5 ml of abs. dichloromethane is shaken at room temperature in a 5 ml PE syringe (PE frit, plastic cap) with 0.3 ml of a 3.5 percent solution of bromine in abs. dichloromethane and 0.08 ml (0. [lacuna] mmol) of 2,6-di-tert-butylpyridine or a corresponding amount of polymer-bonded 2,6-di-tert-butylpyridine. After 15 min, 0.2 ml of cyclohexene, 0.2 ml of the abs. alcohol to be glycosylated and 25 mg (0.056 mmol) of tetraethylammonium bromide are added. After 2.5 h, the resin is filtered off and washed five times with 1 ml of dichloromethane. The combined filtrates are freed from the solvent in vacuo. The crude product obtained is applied to a silica gel cartridge in a little dichloromethane. It is eluted first with 30 ml of petroleum ether. This fraction is discarded. The product is obtained by eluting with petroleum ether/ethyl acetate (1:1). Characterization by HPLC and MS analysis follows.

b) preparative: A suspension of 400 mg (0.312 mmol) of polymer-bonded galactose derivative in 3 ml of abs. dichloromethane is shaken at room temp. in a 5 ml PE syringe (PE frit, plastic cap) with 1.2 ml of a 3.5 percent solution of bromine in abs. dichloromethane and 0.32 ml (0. [lacuna] mmol) of 2,6-di-tert-butylpyridine. After 15 min, the resin is filtered off and washed five times with 3 ml of dichloromethane each time. 0.5 ml of cyclohexene, 0.5 ml of the abs. alcohol to be glycosylated and 25 mg (0.056 mmol) of tetraethylammonium bromide are added to the filtrate. The organic phase is washed with water, dried over magnesium sulfate and concentrated in vacuo, and the residue is purified by flash chromatography on silica gel.

General Procedure for the Alkylation of the Glycosides on the Polymeric Support with Potassium tert-Butoxide A solution of 87 mg (0.78 mmol) of potassium tert-butoxide in abs. DM,F is added to a suspension of 100 mg (0.078 mmol) of loaded polymer in 1.5 ml of abs. DMF. The mixture is shaken for 15 min. It is filtered and, the Filtrate is discarded. 0.78 mmol of the appropriate alkylating agent in 1.5 ml of abs. DMF is then added and the mixture is shaken for 4 h. The resin is separated from the solution and washed five times with 2 ml each of DMF, toluene and dichloromethane.

General Procedure for the Alkylation of the Galactosides on the Polymeric Support with tert-Butyl-$P_4$ Base (Schwesinger Base)

A solution of 0.22 ml (0.22 mmol) of tert-butyl-$P_4$ base in abs. DMF is added to a suspension of 80 mg (0.056 mmol) of loaded polymer in 1.5 ml of abs. DMF. The mixture is shaken for 10 min. 0.56 mmol of the appropriate alkylating agent is then added and the mixture is shaken for 2–4 h. The resin is filtered off with suction from the solution and washed five times with 2 ml each of DMF, toluene and dichloromethane.

General Procedure for the Removal of the Acetate Protective Group on the Polymeric Support 0.3 ml of a 30% strength sodium methanolate solution is added to, a uspension of 0.0050 mmol of loaded polymer in 2 ml of ioxane/methanol. The mixture is shaken at room temperature for 3 h. The resin is filtered off with suction from the solution and first washed five times with methanol/dioxane and then five times with 2 ml each of DMF and dichloromethane.

General Procedure for the Removal of the tert-Butyldiphenylsilyl Protective Group on the Polymeric Support 0.56 ml (0.56 mmol, 1M) of tetrabutylammonium fluoride in THF is added to a suspension of 0.056 mmol of loaded polymer in 1.5 ml of THF. The mixture is shaken for 4 h. The resin is filtered off with suction from the solution and washed five times with 2 ml each of DMF and dichloromethane.

General Procedure for the Removal of the Ethoxyethyl Ether Protective Group on the Polymeric Support para-Toluenesulfonic acid is added to a suspension of 0.050 mmol of loaded polymer in 1.5 ml of dioxane/methanol and the mixture is stirred at 40° C. for 4 h. The resin is filtered off with suction from the solution and washed with 0.5N HCl solution and then washed five times with 2 ml each of DMF and dichloromethane.

The isopropyl protective group can be removed under analogous conditions. The reaction times or temperatures may change in this case.

General Procedure for the Removal of the Allyl Ether Protective Group on the Polymeric Support A solution of 198 mg of zirconocene dichloride and 0.63 ml of BuLi (1.7 M) in THF is added at −70° C. to a suspension of 0.060 mmol of loaded polymer in 1.5 ml of THF. The mixture is stirred at room temperature for 4 h after addition is complete. The resin is filtered off with suction from the solution and washed with 0.5N HCl solution and then washed five times with 2 ml each of DMF and dichloromethane.

Example 20

Methyl 2-O-methyl-6-O-tert-Butyldiphenylsilyl-3-O-propyl-α,β-D-glucopyranoside 166 mg (0.1 mmol) of the polymer are reacted with methyl iodide according to the general working procedure for an alkylation. After filtration on silica gel, 16 mg of a colorless oil are obtained. The product is purified by preparative HPLC and individual fractions are identified by mass spectrometric analysis and NMR spectra.

$R_f$=0.45, 0.34 (PE/EtOAc=4:1 v/v). FBA-MS (NBA-pos, LiCl): (m/e)=495.2 (100%, [M+Li]$^+$, calc.: 295;2); 496.2 (26%, [M+Li]$^+$, C, ca3c.: 496.2).

Example 21

Methyl 2-O-benzyl-6-O-tert-butyldiphenylsilyl-3-O-propyl-α,β-D-gluco-pyranoside 166 mg (0.1 mmol) of the polymer are reacted with benzyi bromide according to the general working procedure for an alkylation and the carbohydrate is removed from the resin. After filtration on silica gel, 15 mg of a colorless oil are obtained. The product is purified by preparative HPLC and individual fractions are identified by mass spectrometric analysis and NMR spectra.

$R_f$=0.53, 0.47 (PE/EtOAc=4:1 v/v). $C_{33}H_{44}O_6Si$ (564.8) FBA-MS (NBA-pos, LiCl): (m/e)=571.1 (100%, [M+Li]$^+$, calc.: 571.3); 572.1 (35%, [M+Li]$^+$, $^{13}$C, calc.: 572.3).

Example 22

Methyl 2-O-propyl-6-O-tert-butyldiphenylsilyl-3-O-propyl-α,β-D-gluco-pyranoside 166 mg (0.1 mmol) of the polymer are reacted with n-propyl iodide according to the general working procedure for an alkylation and the carbohydrate is removed from the resin. After filtration on silica gel, 18 mg of a colorless oil are obtained.

$R_f$=0.49, 0.46 (PE/EtOAc=4:1 v/v). $C_{29}H_{44}O_6Si$ (516.8) FBA-MS (NBA-pos, LiCl): (m/e) 523.3 (100%, [M+Li]$^+$, calc.: 523.2); 524.3 (33%, [M+Li]$^+$, calc.: 524.2).

Example 23

Methyl 2-O-(2'-Naphthyl)methyl-6-O-tert-butyldiphenylsilyl-3-O-propyl-α,β-D-glucopyranoside 166 mg (0.1 mmol) of the polymer are reacted with (2-naphthyl)methylene bromide according to the general working procedure for an alkylation and the carbohydrate is removed from the resin. After filtration on silica gel, 22 mg of a slightly yellowish oil are obtained. It was possible to detect the desired product by mass spectrometry.

Example 24

Methyl 2-O-Isopropyl-6-O-tert-butyldiphenylsilyl-3-O-propyl-α,β-D-glucopyranoside 66 mg (0.1 mmol) of the polymer are reacted with 2-propyl bromide according to the general working procedure for an alkylation and the carbohydrate is removed from the resin. After filtration on silica gel, 17 mg are obtained. The product can be detected by mass spectrometry.

HPLC (gradient 54180): Rt (min)=3.61 (15.3%, DTBpy); 14.2 (11.0%, 2-OH); 15.7 (19.2%).

Example 25

Methyl 2-O-(4'-Cyanobenzyl)-6-O-tert-butyldiphenylsilyl-3-O-propyl-α,β-D-glucopyranoside 166 mg (0.1 mmol) of the polymer are reacted with o-cyanobenzyl bromide according to the general working procedure for an alkylation and the carbohydrate is removed from the resin. After filtration on silica gel, 22 mg of a slightly yellowish oil are obtained. Rf=0.52, 0.47 (PE|EtOAc=4:1 v/v).

$C_{33}H_{43}NO_6Si$ (577.8) FBA-MS (NBA-pos, LiCl): (m/e)= 241.1 (69%); 596.3 (38%, [M+Li]$^+$, calc.: 596.4); 597.3 (22%, [M+Li]$^+$, C, calc.: 597.4); 746.4 (66%, [M+C$_4$H$_8$$^{79}$BrO+H]$^+$, calc.: 746.4); 747.4 (64%, [M+C$_4$H$_8$$^{79}$BrO+H]$^+$, $^{13}$C, calc.: 747.4); 748.4 (100%, [M+C$_4$H$_8$$^{81}$BrO+H]$^+$, calc.: 748.4); 749.4 (57%, [M+C$_4$H$_8$$^{81}$BrO+H]$^+$, C, calc.: 749.4).

Example 26

Methyl 2-O-heptyl-6-O-tert-butyldiphenylsilyl-3-O-propyl-α,β-D-glucopyranoside 166 mg (0.1 mmol) of the polymer are reacted with 1-iodoheptane according to the general working procedure for an alkylation and the carbohydrate is removed from the resin. After filtration on silica gel, 25 mg of a colorless oil are obtained.

$R_f$=0.65, 0.49 (PE/EtOAc=4:1 v/v). $C_{33}H_{43}NO_6Si$ (577.79); FBA-MS (NBA-pos, LiCl): (m/e)=241.1 (100%); 579.4 (74%, [M+Li]$^+$, calc.: 579.4); 580.4 (31%, [M+Li]$^+$, C, calc.: 580.4); 729.4 (72%, [M+C$_4$H8$^{79}$BrO+H]$^+$, calc.: 729.4); 730.4 (38%, [M+C$_4$H$_8$$^{79}$BrO+H]$^+$, —C, calc.: 730.4); 731.4 (79%, [M+C$_4$H$_8$$^{79}$BrO+H]$^+$, calc.: 731.4); 732.4 (34%, [M+C$_4$H$_8$$^{81}$BrO+H]$^+$, C, calc.: 723.4).

Example 27

Methyl 2-O-(2'-methoxy-5'-nitrobenzyl)-6-O-tert-butyldiphenylsilyl-3-O-propyl-α,β-D-glucopyranoside 166 mg (0.1 mmol) of the polymer are reacted with 2-methoxy-5-nitrobenzyl bromide according to the general working procedure for an alkylation and the carbohydrate is removed from the resin. After filtration on silica gel, 15 mg of a slightly yellowish oil are obtained.

$R_f$=0.48, 0.43 (PE/EtOAc=4:1 v/v). $C_{33}H_{45}NO_9Si$ (627.8).

Example 28

Methyl 2-O-methyl-6-O-benzyl-3-O-propyl-α,β-D-glucopyranoside 166 mg (0.1 mmol) of the polymer are reacted with methyl iodide according to the general working procedure for an alkylation. The TBDPS group is subsequently removed and the product is alkylated with benzyl bromide. After removal of the carbohydrate from the resin and filtration on silica gel, 24 mg of a colorless oil are obtained. For confirmed characterization of the product and assignment of the two anomers, the product was purified by preparative HPLC (gradient 90/10).

$C_{18}H_{28}O$ (340.4); $R_f$=0.63, 0.54 (PE/EtOAc=3:1 v/v). 400 MHz-$^1$H-NMR (CDCl$_3$): δ [ppm]=7.32–7.31 (m, 5H, Ph); 4.83 (d, 1H, $J_{2,1}$=3.81 Hz, H-1); 4.60 (d, 1H, $J_{gem}$=12.32 Hz, CH$_2$Ph); 4.55 (d, 1H, $J_{gem}$=12.03 Hz; CH$_2$Ph); 4.20 (dd, 0.3H, $J_{1,2}$=3.23 Hz, $J_{3,2}$=12.03 Hz, =H-2), 4.12 (dd, 0.7H, $J_{1,2}$=2.94 Hz, $J_{3,2}$=11.45 Hz, H-2); 4.00 (dd, 0.3H, $J_{vic}$=11.89 Hz, $J_{gem}$=6.61 Hz, OCH$_2$ Pr); 3.92 (dd, 0.7H, $J_{vic}$=11.44 Hz, $J_{gem}$=7.34 Hz, OCH$_2$ Pr); 3.83–3.82 (m, 1.6H, H-6a/b); 3.81–3.39 (m, 8.4 Hz, H-3, H-4, H-6b); 3.47, 3.41 (2×s, 6H, OCH$_3$); 3.23–3.21 (m, 1H, H-5); 1.91 (s$_b$, 1H, OH); 1.61–1.54 (m, 2H, OCH$_2$CH$_2$ Pr); 0.91 (t, 3H, $J_{gem}$=7.34 Hz, CH$_3$ Pr);

Example 29

Benzyl 2-O-methyl-6-O-methyl-3-O-propyl-α,β-D-glucopyranoside 166 mg (0.1 mmol) of the polymer are reacted with methyl iodide according to the general working procedure for an alkylation. The TBDPS group is subsequently removed and the product is then alkylated with methyl iodide. After removal of the carbohydrate from the resin and filtration on silica gel, 20 mg of a colorless oil are obtained.

$R_f$=0.46, 0.34, 0.1 (OH) (PE/EtOAc=3:1vv). $C_{18}H_{28}O_6$ (340.4); FBA-MS (NBA-pos, LiCl): (m/e)=233.1 (Gly$^+$, calc.: 233.1); 347.0 ([M+Li]$^+$, calc.: 347.2); 497.2 ([M+C$_4$H$_8$$^{79}$BrO+Li]$^+$, calc.: 497.2); 499.2 ([M+C$_4$H$_8$$^{81}$BrO+Li]$^+$, calc.: 497.2).

Example 30

Methyl 2-O-methyl-6-O-heptyl-3-O-propyl-(α,β-D-glucopyranoside 166 mg (0.1 mmol) of the polymer are reacted with methyl iodide according to the general working procedure for an alkylation. The TBDPS group is subsequently removed and the product is then alkylated with heptyl iodide. After removal of the carbohydrate from the resin and filtration on silica gel, 27 mg of a colorless oil are obtained.

$R_f$=0.53, 0.42 (PE/EtOAc=3:1 v/v). $C_{18}H_{36}O_6$ (348.5); FBA-MS (NBA-pos, LiCl): (m/e)=7355.2 (22%, [M+Li]$^+$, calc.: 355.2); 369.2 (88%); 505.2 (100%, [M+C$_4$H$_8$$^{79}$BrO+Li]$^+$, calc.: 505.2); 507.2 (99%, [M+C$_4$H$_8$$^{81}$BrO+Li]$^+$, calc.: 507.2).

Example 31

Isopropyl 2-O-methyl-6-O-heptyl-3-O-propyl-α,β-D-glucopyranoside 166 mg (0.1 mmol) of the polymer are reacted with methyl iodide according to the general working procedure for an alkylation. The TBDPS group is subsequently removed and the product is then alkylated with heptyl iodide. After removal of the carbohydrate from the resin and filtration on silica gel, 21 mg of a colorless oil are obtained.

$R_f$=0.69, 0.63 (PE/EtOAc=3:1 v/v). $C_{20}H_{40}O_6$ (376.5); FBA-MS (NBA-pos, LiCl): (m/e)=533.2 (100%, [M+C$_4$H$_8$$^{79}$BrO+Li]$^+$, calc.: 533.2); 534.2 (28%, [M+C$_4$H$_8$$^{79}$BrO+Li]$^+$, —C, calc.: 534.2); 535.2 (99%, [M+C$_4$H$_8$$^{81}$BrO+Li]$^+$, calc.: 535.2); 536.2 (26%, [M+C$_4$H$_8$$^{81}$BrO+Li]$^+$, $^{13}$C, calc.: 536.2).

Example 32

Ethyl 2-O-methyl-6-O-(2'-Methoxy-5'-nitrobenzyl)-3-O-propyl-α,β-D-gluco-pyranoside 166 mg (0.1 mmol) of the polymer are reacted with methyl iodide according to the general working procedure for an alkylation. The TBDPS group is subsequently removed and the product is then alkylated with 2-methoxy-5-nitrobenzyl bromide. After removal of the carbohydrate from the resin and filtration on silica gel, 10 mg of a colorless oil are obtained.

$R_f$=0.35, 0.27 (PE/EtOAc=3:1 v/v). $C_{18}H_{36}O_6$ (429.5); FBA-MS (NBA-pos, LiCl): (m/e)=384.1 (3%, Gly$^+$, calc.: 384.2); 435.1 (22%); 436.1 (22%, [M+Li]$^+$, calc.: 436.2); 586.1 (97%, [M+C$_4$H$_8$$^{79}$BrO+Li]$^+$, calc.: 586.2); 587.1 (36%, [M+C$_4$H$_8$$^{79}$BrO+Li]$^+$, $^{13}$C, calc.: 387.2); 588.1

(100%, [M+C$_4$H$_8$$^{81}$BrO+Li]$^+$, calc.: 588.2); 589.1 (34%, [M+C$_4$H$_8$$^{81}$BrO+Li]$^+$, $^{13}$C, calc.: 589.2).

Example 33

Methyl 2-O-benzyl-6-O-isopropyl-3-O-propyl-α,β-D-glucopyranoside 166 mg (0.1 mmol) of the polymer are reacted with benzyl bromide according to the general working procedure for an alkylation. The TBDPS group is subsequently removed and the product is then alkylated with 2-bromopropane. After removal of the carbohydrate from the resin and filtration on silica gel, 9 mg of a slightly yellowish oil are obtained.

R$_f$=0.62 (PE/EtOAc=3:1 v/v). C$_{20}$H$_{32}$O$_6$ (368.5); FBA-MS (NBA-pos, LiCl): (m/e)=301.1 (83%); 373.2 (19%); 525.2 (17%, [M+C$_4$H$_8$$^{79}$BrO+Li]$^+$, calc.: 525.2); 527.2 (15%, [M+C$_4$H$_8$$^{81}$BrO+Li]$^+$, calc.: 527.2); 573.2 (13%); 575.2 (17%); 667.3 (21%); 669.3 (19%).

Example 34

Ethyl 2-O-benzyl-6-O-(4'-Cyanobenzyl)-3-O-propyl-α,β-D-glucopyranoside 166 mg (0.1 mmol) of the polymer are reacted with benzyl bromide according to the general working procedure for an alkylation. The TBDPS group is subsequently removed and the product is then alkylated with 4-cyanobenzyl bromide. After removal of the carbohydrate from the resin and filtration on silica gel, 25 mg of a colorless oil are obtained.

R$_f$=0.66, 0.55 (PE/EtOAc=3:1 v/v). C$_{26}$H$_{33}$NO$_6$ (455.6); FBA-MS (NBA-pos, LiCl): (m/e)=410.2 (5%, Gly$^+$, calc.: 410.2); 462.2 (34%, [M+Li]$^+$, calc.: 462.2); 587.2 (13%, $^{79}$Br); 589.2 (13%, $^{81}$Br); 612.2 (97%, [M+C$_4$H$_8$ BrO+Li]$^+$, calc.: 612.2); 613.2 (43%, [M+C$_4$H$_8$$^{79}$BrO+Li]$^+$, $^{13}$C, calc.: 613.2); 614.2 (100%, [M+C$_4$H$_8$$^{81}$BrO+Li]$^+$, calc.: 614.2); 615.2 (32%, [M+C$_4$H$_8$$^{81}$BrO+Li]$^+$, $^{13}$C, calc.: 615.2); 654.2 (11%, $^{79}$Br); 656.2 (13%, $^{81}$Br).

Example 35

Methyl 2-O-benzyl-6-O-heptyl-3-O-propyl-α,β-D-glucopyranoside 166 mg (0.1 mmol) of the polymer are reacted with benzyl bromide according to the general working procedure for an alkylation. The TBDPS group is subsequently removed and the product is then alkylated with heptyl iodide. After removal of the carbohydrate from the resin and filtration on silica gel, 32 mg of a colorless oil are obtained.

R$_f$=0.82, 0.76 (PE/EtOAc=3:1 v/v). C$_{24}$H$_{40}$NO$_6$ (424.6); FBA-MS (NBA-pos, LiCl): (m/e)=431.3 (14%, [M+Li]$^+$, calc.: 431.2); 581.2 (100%, [M+C$_4$H$_8$$^{79}$BrO+Li]$^+$, calc.: 581.3); 582.2 (40%, [M+C$_4$H$_8$$^{79}$BrO+Li]$^+$, $^{13}$C, calc.: 582.3); 583.2 (100%, [M+C$_4$H$_5$$^{81}$BrO+Li]$^+$, calc.: 583.3); 584.2 (30%, [M+C$_4$H$_8$$^{81}$BrO+Li]$^+$, $^{13}$C, calc.: 584.3).

Example 36

Isopropyl 2-O-benzyl-6-O-cyclohexylmethyl-3-O-propyl-α,β-D-glucopyranoside 166 mg (0.1 mmol) of the polymer are reacted with benzyl bromide according to the general working procedure for an alkylation. The TBDPS group is subsequently removed and the product is then alkylated with cyclohexylmethylene bromide. After removal of the carbohydrate from the resin and filtration on silica gel, 15 mg of a colorless oil are obtained.

R$_f$=0.85, 0.61 (PE/EtOAc=3:1 v/v). C$_{26}$H$_{42}$O$_6$ (450.6); FBA-MS (NBA-pos, LiCl): (m/e)=301.1 (59%); 443.3 (47%); 457.3 (34%, [M+Li]$^+$, calc.: 457.3); 517.2 (22%, $^{79}$Br); 519.2 (22%, Br); 607.2 (98%, [M+C$_4$H$_8$$^{79}$BrO+Li]$^+$, calc.: 607.3); 608.2 (42%, [M+C$_4$H$_8$$^{79}$BrO+Li]$^+$, $^{13}$C, calc.: 608.3); 609.2 (100%, [M+C$_4$H$_8$$^{81}$BrO+Li]$^+$, calc.: 609.3); 610.2 (34%, [M+C$_4$H$_8$$^{81}$BrO+Li]$^+$, $^{13}$C, calc.: 610.3); 669.4 (22%).

Example 37

Methyl 2-O-propyl-6-O-(4'-Cyanobenzyl)-3-O-propyl-α,β-D-glucopyranoside 166 mg (0.1 mmol) of the polymer are reacted with n-propyl iodide according to the general working procedure for an alkylation. The TBDPS group is subsequently removed and the product is then alkylated with 4-cyanobenzyl bromide. After removal of the carbohydrate from the resin and filtration on silica gel, 17 mg of a colorless oil are obtained.

R$_f$=0.63, 0.53 (PE/EtOAc=3:1 v/v). C$_{25}$H$_{31}$NO$_6$ (393.5); FBA-MS (NBA-pos, LiCl): (m/e)=382.0 (9%, $^{79}$Br); 384.0 (9%, $^{81}$Br); 400.2 (28%, [M+Li]$^+$, calc.: 400.2); 414.2 (11%); 442.2 (11%); 477.2 (9%, $^{79}$Br); 479.2 (9%, $^{81}$Br); 515.2 (9%); 550.2 (100%, [M+C$_4$H$_8$$^{79}$BrO+Li]$^+$, calc.: 550.2); 551.2 (36%, [M+C$_4$H$_8$$^{79}$BrO+Li]+, $^{13}$C, calc.: 551.2); 552.2 (98%, [M+C$_4$H$_8$$^{81}$BrO+Li]$^+$, calc.: 552.2); 553.2 (28%, [M+C$_4$H$_8$$^{81}$BrO+Li]$^+$, $^{13}$C, calc.: 553.2).

Example 38

Isopropyl 2-O-propyl-6-O-benzyl-3-O-propyl-α,β-D-glucopyranoside 166 mg (0.1 mmol) of the polymer are reacted with n-propyl iodide according to the general working procedure for an alkylation. The TBDPS group is subsequently removed and the product is then alkylated with benzyl bromide. After removal of the carbohydrate from the resin and filtration on silica gel, 18 mg of a colorless oil are obtained.

R$_f$=0.73, 0.64 (PE/EtOAc=3:1 v/v). C$_{22}$H$_{36}$O$_6$ (396.5); FBA-MS (NBA-pos, LiCl): (m/e)=229.1 (94%); 389.2 (66%); 403.2 (43%, [M+Li]$^+$, calc.: 403.3); 445.2 (19%); 505.2 (27%, $^{79}$Br); 507.2 (27%, $^{81}$Br); 553.2 (82%, [M+C$_4$H$_8$$^{79}$BrO+Li]$^+$, calc.: 553.2); 554.2 (33%, [M+C$_4$H$_8$$^{79}$BrO+Li]$^+$, $^{13}$C, calc.: 554.3); 555.2 (85%, [M+C$_4$H$_8$$^{81}$BrO+Li]$^+$, calc.: 555.3); 556.2 (26%, [M+C$_4$H$_8$$^{81}$BrO+Li]$^+$, $^{13}$C, calc.: 556.3).

Example 39

Benzyl 2-O-propyl-6-O-methyl-3-O-propyl-α,β-D-glucopyranoside 166 mg (0.1 mmol) of the polymer are reacted with n-propyl iodide according to the general working procedure for an alkylation. The TBDPS group is subsequently removed and the product is then alkylated with methyl iodide. After removal of the carbohydrate from the resin and filtration on silica gel, 149 mg of a colorless oil are obtained. The product contains still larger amounts of benzyl alcohol.

R$_f$=0.46, 0.40 (PE/EtOAc=3:1 v/v). C$_{20}$H$_{32}$O$_6$ (368.5); FBA-MS (NBA-pos, LiCl): (m/e)=261.2 (8%, Gly$^+$, calc.: 261.2); 375.2 (25%; [M+Li]$^+$, calc.: 375.2); 525.2 (15%, [M+C$_4$H$_8$$^{79}$BrO+Li]$^+$, calc.: 525.2); 526.2 (5%, [M+C$_4$H$_8$$^{79}$BrO+Li]$^+$, $^{13}$C, calc.: 526.2); 527.2 (15%, [M+C$_4$H$_8$$^{81}$BrO+Li]$^+$, calc.: 527.2); 528.2 (4%, [M+C$_4$H$_8$$^{81}$BrO+Li]$^+$, $^{13}$C, calc.: 528.2).

Example 40

Methyl 2-O-propyl-6-O-heptyl-3-O-propyl-α,β-D-glucopyranoside 166 mg (0.1 mmol) of the polymer are reacted with n-propyl iodide according to the general working procedure for an alkylation. The TBDPS group is subsequently removed and the product is then alkylated with heptyl iodide. After removal of the carbohydrate from the resin and filtration on silica gel, 24 mg of a colorless oil are obtained.

$R_f$=0.58, 0.51 (PE/EtOAc=3:1 v/v). $C_{20}H_{40}O_6$ (376.5); FBA-MS (NBA-pos, LiCl): (m/e)=383.3 (35%; [M+Li]$^+$, calc.: 383.3); 397.3 (100%); 439.3 (28%); 453.4 (48%).

Example 41

Ethyl 2-O-pentyl-6-O-heptyl-3-O-propyl-α,β-D-glucopyranoside 166 mg (0.1 mmol) of the polymer are reacted with pentyl iodide according to the general working procedure for an alkylation. The TBDPS group is subsequently removed and the product is then alkylated with heptyl iodide. After removal of the carbohydrate from the resin and filtration on silica gel, 20 mg of a colorless oil are obtained.

$R_f$=0.87, 0.80 (PE/EtOAc=3:1 v/v). $C_{23}H_{46}O_6$ (418.3); FBA-MS (NBA-pos, LiCl): (m/e)=425.3 (76%; [M+Li]$^+$, calc.: 452.3); 426.3 (19%, [M+Li]$^+$, $^{13}$C, calc.: 426.3); 575.3 (100%, [M+C$_4$H$_8$$^{79}$BrO+Li]$^+$, calc.: 575.3); 576.3 (38%, [M+C$_4$H$_8$$^{79}$BrO+Li]$^+$, $^{13}$C, calc.: 576.3); 577.3 (98%, [M+C$_4$H$_8$$^{81}$BrO+Li]$^+$, calc.: 577.3); 578.3 (28%, [M+C$_4$H$_8$$^{81}$BrO+Li]$^+$, $^{13}$C, calc.: 578.3).

Example 42

Isopropyl 2-O-pentyl-6-O-methyl-3-O-propyl-α,β-D-glucopyranoside 166 mg (0.1 mmol) of the polymer are reacted with pentyl iodide according to the general working procedure for an alkylation. The TBDPS group is subsequently removed and the product is then alkylated with methyl iodide. After removal of the carbohydrate from the resin and filtration on silica gel, 18 mg of a colorless oil are obtained.

$R_f$=0.67, 0.64 (PE/EtOAc=3:1 v/v). $C_{18}H_{36}O_6$ (348.3); FBA-MS (NBA-pos, LiCl): (m/e) 341.0 (100%); 355.1 (62%; [M+Li]$^+$, calc.: 355.2); 505.2 (83%, [M+C$_4$H$_8$$^{79}$BrO+Li]$^+$, calc.: 505.2); 506.2 (28%, [M+C$_4$H$_8$$^{79}$BrO+Li]$^+$, $^{13}$C, calc.: 506.2); 507.2 (80%, [M+C$_4$H$_8$$^{81}$BrO+Li]$^+$, calc.: 507.2); 508.2 (19%, [M+C$_4$H$_8$$^{81}$BrO+Li]$^+$, $^{13}$C, calc.: 508.2).

Example 43

Benzyl 2-O-heptyl-6-O-cyclohexylmethyl-3-O-propyl-α,β-D-glucopyranoside 166 mg (0.1 mmol) of the polymer are reacted with heptyl iodide according to the general working procedure for an alkylation. The TBDPS group is subsequently removed and the product is then alkylated with cyclohexylmethylene bromide. After removal of the carbohydrate from the resin and filtration on silica gel, 136 mg of a colorless oil are obtained. The product contains still larger amounts of benzyl alcohol.

$R_f$0=.77, 0.67 (PE/EtOAc=3:1 v/v). $C_{30}H_{50}O_6$ (506.7); FBA-MS (NBA-pos, LiCl): (m/e)=285.2 (65%); 309.2 (100%); 339.2 (45%); 399.3 (39%, Gly$^+$, calc.: 399.3); 451.3 (48%); 513.3 (22%; [M+Li]$^+$, calc.: 513.3); 663.3 (24%, [M+C$_4$H$_8$$^{79}$BrO+Li]$^+$, calc.: 663.3); 665.3 (34%, [M+C$_4$H$_8$$^{81}$BrO+Li]$^+$, calc.: 665.3).

Example 44

Methyl 2-O-heptyl-6-O-benzyl-3-O-propyl-α,β-D-glucopyranoside 166 mg (0.1 mmol) of the polymer are reacted with heptyl iodide according to the general working procedure for an alkylation. The TBDPS group is subsequently removed and the product is then alkylated with benzyl bromide. After removal of the carbohydrate from the resin and filtration on silica gel, 32 mg of a colorless oil are obtained.

$R_f$=0.86, 0.77 (PE/EtOAc=3:1 v/v). $C_{24}H_{40}O_6$ (424.6); FBA-MS (NBA-pos, LiCl): (m/e)=341.2 (7%; [6-OH+Li]$^+$, calc.: 341.3); 431.3 (13%, [M+Li]$^+$, calc.: 413.3); 459.2 (15%, $^{79}$Br); 461.3 (14%, $^{81}$Br); 491.2 (16%, [6-OH+C$_4$H$_8$$^{79}$BrO+Li]$^+$, calc.: 491.3); 493.2 (15%,. [6-OH+C$_4$H$_8$$^{81}$BrO+Li]$^+$, calc.: 493.3); 581.2 (95%, [M+C$_4$H$_8$$^{79}$BrO+Li]$^+$, calc.: 581.3); 582.3 (38%, [M+C$_4$H$_8$$^{79}$BrO+Li]$^+$, $^{13}$C, calc.: 582.3); 583.2 (100%, [M+C$_4$H$_8$$^{79}$BrO+Li]$^+$, calc.: 583.2); 584.2 (31%, [M+C$_4$H$_8$$^{81}$BrO+Li]$^+$, $^{13}$C, calc.: 584.3); 589.2 (68%, $^{79}$Br); 590.2 (25%, $^{79}$Br, $^{13}$C); 591.2 (64%, $^{81}$Br); 592.2 (19%, $^{81}$Br, $^{13}$C).

Example 45

Isopropyl 2-O-heptyl6-O-(4'-Cyanobenzyl)-3-O-propyl-D-α,β-glucopyranoside 166 mg (0.1 mmol) of the polymer are reacted with heptyl iodide according to the general working procedure for an alkylation. The TBDPS group is subsequently removed and the product is then alkylated with 4-cyanobenzyl bromide. After removal of the carbohydrate from the resin and filtration on silica gel, 21 mg of a colorless oil are obtained.

$R_f$=0.76, 0.74 (PE/EtOAc=3:1 v/v). $C_{27}H_{43}NO_6$ (477.6); FBA-MS (NBA-pos, LiCl): (m/e)=408.2 (10%; Gly$^+$, calc.: 408.2); 470.3 (20%); 484.3 (21%, [M+Li]$^+$, calc.: 484.3); 582.4 (22%); 617.3 (24%, $^{79}$Br); 619.3 (24%, $^{81}$Br); 634.2 (85%, [M+C$_4$H$_8$$^{79}$BrO+Li]$^+$, calc.: 634.3); 635.2 (38%, [M+C$_4$H$_8$$^{79}$BrO+Li]$^+$, $^{13}$C, calc.: 635.3); 636.2 (92%, [M+C$_4$H$_8$$^{81}$BrO+Li]$^+$, calc.: 636.3); 637.2 (31%, [M+C$_4$H$_8$$^{81}$BrO+Li]$^+$, $^{13}$C, calc.: 637.3).

Example 46

Methyl 2-O-heptyl-6-O-isopropyl-3-O-propyl-α,β-D-glucopyranoside 166 mg (0.1 mmol) of the polymer are reacted with heptyl iodide according to the general working procedure for an alkylation. The TBDPS group is subsequently removed and the product is then alkylated with n-propyl iodide. After removal of the carbohydrate from the resin and filtration on silica gel, 13 mg of a colorless, oil are obtained.

$R_f$=0.80, 0.72 (PE/EtOAc=3:1 v/v). $C_{20}H_{40}O_6$ (376.5); FBA-MS (NBA-pos, LiCl): (m/e)=383.3 (36%, [M+Li]$^+$, calc.: 383.3); 397.3 (76%); 533.3 (19%, [M+C$_4$H$_8$$^{79}$BrO+Li]$^+$, calc.: 533.3); 535.3 (16%, [M+C$_4$H$_8$$^{81}$BrO+Li]$^+$, calc.: 535.3); 611.2 (40%).

Example 47

Methyl 2-O-heptyl-6-O-(4'-Bromobenzyl)-3-O-propyl-D-glucopyranoside 166 mg (0.1 mmol) of the polymer are reacted with heptyl iodide according to the general working procedure for an alkylation. The TBDPS group is subsequently removed and the product is then alkylated with 4-bromobenzyl bromide. After removal of the carbohydrate from the resin and filtration on silica gel, 16 mg of a colorless oil are obtained.

$R_f$=0.84, 0.73 (PE/EtOAc=3:1 v/v). $C_{24}H_{39}BrO_6$ (503.5); FBA-MS (NBA-pos, LiCl): (m/e)=453.4 (100%); 509.2 (41%, [M+Li]$^+$, $^{79}$Br, calc.: 509.3); 511.2 (37%, [M+Li]$^+$, $^{81}$Br, calc.: 511.3); 523.2 (84%, $^{79}$Br); 525.2 (83%, Br); 659.0 (34%, [M+C$_4$H$_8$$^{79}$BrO+Li]$^+$, Br, calc.: 659.3); 661.0 (59%, [M+C$_4$H$_8$$^{79}$BrO+Li]$^+$, $^{81}$Br, calc.: 661.3); 663.0 (31%, [M+C$_4$H$_8$$^{81}$BrO+Li]$^+$, Br, calc.: 663.3).

Example 48

Methyl 2-O-ethyl-6-O-benzyl-3-O-propyl-α,β-D-glucopyranoside 166 mg (0.1 mmol) of the polymer are reacted with ethyl iodide according to the general working procedure for an alkylation. The TBDPS group is subsequently removed and the product is then alkylated with benzyl bromide. After removal of the carbohydrate from the resin and filtration on silica gel, 22 mg of a colorless oil are obtained.

$R_f$=0.82, 0.77 (PE/EtOAc=3:1 v/v). $C_{19}H_{30}O_6$ (354.4); FBA-MS (NBA-pos, LiCl): (m/e)=271.2 (7%, [6-OH+Li]$^+$, calc.: 271.2); 361.3 (15%, [M+Li]$^+$, calc.: 361.2); 421.2 (11%, [6-OH+C$_4$H$_8$$^{79}$BrO+Li]$^+$, calc.: 421.2); 423.2 (9%, [6-OH+C$_4$H$_8$$^{81}$BrO+Li]$^+$, calc.: 423.2); 449.3 (38%); 451.3 (41%); 511.3 (96%, [M+C$_4$H$_8$$^{79}$BrO+Li]$^+$, calc.: 511.2); 512.3 (36%, [M+C$_4$H$_8$$^{79}$BrO+Li]$^+$, $^{13}$C, calc.: 512.2); 513.3 (100%, [M+C$_4$H$_8$$^{81}$BrO+Li]$^+$, calc.: 513.2); 514.3 (26%, [M+C$_4$H$_8$$^{81}$BrO+Li]$^+$, $^{13}$C, calc.: 514.2).

Example 49

Methyl 2-O-ethyl-6-O-(2'-Methoxy-5'-nitrobenzyl )-3-O-propyl-α,β-D-glucopyranoside 166 mg (0.1 mmol) of the polymer are reacted with ethyl iodide according to the general working procedure for an alkylation. The TBDPS group is subsequently removed and the product is then alkylated with 2-methoxy-5-nitrobenzyl bromide. After removal of the carbohydrate from the resin and filtration on silica gel, 15 mg of a colorless oil are obtained.

$R_f$=0.43 (PE/EtOAc=3:1 v/v). $C_{20}H_{31}NO_9$ (429.5); FBA-MS (NBA-pos, LiCl): (m/e)=436.2 (9%, [M+Li]$^+$, calc.: 436.2); 586.1 (95%, [M+C$_4$H$_8$$^{79}$BrO+Li]$^+$, calc.: 586.2); 587.1 (35%, [M+C$_4$H$_8$$^{79}$BrO+Li]$^+$, $^{13}$C, calc.: 587.2); 588.1 (100%; [M+C$_4$H$_8$$^{81}$BrO+Li]$^+$, calc.: 588.2); 588.1 (28%, [M+C$_4$H$_8$$^{81}$BrO+Li]$^+$, $^{13}$C, calc.: 589.2).

Example 50

Benzyl 2-O-ethyl-6-O-heptyl-3-O-propyl-α,β-D-glucopyranoside 166 mg (0.1 mmol) of the polymer are reacted with ethyl iodide according to the general working procedure for an alkylation. The TBDPS group is subsequently removed and the product is then alkylated with methyl iodide. After removal of the carbohydrate from the resin and filtration on silica gel, 116 mg of a colorless oil are obtained. The product contains still larger amounts of benzyl alcohol.

$R_f$=0.61, 0.54 (PE/EtOAc=3:1 v/v). $C_{25}H_{42}O_6$ (438.6); FBA-MS (NBA-pos, LiCl): (m/e)=445.3 (29%, [M+Li]$^+$, calc.: 445.3); 595.3 (100%, [M+C$_4$H$_8$$^{79}$BrO+Li]$^+$, calc.: 595.3); 596.3 (40%, [M+C$_4$H$_8$$^{79}$BrO+Li]$^+$, $^{13}$C, calc.: 596.3); 597.3 (98%; [M+C$_4$H$_8$$^{81}$BrO+Li]$^+$, calc.: 597.3); 598.3 (31 %, [M+C$_4$H$_8$$^{81}$BrO+Li]$^+$, $^{13}$C calc.: 595.3).

Example 51

Ethyl 2-O-(2'-Cyanobenzyl)-6-O-heptyl-3-O-propyl-α,β-D-glucopyranoside 166 mg (0.1 mmol) of the polymer are reacted with 2-cyanobenzyl bromide according to the general working procedure for an alkylation. The TBDPS group is subsequently removed and the product is then alkylated with heptyl iodide. After removal of the carbohydrate from the resin and filtration on silica gel, 26 mg of a colorless oil are obtained.

$R_f$=0.78, 0.70 (PE/EtOAc=3:1 v/v). $C_{26}H_{41}NO_6$ (463.6); FBA-MS (NBA-pos, LiCl): (m/e)=418.2 (12%, Gly$^+$, calc.: 418.3); 470.3 (100%, [M+Li]$^+$, calc.: 470.3); 471.3 (32%, [M+Li]$^+$, $^{13}$C, calc.: 471.3); 568.4 (78%); 603.3 (15%, $^{79}$Br); 605.3 (15%, $^{79}$Br); 620.2 (57%, [M+C$_4$H$_8$$^{79}$BrO+Li]$^+$, calc.: 620.3); 621.2 (25%, [M+C$_4$H$_8$$^{79}$BrO+Li]$^+$, $^{13}$C, calc.: 621.3); 622.2 (55%; [M+C$_4$H$_8$$^{81}$BrO+Li]$^+$, calc.: 622.3); 623.2 (19%, [M+C$_4$H$_8$$^{81}$BrO+Li]$^+$, $^{13}$C, calc.: 623.3).

Example 52

Isopropyl 2-O-(2'-Cyanobenzyl)-6-O-methyl-3-O-propyl-α,β-D-glucopyranoside 166 mg (0.1 mmol) of the polymer are reacted with 2-cyanobenzyl bromide according to the general working procedure for an alkylation. The TBDPS group is subsequently removed and the product is then alkylated with methyl iodide. After removal of the carbohydrate from the resin and filtration on silica gel, 21 mg of a colorless oil are obtained.

$R_f$=0.52, 0.47 (PE/EtOAc=3:1 v/v). $C_{21}H_{31}NO_6$ (393.5); FBA-MS (NBA-pos, LiCl): (m/e)=334.1 (8%, Gly$^+$, calc.: 334.2); 386.2 (12%); 400.2 (27%, [M+Li]$^+$, calc.: 400.2); 414.2 (12%); 449.2 (10%, $^{79}$Br); 451.3 (10%; $^{81}$Br); 550.2 (98%, [M+C$_4$H$_8$$^{79}$BrO+Li]$^+$, calc.: 550.2); 551.2 (36%, [M+C$_4$H$_8$$^{79}$BrO+Li]$^+$, $^{13}$C, calc.: 551.2); 552.2 (100%; [M+C$_4$H$_8$$^{81}$BrO+Li]$^+$, calc.: 552.2): 553.2 (28%, [M+C$_4$H$_8$$^{81}$BrO+Li]$^+$, $^{13}$C calc.: 553.2).

Example 53

Methyl 2,4-di-O-benzyl-6-O-methyl-3-O-propyl-α,β-D-glucopyranoside 166 mg (0.1 mmol) of the polymer are converted into the derivative analogously to the experiments described above. For the removal of the 1-ethoxyethyl protective group, the carbohydrate matrix is suspended in a mixture of 4 ml of dioxane, 0.4 ml of alcohol (methanol, propanol, octanol or benzyl alcohol) and a spatula-tipful of pyridinium toluene4-sulfonate. The syringe is then closed with a plastic cap and shaken at room temp. for 16 h. Following this, the resin is washed five times with 3 ml of dioxane p.a. each time and twice with 3 ml of DMF.

After the removal of the 1-ethoxyethyl protective group, the 4-position is alkylated with benzyl bromide and the carbohydrate is removed from the resin. 12–16 mg of a colorless oil are obtained. As all crude products contain identical components according to TLC, HPLC and MS, they are combined and purified by chromatography on silica gel using petroleum ether/ethyl acetate (12:1).

$C_{25}H_{34}O_6$ (430.6); FAB-MS (NBA-pos, LiCl): (m/e)= 437.1 (100%, [M+Li]$^+$, calc.: 437.2); 438.1 (28%, [M+Li]$^+$, $^{13}$C, calc.: 438.2); 513.3 (28%, [C$_{31}$H$_{38}$O$_6$+Li]$^+$, 6-OBn, calc: 506.3).

400 MHz-$^1$H-NMR (CDCl$_3$): δ [ppm]=7.50–7.25 (m, 10H, Ph); 4.86 (d, 1H, J$_{gem}$=10.86 Hz, CH$_2$Ph); 4.77 (d, 1H, J$_{gem}$=12.32, CH$_2$Ph); 4.60 (d,. 1H, J$_{gem}$=12.03 Hz, CH$_2$Ph); 4.56 (d, 1H, J$_{gem}$=10.86 Hz, CH$_2$Ph); 4.52 (d, 1H, J$_{2,1}$=3.81 Hz, H-1); 3.87–3.24 (m, 8H, H-2, H-3, H4, H-5, H-6a/b, OCH$_2$Pr); 3.32, 3.30 (2×s, 6H, OCH$_3$); 1.66–1.61 (m, 2H, OCH$_2$CH$_2$Pr); 0.92 (t, J$_{gem}$=7.48 Hz, CH$_3$Pr).

6-Benzyl Derivative:

400 MHz-$^1$H-NMR (CDCl$_3$): δ [ppm]=7.51–7.26 (m, 15H, Ph); 4.86 (d, 1H, J$_{gem}$=11.15 Hz, CH$_2$Ph); 4.80 (d, 1H, J$_{gem}$=10.57 Hz, CH$_2$Ph); 4.67 (d, 1H, J$_{gem}$=11.15Hz, CH$_2$Ph); 4.614.54 (m, 2H, CH$_2$Ph); 4.50 (d, 1H, J$_{gem}$=10.57 Hz, CH$_2$Ph); 4.25–4.18 (m, 3H, H-1 & OCH$_2$Pr); 3.80–3.29 (m, 6H, H-2, H-3, H4, H-5, H-6a/b); 3.54 (s, 3H, OCH$_3$); 1.68–1.60 (m, 2H, OCH$_2$CH$_2$Pr); 0.91–0.86 (m, 3H, CH$_3$Pr).

Example 54

Methyl 2-O-benzyl-4-O-(2'-Bromo-1'-ethoxy)ethyl-6-O-methyl-3-O-propyl-α/β-D-glucopyranoside 166 mg (0.1 mmol) of the polymer are converted into the derivative analogously to the experiments described above. By treatment of the resin with various combinations of solvents and IM citric acid (4 ml of DMF+0.4 ml of 1M citric acid; 4 ml of DMF+0.4 ml of 1M citric acid+4 h ultrasound; 4 ml of DMF+0.04 ml of 1M citric acid; 4 ml of dioxane+0.04 ml of 1M citric acid; 4 ml of CH$_2$Cl$_2$+1 ml of acetone+0.1 ml of 1M citric acid), it is attempted to remove the 1-ethoxyethyl protective group.

The resin is then subjected to a benzylation and the carbohydrate is removed from the polymeric support. 13–17 mg of a colorless oil are obtained. As all crude products contain identical components according to TLC, HPLC and MS, they are combined and purified by chromatography on silica gel using petroleum ether/ethyl acetate (8:1). C$_{22}$H$_{35}$BrO$_7$ (491.4).

FAB-MS (NBA-pos, LiCl) of crude product: (m/e)=497.4 (100%, [M+Li]$^+$, $^{79}$Br, calc.: 497.2); 498.4 (31%, [M+Li]$^+$, $^{79}$Br, C, calc. 498.2); 499.4 (98%, [M+Li]$^+$, $^{81}$Br, calc.: 499.2); 500.4 (22%, [M+Li]$^+$, $^{81}$Br, $^{13}$C, calc.: 500.2); 573.2 (28%, [C$_{28}$H$_{39}$$^{79}$BrO$_7$+Li]$^+$6-OBn, calc.: 573.3); 575.2 (31%, [C$_{28}$H$_{39}$ BrO$_7$+Li]$^+$6-OBn, calc.: 575.3).

1st Diastereomer:

400 MHz-$^1$H-NMR (CDCl$_3$): δ [ppm]=7.33–7.25 (m, 5H, Ph); 4.87–4.84 (m, 1H, CHCH$_2$EEBr); 4.72 (d, 1H, J$_{gem}$=12.03 Hz, OCH$_2$Ph); 4.64 (d, 1H, J$_{2,1}$=3.82 Hz, H-1); 4.56 (d, 1H, J$_{gem}$=12.03 Hz, OCH$_2$Ph); 3.90–3.85 (m,1H, OCH$_2$); 3.75–3.54 (m, 6H, H-2, H-6a/b, OCH$_2$); 3.52 (s, 3H, OCH$_3$); 3.48–3.31 (m, 5H, H-3, H4, H-5 & CH$_2$Br EEBr); 3.36 (s, 3H, OCH$_3$); 1.63–1.57 (m, 2H, OCH$_2$CH$_2$Pr); 1.25–1.18 (m, 3H, OCH$_2$CH$_3$EEBr &); 0.89 (t, J$_{gem}$=7.49 Hz, CH$_3$Pr).

400 MHz-$^1$H-NMR (CDCl$_3$): δ [ppm]=7.34–7.26 (m, 5H, Ph); 4.97–4.95 (m, 1H, CHCH$_2$EEBr); 4.72 (d, 1H, J$_{gem}$=12.03 Hz, OCH$_2$Ph); 4.66 (d, 1H, J$_{2,1}$=3.52 Hz, H-1); 4.56 (d, 1H, J$_{gem}$=12.03 Hz, OCH$_2$Ph); 3.93–3.87 (m, 1H, OCH$_2$); 3.70–3.57 (m, 6H, H-2, H-6a/b, OCH$_2$); 3.54–3.30 (m, 5H, H-3, H-4, H-5 & CH$_2$Br EEBr); 3.49 (s, 3H, OCH$_3$); 3.36 (s, 3H, OCH$_3$); 1.64–1.59 (m, 2H, OCH$_2$CH$_2$Pr); 1.23–1.19 (m, 3H, OCH$_2$CH$_3$EEBr &); 0.89 (t, J$_{gem}$=6.75 Hz, CH$_3$Pr). HPLC (gradient 90/10):

During chromatography, the derivative benzylated in the 6-position, methyl 2,6-di-O-benzyl4-O-(2-bromo-1-ethoxy)-ethyl-3-O-propyl-Dgluco-pyranoside, which has already been observed in the FAB mass spectrum, can be separated off.

C$_{28}$H$_{39}$BrO$_7$ (567.51); 400 MHz-$^1$H-NMR (CDCl$_3$): δ [ppm]=7.33–7.25 (m, 10H, Ph); 4.96–4.49 (m, 6H, H-1, OCH$_2$Ph & CHCH$_2$Br EEBr); 3.92–3.10 (m, 12H, H-2, H-3, H4, H-5, H-6a/b, OCH$_2$ & CH$_2$Br EEBr), 3.36, 3.33 (s, 3H, OCH$_3$); 1.64–1.54 (m, 2H, OCH$_2$CH$_2$Pr); 1.25–1.19 (m, 3H, OCH$_2$CH$_3$EEBr &); 0.89 (t, J$_{gem}$=7.49 Hz, CH$_3$ Pr).

Example 55

Methyl 2-O-benzyl4-O-tert-butyloxycarbonylmethyl-6-O-methyl-3-O-propyl-α/β-D-glucopyranoside 166 mg (0.1 mmol) of the polymer are reacted with benzyl bromide according to the general working procedure for an alkylation. The TBDPS group is subsequently removed and the product is then alkylated with methyl iodide. After the 1-ethoxyethyl protective group has been removed, the product is reacted with tert-butyl bromoacetate. After removal of the carbohydrate from the resin and filtration on silica gel, 23 mg of a colorless oil are obtained. R$_f$=0.64, 0.59 (PE/EtOAc=3:1 v/v). C$_{24}$H$_{38}$O$_8$ (454.6).

FAB-MS (NBA-pos, LiCl): (m/e)=461.3 (75%, [M+Li]$^+$, calc.: 461.3); 462.3 (23%, [M+Li]$^+$, $^{13}$C, calc.: 462.3); 561.3 (100%, [C$_{29}$H$_{46}$O$_{10}$+Li]$^+$6-OCH$_2$CO$_2$tBu, calc.: 561.3); 562.3 (33%, [C$_{29}$H$_{46}$O$_{10}$+Li]$^+$, $^{13}$C, calc.: 562.3).

Example 56

Library containing 1,2,6-functionalized glucose derivatives (compound of the formula I where X is equal to O, R$^3$ is equal to propyl and R$^4$ is equal to hydrogen).

80 mg of the loaded resin were functionalized according to the general working procedures (Table 1).

Example 57

Library containing 1,2,4,6-functionalized glucose derivatives (compound of the formula I where X is equal to O, R$^1$ is equal to methyl, R$^3$ is equal to propyl).

80 mg of the loaded resin are functionalized according to the general working procedures. The alkylation in the 4-position takes place by use of tert-butyl bromoacetate.

| Compound | R$^2$ | R$^4$ | R$^5$ | MS analysis (m/e) (FAB, NBA + LiCl) |
|---|---|---|---|---|
| 1 | Bn | Bn | Me | 437.1 |
| 2 | Bn | CH$_2$CO$_2$tB | Me | 461.3 |

TABLE 1

| Compound | R$^2$ | R$^5$ | R$^1$ | MS analysis (m/e) (FAB, NBA + LiCl) |
|---|---|---|---|---|
| 1 | Me | Bn | Me | 347.2 |
| 2 | Me | Me | Bn | 347.2 |
| 3 | Me | Hep | Me | 355.2 |
| 4 | Me | Hep | iPr | 383.2 |
| 5 | Me | MNBnEt | Et | 436.1 |
| 6 | Bn | iPr | Me | 375.1 |
| 7 | Bn | Cbn | Et | 462.2 |
| 8 | Bn | Hep | Me | 431.3 |
| 9 | Bn | cHex | iPr | 457.3 |
| 10 | Bn | iBu | Me | 389.2 |
| 11 | Pr | Cbn | Me | 400.2 |
| 12 | Pr | Bn | iPr | 403.2 |
| 13 | Pr | Me | Bn | 375.2 |
| 14 | Pr | Hep | Me | 383.3 |
| 15 | Pent | iPr | Me | 355.2 |

TABLE 1-continued

| Compound | R² | R⁵ | R¹ | MS analysis (m/e) (FAB, NBA + LiCl) |
|---|---|---|---|---|
| 16 | Pent | Hep | Et | 425.3 |
| 17 | Pent | Me | iPr | 355.3 |
| 18 | Hep | cHex | Bn | 513.3 |
| 19 | Hep | Bn | Me | 431.3 |
| 20 | Hep | Cbn | iPr | 484.3 |
| 21 | Hep | iPr | Me | 383.3 |
| 22 | Hep | BrBn | Me | 509.2 |
| 23 | Et | Bn | Me | 361.3 |
| 24 | Et | MNBn | Me | 436.2 |
| 25 | Et | Hep | Bn | 445.3 |
| 26 | Cbr | iPr | Me | 400.3 |
| 27 | Cbr | Hep | Et | 470.3 |
| 28 | Cbr | Me | iPr | 400.2 |

Abbreviations:
MNBn = 2-methoxy-5-nitrobenzyl,
CBn = o-cyanobenzyl,
Pent = pentyl,
cHex = cyclohexylmethylene.

Example 58

Methyl S-(6'-O-tert-Butyldiphenylsilyl-3',4'-O-isopropylidene-β-D-galactopyranosyl-2'-O-methyl)-4-mercaptobutyrate (32)

A solution of 3.0 g (5.2 mmol) of 19 in 30 ml of THF is stirred at 0° C., for 45 min with 0.6 g (5.3 mmol) of potassium tert-butylate under an argon atmosphere and then treated with 0.38 ml (6.0 mmol) of methyl iodide. As only slight conversion is discernible after a few hours by thin-layer chromatographic checking, the same amount of reagents is added again. The precipitating solid is dissolved by addition of 15 ml of DMF. After stirring for 12 h, the solution is concentrated in vacuo, and the residue is codistilled with toluene and purified by flash chromatography on silica gel (column 18×6 cm, eluent petroleum ether/ethyl acetate 10:1).

Yield 1.8 g (59%), colorless oil, $[\alpha]_D^{25}$=−15.90 (c=1, CHCl$_3$); $R_F$=0.34 (petroleum ether/ethyl acetate 8:1).

400MHz-$^1$H-NMR (CDCl$_3$): δ [ppm]=7.69–7.66; 7.41–7.33 (m, 10H, SiPh$_2$), 4.28 (d, 1 H, $J_{1,2}$=9.7 Hz, 1'-H), 4.27 (dd, 1H, $J_{4,3}$=5.5 Hz, $J_{4,5}$=2.3 Hz, 4'-H), 4.09 (dd, 1H, $J_{3,2}$=7.0 Hz, $J_{3,4}$=5.6 Hz, 3'-H), 3.89 (m, 2H, 6'-H$_{a,b}$), 3.79 (ddd, 1H, $J_{5,4}$=2.3 Hz, $J_{5,6}$≈$J_{5,6b}$=6.2 Hz, 5'-H), 3.59; 3.55 (2s, 6H, OCH$_3$), 3.17 (dd, 1H, $J_{2,1}$=10.0 Hz, $J_{2,3}$=6.8 Hz, 2'-H), 2.77 (dt, 1H, $J_{vic}$=6.5 Hz, $J_{gem}$=12.9 Hz, SCH$_a$), 2.64 (dt, 1H, $J_{vic}$=6.5 Hz, $J_{gem}$=12.9 Hz, SCH$_b$), 2.39 (m$_c$, 2H, CH$_2$COOMe), 1.91 (m$_c$, 2H, SCH$_2$CH$_2$), 1.50; 1.33 (2s, 6H, C(CH$_3$)$_2$), 1.03 (s, 9H, SiC(CH$_3$)$_3$. 100.6 MHz-$^{13}$C-NMR (CDCl$_3$); δ [ppm]=173.3 (CO), 135.6; 135.5 (C$_p$-SiPh$_2$), 133.5; 133.4 (C$_e$-SiPh$_2$), 129.7; 127.7; 127.6 (C$_{o,m}$-SiPh2), 109.7 (C(CH$_3$)$_2$), 83.6; 81.8; 79.4; 76.8; 73.4; 62.8 (C-1'–C-6'), 59.7 (OCH$_3$), 51.4 (COOCH$_3$), 32.7 (SCH$_2$), 29.6 (CH$_2$COOMe), 28.0 (C(CH$_3$)$_2$), 26.7 (SiC(CH$_3$)$_3$), 26.2 (C(CH$_3$)$_2$), 25.0 (SCH$_2$CH$_2$),19.2 (SiC(CH$_3$)$_3$).

| C$_{31}$H$_{44}$O$_7$SSi | (588.8) | Calc.: | C 63.23 | H 7.53 | S 5.44 |
|---|---|---|---|---|---|
| | | Found: | C 63.09 | H 7.61 | S 5.41 |

Example 59

S-(6'-O-tert-Butyldiphenylsilyl-3',4'-O-isopropylidene-β-D-galactopyranosyl)-4-mercaptobutyric Acid, Polymer-bonded (33, 34)

The thiogalactoside 19 is coupled to 0.390 g (0.6 mmol) of aminomethylpolystyrene to give 33 according to the general procedure.

Loading according to the sulfur content of the elemental analysis: 0.77–0.81 mmol/g.

The thiogalactoside 19 is coupled to 2.0 g (0.56 mmol) of Tentagel to give 34 according to the general procedure.

Loading (gravimetric): 0.20 mmol/g.

Example 60

S-(6'-O-tert-Butyldiphenylsilyl-3',4'-O-isopropylidene-2'-O-β-D-galactopyranosyl)4-mercaptobutyric Acid, Polymer-bonded (35, 36)

The 2-O-methylthiogalactoside 32 is coupled to 1.0 g (0.6 mmol) of aminomethylpolystyrene to give 35 according to the general working procedure.

Loading according to the sulfur content of the elemental analysis: 0.78 mmol/g.

The 2-O-methylthiogalactoside 32 is coupled to 2.0 g (0.56 mmol) of Tentagel to give 36 according to the general working procedure.

Loading (gravimetric): 0.27 mmol/g.

Example 61

Methyl 6-O-tert-Butyldiphenylsilyl-3,4-O-isopropylidene-2-O-methyl-α/β-D-galactopyranoside a) by removal of 35: According to the general procedure, 400 mg (0.312 mmol) of 79 are treated with methanol as an alcohol. Purification is carried out by flash chromatography on silica gel (column 18×4 cm, eluent petroleum ether/ethyl acetate 8:1).

Yield 70 mg (24%) of α-anomer, colorless oil; 134 mg (46%) of β-anomer, colorless oil. By washing the resin again and combining the washings with the mixed fractions, a further 43 mg (15%) are obtained as an anomer mixture.

b) by removal of 36: According to the general procedure, 80 is glycosylated using methanol as an alcohol. Purification is carried out by flash chromatography on silica gel (column 18×4 cm, eluent petroleum ether/ethyl acetate 8:1).

Yield 12 mg (4%) of c-anomer, colorless oil; 44 mg (15%) of β-anomer, colorless oil.

In addition, 47 mg (17%) of hydrolysis sugar are isolated as an anomer mixture.

c) by alkylation with sodium hydride/methyl iodide: 370 mg (0.3 mmol) of 33 are suspended in 15 ml of DMF/THF (1:1) and preliminarily shaken at room temp. under an argon atmosphere for 20 min with 0.090 g (3.0 mmol) of sodium hydride (80% in mineral oil). After addition of 0.19 ml (3.0 mmol) of methyl iodide, the mixture is shaken for 12 h, and the resin is filtered off after addition of 5 ml of methanol and washed a number of times with DMF. Removal is carried out according to the general procedure using methanol as an alcohol. Purification is carried out by flash chromatography on silica gel (column 15×3 cm, eluent petroleum ether/ethyl acetate 8:1).

Yield 92 mg (32%) of a-anomer, clear oil; 43 mg (15%) of β-anomer, clear oil.

In addition, 14 mg (5%) of α-anomer and 32 mg (11 %) of P-anomer of the nonalkylated methyl glycoside are isolated.

d) by alkylation with KOtBu/methyl iodide: as under c) at 0° C., 4 h.

Yield 55 mg (19%), clear oil, anomer mixture.

Example 62

Methyl 6-O-tert-Butyldiphenylsilyl-3,4-O-isopropylidene-2-O-benzyl-β-D-galactopyranoside a) by alkylation of 33 with sodium hydride/benzyl bromide: 768 mg (0.6 mmol) of 33 are reacted as above with 180 mg (6.0 mmol) of sodium hydride (80% in mineral oil) and 0.72 ml (6.0 mmol) of benzyl bromide at room temp. under an argon atmosphere for 12 h and removed. Purification is carried out by flash chromatography on silica gel (column 15×4 cm, eluent petroleum ether/ethyl acetate 15:1).

Yield 67 mg (20%) of a-anomer, clear oil; 26 mg (8%) of β-anomer, turbid oil.

In addition, 4 mg (2%) are obtained as an anomer mixture.

b) by alkylation of 34 with sodium hydride/benzyl bromide: 2.5 g (0.5 mmol) of 34 are reacted as above with 900 mg (30.0 mmol) of sodium hydride (80% in mineral oil) and 3.6 ml (30.0 mmol) of benzyl bromide at room temp. under an argon atmosphere for 12 h and removed. Purification is carried out by flash chromatography on silica gel (column 18×3 cm, eluent petroleum ether/ethyl acetate 10:1).

Yield 100 mg (37%) of anomer mixture, yellow oil.

c) by alkylation with potassium tert-butoxide/benzyl bromide: 640:mg (0.5 mmol) of 33 are swollen in 20 ml of DMF. After addition of 0.56 g (5.0 mmol) of potassium tert-butoxide, the mixture is shaken under an argon atmosphere for 20 min. 0.59 ml (5.0 mmol) of benzyl bromide and 0.22 g (0.6 mmol) of tetrabutylammonium iodide are then added and the mixture is shaken for 16 h. 20 ml of methanol are added, and the resin is filtered off and washed a number of times with DMF and absol. THF. The resin is dried in vacuo. Removal is carried out according to the general procedure with methanol as an alcohol. Purification is carried out by flash chromatography on silica gel (column 18×3 cm, eluent petroleum ether/ethyl acetate 8:1).

Yield 124 mg (44%) of a-anomer, clear oil; 22 mg (8%) of β-anomer, colorless oil.

d) by alkylation with phosphazene base $P_4$-t-Bu/benzyl bromide: 384 mg (0.33 mmol) of 33 are swollen in 10 ml of DMF and cooled to 0° C. under an argon atmosphere. 1.32 ml (1.32 mmol, 1 M in n-hexane) of $P_4$-tert-Bu are added and the mixture is shaken. After 15 min, 0.59 ml (5.0 mmol) of benzyl bromide is added and the mixture is shaken at 0° C. for 16 h. The resin is filtered off and washed a number of times with DMF and absol. THF. After drying in vacuo, the compound is removed from the support according to the general procedure using methanol as an alcohol. Purification is carried out by flash chromatography on silica gel (column 18×3 cm, eluent petroleum ether/ethyl acetate 10:1).

Yield 163 mg (85%) of anomer mixture (α,β about 5:1), colorless oil.

α-Anomer: $[α]_D^{25}$=+44.9 (c=1, CHCl$_3$); R$_F$=0.20 (petroleum ether/ethyl acetate 8:1)

β-Anomer: $[α]_D^{25}$=+17.2 (c=1, CHCl$_3$); R$_F$=0.30 (petroleum ether/ethyl acetate 8:1).

Example 63

Methyl 2-O-(o-Cyanobenzyl)-6-O-tert-butyldiphenylsilyl-3,4-O-isopropylidene-α/β-D-galactopyranoside 400 mg (0.312 mmol) of 33 are reacted with o-cyanobenzyl bromide according to the general working procedure (variant A) and removed with methanol under glycosylating conditions. The crude product is purified by flash chromatography on silica gel (column 20×2 cm, eluent petroleum ether/ethyl acetate 12:1).

α-Anomer:
Yield 26 mg (14%), colorless oil, $[α]_D^{25}$=+50.5 (c=1.0, CHCl$_3$); R$_F$=0.39 (petroleum ether/ethyl acetate 4:1), HPLC (column C, gradient 1): 20.91 min.

β-Anomer:
Yield 12 mg (7%), colorless oil, $[α]_D^{25}$=+19.6 (c=0.33, CHCl$_3$); R$_F$=0.46 (petroleum ether/ethyl acetate 4:1), HPLC (column C, gradient 1): 20.91 min.

Example 64

Methyl 2-O-(p-Bromobenzyl)-6-O-tert-butyldiphenylsilyl-3,4-O-isopropylidene-α/β-D-galactopyranoside 400 mg (0.312 mmol) of 33 are reacted with p-bromobenzyl bromide according to the general working procedure and the product is removed under glycosylating conditions using methanol. The crude product is purified by flash chromatography on silica gel (column 20×2 cm, eluent petroleum ether/ethyl acetate 12:1).

α-Anomer:
Yield 12 mg (6%), colorless oil, $[α]_D^{25}$=+38.4 (c=1.0, CHCl$_3$); R$_F$=0.17 (petroleum ether/ethyl acetate 12:1), HPLC (column C, gradient. 1): 22.13 min.

β-Anomer:
Yield 3 mg (2%), colorless oil, $[α]_D^{25}$=+39.3 (c=0.1, CHCl$_3$); R$_F$=0.23 (petroleum ether/ethyl acetate 12:1), HPLC (column C, gradient 1): 22.13 min.

Example 65

Methyl 2-O-ethyl-6-O-tert-butyldiphenylsilyl-3,4-O-isopropylidene-α/β-D-galactopyranoside 400 mg (0.312 mmol) of 33 are reacted with ethyl iodide according to the general working procedure and the product is removed under glycosylating conditions using methanol. The crude product is purified by flash chromatography on silica gel (column 15×2.5 cm, eluent petroleum ether/ethyl acetate 12:1).

α-Anomer:
Yield 22 mg (14%), colorless oil, $[α]_D^{25}$=+73.2 (c=1, CHCl$_3$); R$_F$=0.49 (petroleum ether/ethyl acetate 4:1), HPLC (column C, gradient 1): 19.62 min.

β-Anomer:
Yield 10 mg (7%), colorless oil, $[α]_D^{25}$=+1.1 (c=0.33, CHCl$_3$); R$_F$=0.49 (petroleum ether/ethyl acetate 4:1), HPLC (column C, gradient: 1): 19.62 min.

Example 66

S-(2'-O-Benzyl-3',4'-O-isopropylidene-α/β-D-galactopyranosyl)-4-mercaptobutyric Acid, Polymer-bonded 1 g (0.78 mmol) of 33 is alkylated with benzyl bromide according to: the general procedure (variant A) and the silyl protective group is removed. The polymer is dried in vacuo.

Example 67

Methyl 2-O-benzyl-6-O-(2'-Naphthylmethyl)-3,4-O-isopropyliden-α/β-D-galactopyranoside 400 mg (0.312 mmol) of S-(2'-O-benzyl-3',4'-O-isopropylidene-α/β-D-galactopyranosyl)-4-mercaptobutyric acid—polymer bonded are reacted with 2-bromomethylnaphthalene according to the general working procedures and the product is removed under glycosylating conditions using methanol. The pure product is obtained by flash chromatography on silica gel (column 20×2 cm, eluent petroleum ether/ethyl acetate 4:1) as an anomer mixture in the ratio α:β=10:1.

Yield 40 mg (38%), yellow oil, $[\alpha]_D^{25}=+79.2$ (c=1, CHCl$_3$); R$_F$=0.25 (petroleum ether/ethyl acetate 4:1), HPLC (column C, gradient: 1): 15.28 min.

Example 68

Methyl 2-O-propyl-6-O-tert-butyldiphenylsilyl-3,4-O-isopropylidene-α/β-D-galactopyranoside 400 mg (0.312 mmol) of 33 are reacted with propyl iodide according to the general working procedure and the product is removed under glycosylating conditions using methanol. The crude product is purified by flash chromatography on silica gel (column 17×2.5 cm, eluent petroleum ether/ethyl acetate 12:1).

α-Anomer:
Yield 7 mg (5%), colorless oil, $[\alpha]_D^{25}=+56.9$ (c=0.2, CHCl$_3$); R$_F$=0.51 (petroleum ether/ethyl acetate 4:1), HPLC (column C, gradient 1): 21.03 min.

β-Anomer:
Yield 2 mg (2%), colorless oil, $[\alpha]_D^{25}=+2.7$ (c=0.1, CHCl$_3$); R$_F$=0.57 (petroleum ether/ethyl acetate 4:1), HPLC (column C, gradient 1): 19.62 min.

Example 69

Methyl 2-O-heptyl-6-O-tert-butyldiphenylsilyl-3,4-O-isopropylidene-α/β-D-galactopyranoside 400 mg (0.312 mmol) of 33 are reacted with heptyl iodide with addition of 18-crown-6 according to the general working procedure (variant A) and the product is removed under glycosylating conditions using methanol. The crude product is purified by flash chromatography on silica gel (column 20×2 cm, eluent petroleum ether/ethyl acetate 15:1).

α-Anomer:
Yield 12 mg (7%), colorless oil, $[\alpha]_D^{25}=+52.6$ (c=0.6, CHCl$_3$); R$_F$=0.34 (petroleum ether/ethyl acetate 10:1), HPLC (column C, gradient 1): 24.27 min.

β-Anomer:
Yield 8 mg (5%), colorless oil, $[\alpha]_D^{25}=+14.6$ (c=0.4, CHCl$_3$); R$_F$=0.40 (petroleum ether/ethyl acetate 10:1), HPLC (column C (C$_8$), gradient 1): 24.27 min.

Example 70

Ethyl 3,4-O-isopropylidene-1-thio-β-D-galactopyranoside

A mixture of 19.1 g (85.4 mmol) of ethyl 1-thio-β-D-galactopyranoside, 360 ml (2.93 mol) of acetone dimethyl acetal and 0.3 g (16 mmol) of p-toluenesulfonic acid monohydrate is stirred at room temp. After 18 h, 1.2 ml of triethylamine are added and the mixture is concentrated to dryness in vacuo. The residue is suspended in 180 ml of dichloromethane and treated with 2.4 ml of 50% strength trifluoroacetic acid. After 15 min, 3.6 ml of triethylamine are added and the mixture is concentrated in vacuo. The oil obtained is purified by flash chromatography on silica gel (column 30×10 cm, eluent petroleum ether/ethyl acetate 2:3).

Yield 15.7 g (70%), colorless crystals, melting point 89° C., $[\alpha]=+16.5°$ (c=1, CHCl$_3$); R$_F$=0.33 (petroleum ether/ethyl acetate 1:9).

Example 71

Ethyl 6-O-tert-butyldiphenylsilyl-3,4-O-isopropylidene-1-thio-β-D-galactopyranoside A solution of 9.00 g (34 mmol) of Example compound 70 and 4.62 g (68 mmol) of imidazole in 100 ml of absol. DMF is treated with 10.9 ml (43 mmol) of tert-butyldiphenylsilyl chloride and stirred at room temp. for 3 h. The reaction is terminated by addition of 50 ml of water. 150 ml of dichloromethane are added and the organic phase is washed three times with 50 ml of water each time. The combined aqueous phases: are extracted with 100 ml of dichloromethane, the combined organic phases are dried over magnesium sulfate and the solvent is removed in vacuo. The oil obtained is chromatographed on silica gel (column 20×5 cm, eluent petroleum ether/ethyl acetate 4:1). Yield 12.66 g (74%), colorless crystals, $[\alpha]_D^{25}=+0.7°$ (c=1, CHCl$_3$); R$_F$=0.28 (petroleum ether/ethyl acetate 4:1).

Example 72

Ethyl 2-O-acetyl-3,4-O-isopropylidene-6-O-tert-butyldiphenylsilyl-1-thio-β-D-galactopyranoside 50 ml (520 mmol) of acetyl chloride are added dropwise with ice-cooling to a solution of 12.6 g (25 mmol) of Example compound 71 in 100 ml of absol. pyridine. After 18 h, the solvent is distilled off in vacuo, the residue is taken up in 150 ml of dichloromethane, washed successively with 50 ml each of 0.5 N hydrochloric acid, satd sodium hydrogencarbonate solution and satd sodium chloride solution and the organic phase is dried over magnesium sulfate. After concentrating in vacuo, the residue is separated from impurities by chromatography on silica gel (column 25×5 cm, eluent petroleum ether/ethyl acetate 4:1). The oily product solidifies after several days.

Yield 13.6 g (83%), colorless crystals, melting point 76° C., $[\alpha]_D^{25}=+15.60$ (c=1, CHCl$_3$); R$_F$=0.62 (petroleum ether/ethyl acetate 4:1).

Example 73

Ethyl 2-O-acetyl-6-O-tert-butyldiphenylsilyl-1-thio-β-D-galactopyranoside a) by deacetalization with acetic acid: A solution of 140 mg (0.26 mmol) of Example compound 72 in 20 ml of 60% strength acetic acid is warmed to 60° C. for 2 h with stirring. The mixture is concentrated in vacuo and codistilled with 10 ml of toluene. The residue is taken up in 20 ml of dichloromethane and washed with 10 ml of satd sodium hydrogencarbonate solution. The crude product is purified by chromatography on silica gel (column 15×2 cm, eluent petroleum ether/ethyl acetate 2:3).

Yield 59 mg (45%), colorless oil; the analytical data agree with those indicated under b).

b) by deacetalization with p-TsOH: 11.36 g (21 mmol) of Example compound 72 are dissolved in 200 ml of chloroform, treated with 0.19 g (1 mmol) of p-toluenesulfonic acid monohydrate and 12.27 ml (146 mmol) of ethanedithiol and the mixture is heated under reflux. After 45 min, it is allowed to cool to room temp. and washed with 50 ml each of satd sodium hydrogencarbonate solution, 0.5 N hydrochloric acid and water. The organic phase is dried over magnesium sulfate and then freed from the solvent. Chromatographic purification (column 30×5 cm, eluent petroleum ether/ethyl acetate 2:3) of the crude product yields the title compound after drying in vacuo.

Yield 8.44 g (80%), colorless oil solidifying after days, $[\alpha]_D^{25}=+9.4°$ (c=1, CHCl$_3$); R$_F$=0.39 (petroleum ether/ethyl acetate 1:1).

Example 74

Ethyl 2-O-acetyl-3-O-allyl-6-O-tert-butyldiphenylsilyl-1-thio-β-D-galactopyranoside (28)

A solution of 8.33 g (165 mmol) of Example compound 73 and 4.31 g (173 mmol) of dibutyltin oxide in 150 ml of benzene is heated under reflux in a water separator for 16 h. Half of the solvent is then removed by distillation and 2.42 ml (286 mmol) of allyl bromide are added. The mixture is then stirred at 50° C. for 5 h. It is then concentrated in vacuo, the residue is taken up in 150 ml of dichloromethane, and the organic phase is washed three times with 50 ml of water each time and dried over magnesium sulfate. The solvent is concentrated in vacuo and the crude product is purified by chromatography on silica gel (column 25×8 cm, eluent petroleum ether/ethyl acetate 4:1).

Yield 7.34 g (82%), yellowish oil, $[\alpha]_D^{25}$=+2.4° (c=1, CHCl$_3$); R$_F$=0.35 (petroleum ether/ethyl acetate 4:1).

Example 75

Ethyl 2-O-acetyl-3-O-allyl-1-thio-β-D-galactopyranoside (29)

2.5 ml of a 1 M solution of tetrabutylammonium fluoride in THF are added dropwise to a solution of 5.2 g (9.5 mmol) of 28 in 200 ml of THF and the mixture is stirred at room temp. for 1 h. It is then diluted with 500 ml of dichloromethane, washed with 100 ml of water and the organic phase is dried over magnesium sulfate. After concentrating, the crude product is purified by chromatography on silica gel (column 20×5 cm, eluent petroleum ether/ethyl acetate 2:3).

Yield 2.29 g (79%), yellowish oil, $[\alpha]_D^{25}$=−20.6° (c=1, CHCl$_3$); R$_F$=0.35 (petroleum ether/ethyl acetate 4:1).

Example 76

Ethyl 2-O-acetyl-3-O-allyl-6-O-p-(4'-methoxycarbonylbutyloxy)phenyl-1-thio-β-D-galactopyranoside (30)

A solution of 2.0 ml (13.5 mmol) of diethyl diazodicarboxylate in 5 ml of dichloromethane is added dropwise with stirring to a solution of 2.25 g (9.5 mmol) of 29, 4.7 g (22.5 mmol) of methyl p-hydroxyphenoxybutyrate and 6.0 g (22.5 mmol) of triphenylphosphine in 70 ml of dichloromethane. After 4 h, the mixture is concentrated without further working up and the crude product is purified by chromatography on silica gel (column 20×4 cm, eluent petroleum ether/ethyl acetate 3:1).

Yield 1.92 g (53%), colorless oil, $[\alpha]_D^{25}$=+1.50° (c=1, CHCl$_3$); R$_F$=0.52 (petroleum ether/ethyl acetate 1:1).

Example 77

Ethyl 2-O-acetyl-3-O-allyl-6-O-p-(4'-Methoxycarbonylbutyloxy)phenyl-4-O-β-(trimethylsilyl)ethoxymethyl-1-thio-β-D-galactopyranoside (31)

2.12 ml (12 mmol) of N,N-diisopropylethylamine and 1.59 ml (9 mmol) of β-(trimethylsilyl)ethoxymethyl chloride are added to a solution of 1.51 g (3.02 mmol) of 30 in 20 ml of absol. dichloromethane. The reaction mixture is heated under reflux for 6 h under an argon atmosphere. The reaction is then terminated by addition of 10 ml of methanol and the mixture is concentrated in vacuo. Impurities are separated by means of chromatography on silica gel (column 15×2 cm, eluent petroleum ether/ethyl acetate 3:1).

Yield 1.8 g (90%), colorless oil, $[\alpha]_D^{25}$=−27.0° (c=1, CHCl$_3$); R$_F$=0.40 (petroleum ether/ethyl acetate 3:1).

Example 78

Preparation of Libraries of the Type Alkyl 3,4-O-isopropylidene-2-O-alkyl-6-O-carbamoylgalactoside a) General Procedure for the Coupling of the Methyl Galactosylmercaptobutyrates to Amino-functionalized Polymeric Supports 1.9 g (30 mmol) of lithium hydroxide are added to a solution of 14.6 mmol of the thiogalactoside in 400 ml of THF/methanol/water (2:2:1) and the mixture is stirred at room temp. for 8 h. It is then neutralized (0.5 N hydrochloric acid or phosphate buffer solution), 400 ml of satd sodium chloride solution are added and the mixture is extracted three times with 200 ml of ethyl acetate. The extracts are dried over magnesium sulfate and freed from the solvent in vacuo. The residue is taken up in 150 ml of dichloromethane or DMF and the solution obtained is shaken overnight in a solid-phase reactor with 19.8 mmol of the amino-functionalized polymer concerned, 3.7 ml (14.6 mmol) of N,N'-diisopropylcarbodiimide and 3.86 g (14.6 mmol) of N-hydroxybenzotriazole. The polymer is then filtered off with suction and washed ten times with 50 ml each of DMF and dichloromethane. The loaded polymer is dried in vacuo and the loading with carbohydrate matrix is determined by means of elemental analysis.

b) General Working Procedure for the Capping of the Polymers

A mixture of 1.56 mmol of the polymer concerned is shaken for 18 h with a solution of 0.45 ml (7.80 mmol) of acetic acid, 2.7 ml (15.60 mmol) of N,N-diisopropylethylamine and 3.74 g (7.80 mmol) of PfPyU in 40 ml of DMF. After filtering off the liquid phase with suction, the polymer is washed thoroughly with DMF, dichloromethane and diethyl ether and dried in vacuo.

c) General Working Procedure for the Alkylation of Capped Polymers 0.078 mmol of the polymer concerned is shaken with a solution of 88 mg (0.78 mmol) of potassium tert-butoxide in 2 ml of DMF. After 15 min, the polymer is filtered off and the resin is immediately [lacuna] with a solution of 41 mg (0.16 mmol) of 18-crown-6 and 0.78 mmol of the alkyl halide concerned in 2 ml of DMF. The mixture is shaken for 3 h and the polymer is then filtered off with suction. The resin is washed thoroughly with DMF, methanol, dichloromethane and diethyl ether and dried in vacuo.

d) General Procedure for the Removal of the tert-Butyldiphenylsilyl Protective Group on the Polymeric Support 0.56 ml (0.56 mmol, 1 M) tetrabutylammonium fluoride in THF is added to a suspension of 0.056 mmol of loaded polymer in 1.5 ml of THF. The mixture is shaken for 4 h. The resin is filtered off from the solution and washed five times with 2 ml each of DMF and dichloromethane.

e) General Working Procedure for Carbamoylations

Variant A (Using 1,1'-Carbonyidiimidazole and Amines)

A solution of 0.25 g (1.56 mmol) of 1,1'-carbonyldiimidazole in 2 ml of DMF or dioxane is added to 0.078 mmol of polymer with 0.1 ml (0.58 mmol) of N,N-diisopropylethylamine, a spatula-tipful of DMAP and a spatula-tipful of KOtBu. The mixture is shaken for 2 h and filtered. The polymer is then shaken overnight with a solution of 1.56 mmol of the appropriate amine in 2 ml of DMF. It is filtered and washed five times each with DMF and dichloromethane.

Variant B (Using Isocyanates)

A solution of 1.56 mmol of the appropriate isocyanate in 2 ml of dioxane is added to 0.078 mmol of polymer. A spatula-tipful of DMAP is then added and the mixture is shaken for 3–7 h, depending on the reactivity of the OH group to be reacted. It is filtered and the polymer is washed thoroughly with dioxane, methanol and dichloromethane.

f) General Procedure for the Removal of the Galactose Derivatives from the Polymeric Support A suspension of 0.056 mmol of polymer-bonded galactose derivative in 1.5 ml of abs. dichloromethane is shaken at room temp. in a 5 ml PE syringe (PE frit, plastic cap) with 0.3 ml of a 3.5% strength (0.36 ml of bromine to 10 ml of dichloromethane or 5–10 eq. of bromine) solution of bromine in abs. dichloromethane and 0.08 ml (0.36 mmol) of 2,6-di-tert-butylpyridine or a corresponding amount of polymer-bonded 2,6-di-tert-butylpyridine. After 15 min, 0.2 ml of cyclohexene, 0.2 ml of the abs. alcohol to be glycosylated and 25 mg (0.056 mmol) of tetraethylammonium bromide are added. After 4 h, the resin is filtered off and washed five times with 1 ml of dichloromethane. The combined filtrates are freed from the solvent in vacuo. The crude product obtained is applied to a silica gel cartridge in a little dichloromethane. The cartridge is eluted first with 30 ml of petroleum ether. This fraction is discarded. The product is obtained by eluting with suitable petroleum ether/ethyl acetate mixtures. If the mixture is distributed in various alcohols, it is advantageously additionally shaken with bromine solution and 2,6-di-tert-butylpyridine. The solution is injected into a vessel from the syringe and washed 5x with abs. dichloromethane. This resulting mixture is distributed in various vessels which contain the ammonium bromide, cyclohexene and the respective alcohol. The vessels are sealed and shaken. Standing for too long in the air is to be avoided in the case of the bromine solutions, as these are moisture-sensitive.

Parallel Synthesis

6×3.1 g (2.42 mmol) of 33 are treated with PfPyU and acetic acid according to the general procedure. The resins thus obtained are alkylated with methyl iodide, ethyl iodide, heptyl iodide, benzyl bromide, p-bromobenzyl bromide and o-cyanobenzyl bromide according to the general procedure. The silyl protective group is then removed according to the general procedure. 150 mg each (about 0.119 mmol) of the resins obtained are then reacted either with diethylamine, benzytamine, methoxyethylamine, cyclopropylmethylamine or glycine tedt-butyl ester according to the general procedure or with p-chlorophenyl isocyanate, o-trifluoromethylphenyl isocyanate, o-nitrophenyl isocyanate, p-cyanophenyl isocyanate, m,p-dichlorophenyl isocyanate, m-fluorophenyl isocyanate, phenyl isocyanate, n-propyl isocyanate, tert-butyl isocyanate or ethyloxycarbonylmethyl isocyanate according to the general procedure. The polymers are swollen in 2 ml of dichloromethane and shaken for 20 min with 0.9 ml in each case of a 3.5% strength bromine solution in dichloromethane and 0.24 ml (1.08 mmol) of 2,6-di-tert-butylpyridine. The polymers are filtered off and washed a number of times with dichloromethane. The solutions obtained are divided into three and shaken for 5 h each with 55 mg (0.26 mmol) of tetraethylammonium bromide, 0.2 ml of cyclohexene and 0.2 ml of methanol, ethanol or i-propanol. The solutions are concentrated in vacuo. The residues are taken up in 250, jl of dichloromethane each and applied to silica gel cartridges. They are washed with 30 ml each of petroleum ether and the eluate is discarded. They are then eluted with 5 ml each of petroleum ether/ethyl acetate (1:1) and the product obtained is concentrated in vacuo. By activation with CDl (variant A), the following compounds of the formula (A) are obtained:

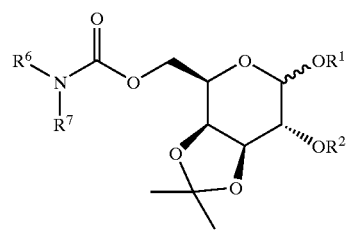

(A)

| | $R^2$ | $R^5$ | $R^7$ | $R^1$ | Yield | $R_T{}^{a)}$ | $R_F{}^{b)}$ |
|---|---|---|---|---|---|---|---|
| 1 | 4-BrBn | CH$_3$O(CH$_2$)$_2$ | H | Me | 2 mg (10%) | 18.41 | 0.60 |
| 2 | 4-BrBn | c-PrCH$_2$ | H | Me | 3 mg (15%) | 17.69 | 0.58 |
| 3 | 4-BrBn | t-BuOOCCH$_2$ | H | Me | 9 mg (41%) | 18.28, 18.59 | 0.59 |
| 4 | 2-CNBn | c-PrCH$_2$ | H | Me | 4 mg (23%) | 15.81 | 0.28 |
| 5 | 2-CNBn | t-BuOOCCH$_2$ | H | Me | 4 mg (20%) | 17.35 | 0.58 |
| 6 | Bn | Et | Et | Et | 11 mg (64%) | 18.21, 18.48 | 0.62, 0.68 |
| 7 | Bn | c-PrCH$_2$ | H | Et | 6 mg (35%) | 16.94 | 0.55 |
| 8 | Bn | Bn | H | Et | 10 mg (54%) | 17.69, 18.03 | 0.60 |
| 9 | Bn | t-BuOOCCH$_2$ | H | Et | 6 mg (31%) | 17.60, 17.91 | 0.57 |
| 10 | 4-BrBn | Et | Et | Et | 5 mg (25%) | 19.29, 19.72 | 0.75 |
| 11 | 4-BrBn | CH$_3$O(CH$_2$)$_2$ | H | Et | 4 mg (19%) | 19.05 | 0.36 |
| 12 | 4-BrBn | c-PrCH$_2$ | H | Et | 4 mg (20%) | 18.04 | 0.70 |
| 13 | 4-BrBn | t-BuOOCCH$_2$ | H | Et | 6 mg (30%) | 18.97, 19.33 | 0.72 |
| 14 | 2-CNBn | Bn | H | Et | 5 mg (26%) | 17.13, 17.34 | 0.60 |
| 15 | 2-CNBn | CH$_3$O(CH$_2$)$_2$ | H | Et | 2 mg (11%) | 13.86 | 0.21 |
| 16 | 2-CNBn | c-PrCH$_2$ | H | Et | 5 mg (28%) | 16.30, 16.53 | 0.59 |
| 17 | 2-CNBn | r-BuOOCCH$_2$ | H | Et | 5 mg (25%) | 17.04, 17.23 | 0.66 |

-continued

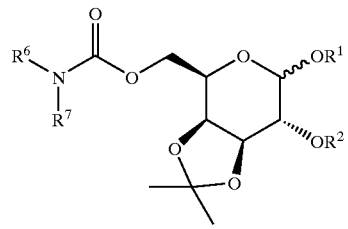

(A)

| | R² | R⁵ | R⁷ | R¹ | Yield | $R_T^{a)}$ | $R_F^{b)}$ |
|---|---|---|---|---|---|---|---|
| 18 | Bn | Et | Et | i-Pr | 9 mg (51%) | 17.79, 17.96 | 0.74 |
| 19 | Bn | Bn | H | i-Pr | 10 mg (53%) | 18.36, 18.65 | 0.72 |
| 20 | Bn | CH₃O(CH₂)₂ | H | i-Pr | 3 mg (17%) | 15.84, 16.21 | 0.43 |
| 21 | Bn | c-PrCH₂ | H | i-Pr | 10 mg (57%) | 17.63, 17.94 | 0.70 |
| 22 | Bn | t-BuOOCCH₂ | H | i-Pr | 8 mg (40%) | 18.22, 18.51 | 0.74 |
| 23 | 4-BrBn | Et | Et | i-Pr | 3 mg (15%) | 20.48, 20.68 | 0.48 |
| 24 | 4-BrBn | CH₃O(CH₂)₂ | H | i-Pr | 5 mg (24%) | 19.26, 19.70 | 0.11 |
| 25 | 4-BrBn | c-PrCH₂ | H | i-Pr | 3 mg (15%) | 19.10 | 0.49 |
| 26 | 4-BrBn | t-BuOOCCH₂ | H | i-Pr | 12 mg (52%) | 19.26, 19.50 | 0.50 |
| 27 | 2-CNBn | Bn | H | i-Pr | 6 mg (30%) | 17.79, 17.94 | 0.66 |
| 28 | 2-CNBn | c-PrCH₂ | H | i-Pr | 5 mg (27%) | 17.03, 17.18 | 0.64 |
| 29 | 2-CNBn | t-BuOOCCH₂ | H | i-Pr | 5 mg (24%) | 16.23 | 0.66 |

By activation with isocyanates (variant B), the following compounds of the formula B are obtained

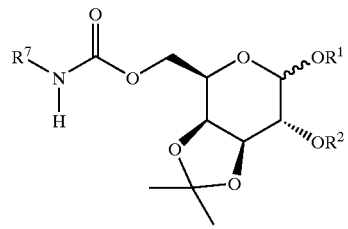

B

| | R⁷ | R₂ | Yield | $R_T^{b)}$ | $R_F^{b)}$ |
|---|---|---|---|---|---|
| 1 | 4-ClPh | Me | 5 mg | 18.75 | 0.20; 0.16 |
| 2 | 2-CF₃Ph | Me | 5 mg (30%) | 18.94 | 0.31; 0.26 |
| 3 | 2-NO₂Ph | Me | 5 mg (31%) | 18.80 | 0.30; 0.26 |
| 4 | 4-CN-Ph | Me | 3 mg (20%) | 13.93 | 0.06 |
| 5 | 3,4-Cl₂Ph | Me | 4 mg (26%) | 19.35 | 0.20; 0.14 |
| 6 | 4-ClPh | Me | 5 mg (31%) | 16.53 | 0.34 |
| 7 | 2-CF₃Ph | Me | 5 mg (29%) | 17.63 | 0.46 |
| 8 | 2-NO₂Ph | Me | 9 mg (54%) | 16.36 | 0.46 |
| 9 | 4-CN-Ph | Me | 4 mg (25%) | 14.75 | 0.13 |
| 10 | 3,4-Cl₂Ph | Me | 5 mg (29%) | 17.84 | 0.29 |
| 11 | 4-ClPh | Me | 9 mg (48%) | 21.35 | 0.63 |
| 12 | 2-CF₃Ph | Me | 14 mg (69%) | 21.27 | 0.61 |
| 13 | 2-NO₂Ph | Me | 11 mg (57%) | 21.08 | 0.70 |
| 14 | 4-CN-Ph | Me | 5 mg (32%) | 20.04 | 0.36 |
| 15 | 3,4Cl₂Ph | Me | 7 mg (35%) | 23.38 | 0.63 |
| 16 | 4-ClPh | Me | 5 mg (23%) | 19.90; 20.05 | 0.30 |
| 17 | 2-CF₃Ph | Me | 10 mg (43%) | 19.49 | 0.40 |
| 18 | 2-NO₂Ph | Me | 9 mg (41%) | 19.78; 19.88 | 0.39 |
| 19 | 4-CN-Ph | Me | 3 mg (14%) | 18.53; 18.64 | 0.13 |
| 20 | 3,4Cl₂Ph | Me | 9 mg (39%) | 20.65; 20.95 | 0.34; 0.26 |
| 21 | 4-ClPh | Me | 4 mg | 16.12; 16.92 | 0.29; 0.21 |
| 22 | 2-CF₃Ph | Me | 7 mg (34%) | 20.72 | 0.33 |
| 23 | 2-NO₂Ph | Me | 6 mg (30%) | 17.83 | 0.31 |
| 24 | 4-CN-Ph | Me | 3 mg | 14.46 | 0.10 |
| 25 | 3,4-Cl₂Ph | Me | 4 mg (19%) | 19.26; 19.69 | 0.24 |
| 26 | 4-ClPh | Et | 4 mg (25%) | 18.98 | 0.29 |
| 27 | 2-CF₃Ph | Et | 5 mg (29%) | 15.93; 16.09 | 0.42 |
| 28 | 2-NO₂Ph | Et | 4 mg (24%) | 14.49 | 0.40 |

-continued

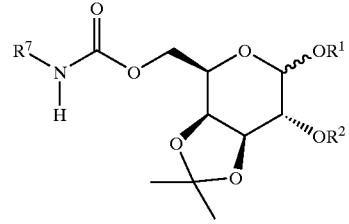

B

| | R⁷ | R₂ | Yield | $R_T^{b)}$ | $R_F^{b)}$ |
|---|---|---|---|---|---|
| 29 | 4-CN-Ph | Et | 3 mg | 12.21 | 0.15 |
| 30 | 3,4-Cl₂Ph | Et | 4 mg (23%) | 19.69; 19.90 | 0.33 |
| 31 | 4-ClPh | Et | 4 mg (24%) | 17.26 | 0.54 |
| 32 | 2-CF₃Ph | Et | 8 mg (44%) | 16.79 | 0.38 |
| 33 | 2-NO₂Ph | Et | 7 mg (41%) | 17.24 | 0.55 |
| 34 | 4-CN-Ph | Et | 4 mg (24%) | 15.55 | 0.27 |
| 35 | 3,4-Cl₂Ph | Et | 4 mg (22%) | 18.63 | 0.46 |
| 36 | 4-ClPh | Et | 9 mg (46%) | 21.91; 22.07 | 0.75 |
| 37 | 2-CF₃Ph | Et | 11 mg (53%) | 20.99; 21.16 | 0.71; 0.64 |
| 38 | 2-NO₂Ph | Et | 9 mg (45%) | 22.14 | 0.80 |
| 39 | 4-CN-Ph | Et | 6 mg (31%) | 20.64; 20.79 | 0.57 |
| 40 | 3,4-Cl₂Ph | Et | 8 mg (38%) | 22.28 | 0.77 |
| 41 | 4-ClPh | Et | 4 mg (18%) | 18.98 | 0.46 |
| 42 | 2-CF₃Ph | Et | 10 mg (42%) | 19.89; 20.18 | 0.55 |
| 43 | 2-NO₂Ph | Et | 6 mg (27%) | 20.59; 20.74 | 0.55 |
| 44 | 4-CN-Ph | Et | 4 mg (18%) | 18.73; 19.31 | 0.25 |
| 45 | 3,4-Cl₂Ph | Et | 8 mg (34%) | 19.39; 19.53 | 0.45 |
| 46 | 4-ClPh | Et | 6 mg (30%) | 16.11 | 0.35 |
| 47 | 2-CF₃Ph | Et | 6 mg (29%) | 20.68; 21.0$^{e)}$ | 0.45; 0.36 |
| 48 | 2-NO₂Ph | Et | 6 mg (29%) | 18.61 | 0.41 |
| 50 | 3,4-Cl₂Ph | Et | 3 mg (14%) | 19.68; 19.82 | 0.33 |
| 51 | 4-ClPh | i-Pr | 4 mg (24%) | 17.12; 18.89 | 0.35 |
| 52 | 2-CF₃Ph | i-Pr | 11 mg (61%) | 21.66 | 0.48 |
| 53 | 2-NO₂Ph | i-Pr | 8 mg (47%) | 17.16 | 0.45 |
| 55 | 3,4-Cl₂Ph | i-Pr | 4 mg (22%) | 19.66 | 0.35 |
| 56 | 4-ClPh | i-Pr | 6 mg (35%) | 17.90; 18.07 | 0.66 |
| 57 | 2-CF₃Ph | i-Pr | 9 mg (48%) | 17.60; 17.84 | 0.55 |
| 58 | 2-NO₂Ph | i-Pr | 8 mg (45%) | 17.22; 18.06 | 0.66 |
| 59 | 4-CN-Ph | i-Pr | 4 mg (24%) | 16.31 | 0.38 |
| 60 | 3,4-Cl₂Ph | i-Pr | 4 mg (22%) | 16.35 | 0.54 |
| 61 | 4-ClPh | i-Pr | 6 mg (30%) | 22.47 | 0.77 |

-continued

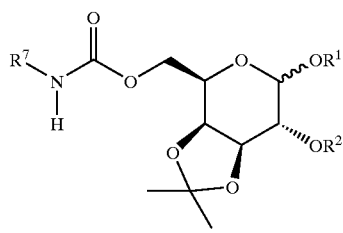

B

| | R[7] | R[2] | Yield | R[T][b)] | R[F][b)] |
|---|---|---|---|---|---|
| 62 | 2-CF₃Ph | i-Pr | 10 mg (47%) | 22.15; 22.39 | 0.71; 0.64 |
| 63 | 2-NO₂Ph | i-Pr | 9 mg (44%) | 22.61; 22.92 | 0.79 |
| 64 | 4-CN-Ph | i-Pr | 5 mg (25%) | 21.25 | 0.59 |
| 65 | 3,4-Cl₂Ph | i-Pr | 7 mg (36%) | 23.47 | 0.80 |
| 66 | 4-ClPh | i-Pr | 7 mg (31%) | 21.04 | 0.52 |
| 67 | 2-CF₃Ph | i-Pr | 10 mg (42%) | 23.71[e)] | 0.62 |
| 68 | 2-NO₂Ph | i-Pr | 8 mg (34%) | 21.30 | 0.57 |
| 69 | 4-CN-Ph | i-Pr | 7 mg (31%) | 22.43; 22.5[e)] | 0.43; 0.33 |
| 70 | 3,4-Cl₂Ph | i-Pr | 10 mg (41%) | 21.72 | 0.60; 0.52 |
| 72 | 2-CF₃Ph | i-Pr | 6 mg (27%) | 23.78[e)] | 0.47; 0.41 |
| 73 | 2-NO₂Ph | i-Pr | 6 mg (28%) | 22.16[e)] | 0.54; 0.50 |
| 74 | 4-CN-Ph | i-Pr | 3 mg (15%) | 16.78[e)] | 0.29 |
| 75 | 3,4-Cl₂Ph | i-Pr | 7 mg (32%) | 23.13[e)] | 0.48; 0.42 |
| 76 | 4-Br-Ph | Me | 4 mg (19%) | 15.29; 15.73 | 0.27 |
| 77 | Pr | Me | 5 mg (30%) | 17.27 | 0.16 |
| 79 | 3-F-Ph | Me | 4 mg (21%) | 16.92; 17.06 | 0.25 |
| 80 | EtOOCCH₂ | Me | 4 mg (22%) | 17.28 | 0.09 |
| 81 | 4-Br-Ph | Et | 4 mg (18%) | 18.98 | 0.45 |
| 82 | Pr | Et | 5 mg (29%) | 16.02; 19.41 | 0.25 |
| 83 | t-Bu | Et | 4 mg (22%) | 17.72 | 0.46 |
| 84 | 3-F-Ph | Et | 4 mg (21%) | 19.35 | 0.48 |
| 85 | EtOOCCH₂ | Et | 4 mg (21%) | 17.99 | 0.21 |
| 86 | 4-Br-Ph | i-Pr | 3 mg (13%) | 19.44 | 0.48 |
| 87 | Pr | i-Pr | 5 mg (28%) | 16.84 | 0.32 |
| 88 | t-Bu | i-Pr | 3 mg (16%) | 13.65 | 0.48 |
| 89 | 3-F-Ph | i-Pr | 3 mg (15%) | 19.90 | 0.55; 0.48 |
| 90 | EtOOCCH₂ | i-Pr | 2 mg (10%) | 19.16[e)] | 0.50 |

[a)]Column B, grad. 2;
[b)]Petroleum ether/ethyl acetate (2:1);
[e)]Column B, grad. 3
Column B: Beckmann unit (Gold System), Nucleosil 100-5 C18 column measured at 220 and 254 nm
Grad. 2 = CH₃CN:H₂O 10:90 - 90 - 10, flow 1 ml/min, 0.1% TFA
Grad. 3 = CH₃CN:H₂O 10:90 - 90 - 10, flow 0.65 ml/min, 0.1% TFA Example 79

Functionalization of the 1-, 2-, 4- and 6-position

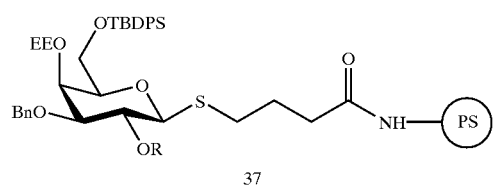

37

1. a) KOtBu, DMF
   b) R2X, 18-crown-6, DMF
2. TBAF, THF
3. Alkylation or carbamoylation (R7)
4. PPTS, dioxane/MeOH (10:1)
5. R6NCO, DMAP, CH₂Cl₂
6. a) Br₂, DTBP, CH₂Cl₂
   b) R1OH, c-hexane, TEAB, CH₂Cl₂

-continued

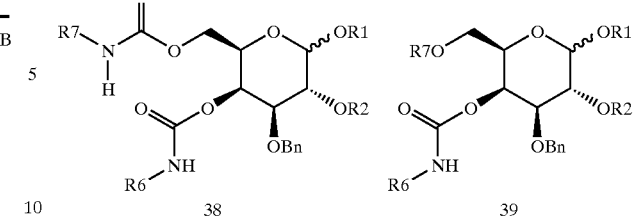

The following compounds are obtained:

| | R[2] | R[7] | R[6] | R[1] | Yield (%) |
|---|---|---|---|---|---|
| 38-1 | Pr | o-NO₂Ph | o-CF₃Ph | Me | 20[a)] |
| 38-2 | p-BrBn | c-PrCH₂ | o-NO₂Ph | Et | 15 |
| 38-3 | Hep | p-CN-Bn | o-CF₃Ph | i-Pr | 6 |
| 39-1 | p-tBuBn | CH₂COOtBu | p-ClPh | Me | 14 |

Example 80

Methyl 4-S-(2'-O-Acetyl-3'-O-benzyl-6'-O-tert-butyldiphenylsilyl-β-D-galactopyranosyl)-4-mercaptobutyrate A mixture of 4.0 g (6.9 mmol) of Example compound 14a and 2.1 g (8.32 mmol) of dibutyltin oxide in 50 ml of benzene is heated under reflux for 2 h in a water separator. 25 ml of benzene are then removed by distillation and the mixture is treated with 3.1 g (8.3 mmol) of tetrabutylammonium bromide and 1.4 ml (11.8 mmol) of benzyl bromide. The solution is stirred at 50° C. for 16 h and then largely concentrated in vacuo. It is taken up in 50 ml of dichloromethane and washed three times with 10 ml of water each time. After drying over magnesium sulfate, the solvent is removed in vacuo. The crude product is purified by chromatography on silica gel (column 20×5 cm, eluent petroleum ether/ethyl acetate 4:1).

Yield 2.66 g (58%), yellowish oil, $[\alpha]_D^{25}=+3.0°$ (c=1, CHCl₃); $R_F$=0.25 (petroleum ether/ethyl acetate 4:1).

Example 81

Methyl S-(2'-O-Acetyl-3'-O-benzyl4'-O-[1"-(R/S)-ethoxyethyl]-6'-O tert-butyldiphenylsilyl-β-D-galactopyranosyl)-4-mercaptobutyrate A solution of 2.58 g (3.86 mmol) of Example compound 80 in 100 ml of dichloromethane is stirred at room temp. for 4 h after addition of 50 ml of ethyl vinyl ether and 0.49 g (1.93 mmol) of pyridinium p-toluenesulfonate. The mixture is poured into satd sodium hydrogencarbonate solution and the aqueous phase is extracted with ethyl acetate. The combined organic phases are then dried over magnesium sulfate and freed from the solvent in vacuo. Purification is carried out by chromatography on silica gel (column 15×3 cm, eluent petroleum ether/ethyl acetate 4:1).

Yield 1.25 g (45%), yellowish oil, $[\alpha]_D^{25}=-13.3°$ (c=1, CHCl₃); $R_{F=0.22}$ (petroleum ether/ethyl acetate 4:1).

Example 82

Methyl S-(3'-O-benzyl4'-O-[1"-(R/S)-ethoxyethyl]-6'-O-tert-butyldiphenylsilyl-β-D-galactopyranosyl)4-mercaptobutyrate, Polymer-bound According to the general working procedure, 1.45 g (1.60 mmol) of aminomethyl polystyrene are loaded with 1.25 g (1.69 mmol) of Example compound 81.

Loading according to sulfur content of the elemental analysis: 0.61 mmol/g.

Example 83

Functionalization of the 1, 2, 3, 4 and 6-position 1. a) KOtBu, DMF
   b) R5X, 18-crown-6, DMF
2. TBAF, THF
3. Alkylation or carbamoylation (R5)
4. PPTS, dioxane/MeOH (10:1)
5. R6NCO, DMAP, dioxane
6. a) [Ir(COD)(PmePh$_2$)$_2$]PF$_6$, H$_2$, dioxane
   b) PPTS, dioxane/MeOH (10:1); 50° C.
7. R7NCO, DMAP, dioxane
8. a) Br$_2$, DTBP, CH$_2$Cl$_2$
   b) R1OH, c-hexene, TEAB, CH$_2$Cl$_2$ The following compounds are obtained:

|      | R$^2$     | R$^5$               | R$^6$        | R$^7$      | R$^1$ | Yield (%) |
|------|-----------|---------------------|--------------|------------|-------|-----------|
| 41-1 | p-tBuBn   | 2 × Et (from Et$_2$NH) | p-Cl-Ph   | o-NO$_2$Ph | Me    | 23        |
| 41-2 | Hep       | o-NO$_2$Ph          | o-CF$_3$Ph   | p-CN-Ph    | Me    | 16*       |
| 41-3 | p-BrBn    | m,p-Cl$_2$Ph        | o-CF$_3$Ph   | p-Cl-Ph    | i-Pr  | 5         |
| 42-1 | p-BrBn    | Hep                 | o-NO$_2$Ph   | p-Cl-Ph    | Me    | 38        |
| 42-2 | p-tBuBn   | Bu                  | o-NO$_2$Ph   | p-CN-Ph    | i-Pr  | 4         |
| 42-3 | Bn        | CH$_2$COOtBu        | o-NO$_2$Ph   | p-Cl-Ph    | Me    | 6         |

*) Minor component (according to chromatography)

Example 84

S-(3'-O-Allyl4'-O-[1"-(R/S)-ethoxyethyl]-6'-O-tert-butyldiphenylsilyl-β-D-galactopyranosyl)-4-mercaptobutyric Acid, Polymer-bound (40)

8.60 g (9.5 mmol) of aminomethylpolystyrene are loaded with 6.70 g (10.0 mmol) of 21 (Ex. 14c) according to the general procedure. Loading according to sulfur content of the elemental analysis: 0.93 mmol/g.

What is claimed is:

1. A compound of the formula II, where formula II is chosen from formula IIa, IIb, and IIc:

and wherein

R$^1$ is a group of the formula III $$(C_1–C_6)\text{-alkylene-[N—C(O)]}_n–[(C_6–C_{12})\text{-arylene}]_p–(C_0–C_6)\text{-alkylene-C(O)R}^9 \quad \text{(III)}$$

in which n and p are 0 or 1, where p and n cannot simultaneously be 1;

R$^2$ in the case in which X is equal to O,
  is acetyl or banzoyl;
  in the case in which X is equal to N
  is a phthaloyl protective group, DDE (1-(4,4-dimethyl-2,6-dioxocyclohexylideneethyl) or NDE (2-acetyl-4-nitroindan-1,3-dione);

R$^3$ is an allyl protective group;

R$^4$ is ethoxy or SEM (2-(trimethylsilyl)ethoxymethyl);

R$^5$ is tert-butyidimethylsilyl or tert-butyldiphenylsilyl;

R$^9$ is OR$^{10}$ or NR$^{11}$R$^{11}$, where

R$^{10}$ is H, (C$_1$–C$_6$)-alkyl, (C$_1$–C$_6$)-alkyl-(C$_6$–C$_{12}$)-aryl, and R$^{11}$ independently of one another is H, (C$_1$–C$_6$)-alkyl, (C$_1$–C$_6$)-alkyl-(C$_6$–C$_{12}$)-aryl or a polymeric solid support;

Y is O or S; and

X is O or N.

2. A compound of the formula II, where formula II is chosen from formula IIa, IIb, and IIc:

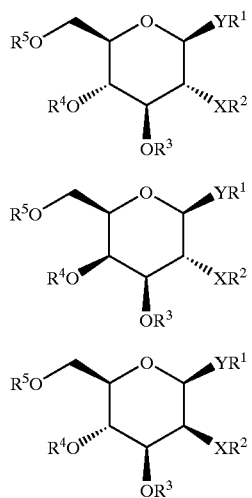

and wherein

R[1] is a linker group which can be linked via a covalent bond to a carrier functionalized by a heteroatom;

R[2] is a phthaloyl protective group, DDE (1-(4,4-dimethyl-2,6-dioxocyclohexylideneethyl) or NDE (2-acetyl-4-nitroindan-1,13-dione);

R[3] is an allyl protective group;

R[4] is ethoxy or SEM (2-(trimethylsilyl)ethoxymethyl);

R[5] is tert-butyldimethylsilyl or tert-butyldiphenylsilyl;

Y is S; and

X is N.

* * * * *

UNITED STATES PATENT AND TRADEMARK OFFICE
CERTIFICATE OF CORRECTION

PATENT NO. : 6,756,489 B1
DATED : June 29, 2004
INVENTOR(S) : Wolfgang Schmidt et al.

It is certified that error appears in the above-identified patent and that said Letters Patent is hereby corrected as shown below:

Title page,
Item [57], ABSTRACT,
Line 6, "$R_2$," should read -- $R^2$, --.

Column 58,
Line 37, "banzoyl;" should read -- benzoyl; --.
Line 43, "ethoxy" should read -- ethoxyethyl --.
Line 44, "tert-butyidimethylsilyl" should read -- tert-butyldimethylsilyl --.

Column 60,
Line 9, "nitroindan-1,13-dione);" should read -- nitroindan-1,3-dione); --.
Line 12, "ethoxy" should read -- ethoxyethyl --.

Signed and Sealed this

Twelfth Day of October, 2004

JON W. DUDAS
*Director of the United States Patent and Trademark Office*